US009511115B2

(12) United States Patent
Soo et al.

(10) Patent No.: US 9,511,115 B2
(45) Date of Patent: Dec. 6, 2016

(54) PHARMACEUTICAL COMPOSITIONS FOR TREATING OR PREVENTING BONE CONDITIONS

(75) Inventors: Chia Soo, Beverly Hills, CA (US); Kang Ting, Beverly Hills, CA (US); Shunichi Kuroda, Osaka (JP); Ben Wu, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 12/897,397

(22) Filed: Oct. 4, 2010

(65) Prior Publication Data

US 2011/0300184 A1 Dec. 8, 2011

Related U.S. Application Data

(62) Division of application No. 11/884,525, filed as application No. PCT/US2006/005473 on Feb. 16, 2006, now Pat. No. 7,833,968.

(60) Provisional application No. 60/653,722, filed on Feb. 16, 2005.

(51) Int. Cl.

| | |
|---|---|
| ***C07K 14/51*** | (2006.01) |
| ***A61K 35/32*** | (2015.01) |
| ***A61K 38/17*** | (2006.01) |
| ***A61L 27/22*** | (2006.01) |

(52) U.S. Cl.

CPC .......... *A61K 38/1709* (2013.01); *A61L 27/227* (2013.01); *G01N 2800/10* (2013.01); *Y10T 436/143333* (2015.01)

(58) Field of Classification Search

CPC ...... C07K 14/51; A61K 35/32; A61K 38/1875

See application file for complete search history.

(56) References Cited

U.S. PATENT DOCUMENTS

| | | | |
|---|---|---|---|
| 4,394,370 | A | 7/1983 | Jefferies |
| 4,409,332 | A | 10/1983 | Jefferies et al. |
| 5,385,887 | A | 1/1995 | Yim et al. |
| 5,486,359 | A | 1/1996 | Caplan et al. |
| 5,674,725 | A | 10/1997 | Beertsen et al. |
| 5,674,844 | A | 10/1997 | Kuberasampath et al. |
| 5,763,416 | A | 6/1998 | Bonadio et al. |
| 5,854,207 | A | 12/1998 | Lee et al. |
| 5,916,870 | A | 6/1999 | Lee et al. |
| 5,942,496 | A | 8/1999 | Bonadio et al. |
| 5,948,428 | A | 9/1999 | Lee et al. |
| 6,077,987 | A | 6/2000 | Breitbart et al. |
| 6,083,690 | A | 7/2000 | Harris et al. |
| 6,200,606 | B1 | 3/2001 | Peterson et al. |
| 6,352,972 | B1 | 3/2002 | Nimni et al. |
| 6,413,998 | B1 | 7/2002 | Petrie et al. |
| 6,462,019 | B1 | 10/2002 | Mundy et al. |
| 7,052,856 | B2 * | 5/2006 | Ting ............................ 435/7.21 |
| 2003/0143688 | A1 | 7/2003 | Fujiwara et al. |

FOREIGN PATENT DOCUMENTS

| | | |
|---|---|---|
| WO | WO 01/24821 | 4/2001 |
| WO | WO 2004/024893 | 3/2004 |
| WO | WO 2004/072100 | 8/2004 |

OTHER PUBLICATIONS

Supplementary European Search Report for PCT/US2006005473, mailed Dec. 8, 2008, 16 pgs.

Aghaloo et al., "Nell-1 induces bone marrow stromal cell differentiation and mineralization in vitro and bone formation in vivo", J. of the Am Coll. Of Surgeons vol. 201, No. 3S, p. S45 (2005).

Cowan et al., "Nell-1 induces osteogenic differentiation and bone formation within calvarial defects", J. f the Am Coll. Of Surgeons vol. 201, No. 3S, p. S61 (2005).

Cowan et al., "Nell-1 induced bone formation within the distracted intermaxillary suture" Bone, Pergamon press, vol. 38, No. 1, pp. 48-58 (2006).

Kuroda et al., "Biochemical Characterization and Expression Analysis of Neural Thrombospondin-1-like Proteins NELL1 and NELL2", Biochem. and Biophysical Research Communications 265, pp. 79-86 (1999).

Kuroda et al., "Involment of Epidermal Growth Factor-like Domain of NELL Proteins in the Novel Protein-Protein Interaction with protein Kinase C", Biochem. and Biophysical Research Communications 265, pp. 752-757 (1999).

Beck et al. "TGF-$\beta_1$ Induces Bone Closure of Skull Defects." J. of Bone Miner. Res. vol. 6, No. 11:1257-1265 (1991).

Bellows et al., "Determination of Numbers of Osteoprogenitors Present in Isolated Fetal Rat Calvaria Cells in Vitro", Developmental Biology, vol. 133, pp. 8-13 (1989).

Burger et al., "Octeoblast and Osteoclast Precursors in Primary Cultures of Calvarial Bone Cells", Anat Rec. vol. 214 (1) pp. 32-40, Abstract only (1986).

Chen et al. "Structure, Chromosomal Localization, and Expression Pattern of the Murine Magp Gene," J. Biol Chem. vol. 268, No. 36: 27381-27389 (1998).

Crawford et al. "Thrombospondin-1 is a Major Activator of TGF-$\beta_1$ in Vivo." Cell, vol. 93:1159-1170 (1998).

Francois and Bier "Xenopus chordin and *Drosophila* short gastrulation Genes Encode Homologous Proteins Functioning in Dorsal-Ventral Axis Formation" Cell, vol. 80:19-20 (1995).

Gelbart, "Databases in Genomic Reseach", Science, vol. 282, pp. 659-661 (1998).

Hoshi, K. et al., "Fibroblasts of Spinal Ligaments Pathologically Differentiate Into Chondrocytes Induced by Recombinant Human Bone Morphogenetic Protein-2: Morphological Examinations for Ossification of Spinal Ligaments", Bone vol. 21, No. 2, pp. 155-162 (1997).

Kim et al., "NELL-1 Enhances Mineralization in Fetal Calvarial Osteoblastic Cells", Plastic Surgery, Surgical Forum, pp. 599-601 (1999).

Kuroda et al., "Involvement of Epidermal Growth Factor-like Domain of NELL Proteins in the Novel Protein-Protein Interaction with Protein Kinase C[1]", Biochemical and Biophysical Research Comm., vol. 265, pp. 752-757 (1999).

(Continued)

*Primary Examiner* — Karen Cochrane Carlson

(74) *Attorney, Agent, or Firm* — Duane Morris LLP

(57) ABSTRACT

Provided herein is a pharmaceutical composition for treating, preventing or ameliorating a bone or cartilage condition and methods of making and using the same.

24 Claims, 10 Drawing Sheets

(56) References Cited

OTHER PUBLICATIONS

Kuroda et al., "Biochemical Characterization and Expression Analysis of Neural Thrombospondin-1-like Proteins NELL 1 and NELL 2", Biochemical and Biophysical Research Comm. vol. 265, pp. 79-86 (1999).
Liu et al., "Simultaneous Detection of Multiple Bone-Related mRNAs and Protein Expression during Osteoblast Differentiation: Polymerase Chain Reaction and Immunocytochemical Studies at the Single Cell Level", Developmental Biology, vol. 166, pp. 220-234 (1994).
Luce et al., "The neuronal EGF-related genes NELL1 and NELL2 are expressed in Hemopoietic cells and developmentally regulated in the B lineage", Gene 231, pp. 121-126 (1999).
Opperman et al., "TGF-β1, TGF-β2, and TGF- β3 Exhibit Distinct Patterns of Expression During Cranial Suture Formation and Obliteration In Vivo and In Vitro", Journal of Bone and Mineral Research, vol. 12, No. 3, pp. 301-310 (1997).
Piccolo et al. "Dorsoventral Patterning in Xenopus: Inhibition of Ventral Signals by Direct Binding of Chordin to BMP-4" Cell, vol. 86: 589-598 (1996).
Siris et al., "Design of NORA, the National Osteoporosis Risk Assessment Program: A Longitudinal US Registry of Postmenopausal Women", Ostreoporos Int. Suppl. 1, pp. 62-69 (1998).
Takagi et al., "The reaction of the dura to bone morphogenetic protein (BMP) in repair of skull defects", Ann Surg, vol. 196, No. 1, pp. 100-109. Abstract only (1982).
Takami et al., "$Ca^{2+}$-ATPase Inhibitors and $Ca^{2+}$-Ionophore Induce Osteoclast-like Cell Formation in the Cocultures of Mouse Bone Marrow Cells and Calvarial Cells", Biochemical and Biophysical Research Comm., vol. 237, pp. 111-115 (1997).
Tieu et al., "Identification of Human NEL-2 Associated with Premature Suture Fusion", J. Dent res. 77(A):635, Abstract Only (1998).
Ting et al., "Human NELL-1 Expressed in Unilateral Coronal Synostosis", Journal of Bone and Mineral Research, vol. 14, No. 1, pp. 80-89 (1999).
Ting et al., "NELL 1 Enhances Mineralization in Fetal Calvarial Osteoblastic Cells", J. Dent. Res. 79, p. 625, 3849, Abstract Only (2000).
Ting, K. et al. "NEL-2 Expressed in Unilateral Prematurely Fusing and Fused Coronal Sutures", J. Dent Res. 77(B): 2224, Abstract Only (1998).
Ting et al. "NEL-2 Gene is associated with bone formation in Craniosynostosis", Plastic Surgery, Surgical Forum 602-603 (no date).
Toriumi et al. "Mandibular Reconstruction With a Recombinant Bone-Inducing Factor." Arch. Otolaryngol. Head Neck Surg. vol. 117: 1101-1112 (1991).
Watanabe et al. "Cloning and Characterization of Two Novel Human cDNAs (NELL1 and NELL2) Encoding Proteins with Six EGF-like Repeats", Genomics 38, pp. 273-276 (1996).
Wobus, "Potential of Embryonic Stem Cells", Molecular Aspects of Medicine 22, pp. 149-164 (2001).
Yasko et al. "The Healing of Segmental Bone Defects, Induced by Recombinant Human Bone Morphogenetic Protein (rhBMP-2)." J. of Bone and Joint Surgery vol. 74A, No. 5: 659-670 (1992).
Zhang et al., "NELL-1 Overexpression Transgenic Mice Simulate Human Craniosynostosis", Surgical Forum, vol. 52, pp. 576-578 (2001).
Zhang et al., "Craniosynostosis in transgenic Mice Overexpressing Nell-1", The Journal of Clinical Investigation, vol. 110. No. 6 pp. 861-870 (2002).

* cited by examiner

Nell-1

Lac Z

SEQUENCE LISTING

<160> NUMBER OF SEQ ID NOS: 95

<210> SEQ ID NO 1
<211> LENGTH: 3329
<212> TYPE: DNA
<213> ORGANISM: Homo sapiens

<400> SEQUENCE: 1
atatgcgagc gcagcacccg gcgctgccga gccacctccc ccgccgcccg ctagcaagtt 60
tggcggctcc aagccaggcg cgcctcagga tccaggctca tttgcttcca cctagcttcg 120
gtgccccctg ctaggcgggg accctcaaga gcgatgccga tggatttgat tttagttgtg 180
tggttctgtg tgtgcactgc caggacagca gaagatatga agccacccgt gttatcgctg 240
atatggagaa ctagagttct gaagtctctg cttcagcaat cccttcaggg agtggtgggc 300
tttgggatgg accctgacct tcagatggat atcgtcaccg agcttgacct tgtgaacacc 360
acccttggag ttgctcaggt gtctggaatg cacaatgcca gcaaagcatt tttatttcaa 420
gacatagaaa gagagatcca tgcagctcct catgtgagtg agaaattaat tcagctgttc 480
cagaacaaga gtgaattcac cattttggcc actgtacagc agaagccatc cacttcagga 540
gtgatactgt ccattcgaga actggagcac agctattttg aaccggagag cagtggcctg 600
agggatgaga ttcggtatca ctacatacac aatgggaagc caaggacaga ggcacttcct 660
taccgcatgg cagatggaca atggcacaag gttgcactgt cagttagcgc ctctcatctc 720
ctgctccatg tcgactgtaa caggatttat gagcgtgtga tagaccctcc agataccaac 780
cttcccccag gaatcaattt atggcttggc cagcgcaacc aaaagcatgg cttattcaaa 840
gggatcatcc aagatgggaa gatcatcttt atgccgaatg gatatataac acagtgtcca 900
aatctaaatc acacttgccc aacctgcagt gatttcttaa gcctggtgca aggaataatg 960
gatttacaag agcttttggc caagatgact gcaaaactaa attatgcaga gacaagactt 1020
agtcaattgg aaaactgtca ttgtgagaag acttgtcaag tgagtggact gctctatcga 1080
gatcaagact cttgggtaga tggtgaccat tgcaggaact gcacttgcaa aagtggtgcc 1140
gtggaatgcc gaaggatgtc ctgtccccct ctcaattgct ccccagactc cctcccagtg 1200
cacattgctg gccagtgctg taaggtctgc cgaccaaaat gtatctatgg aggaaaagtt 1260
cttgcagaag gccagcggat tttaaccaag agctgtcggg aatgccgagg tggagtttta 1320
gtaaaaatta cagaaatgtg tcctcctttg aactgctcag aaaaggatca cattcttcct 1380
gagaatcagt gctgccgtgt ctgtagaggt cataactttt gtgcagaagg acctaaatgt 1440
ggtgaaaact cagagtgcaa aaactggaat acaaaagcta cttgtgagtg caagagtggt 1500
tacatctctg tccagggaga ctctgcctac tgtgaagata ttgatgagtg tgcagctaag 1560
atgcattact gtcatgccaa tactgtgtgt gtcaaccttc ctgggttata tcgctgtgac 1620
tgtgtcccag gatacattcg tgtggatgac ttctcttgta cagaacacga tgaatgtggc 1680
agcggccagc acaactgtga tgagaatgcc atctgcacca acactgtcca gggacacagc 1740
tgcacctgca aaccgggcta cgtggggaac gggaccatct gcagagcttt ctgtgaagag 1800
ggctgcagat acggtggaac gtgtgtggct cccaacaaat gtgtctgtcc atctggattc 1860
acaggaagcc actgcgagaa agatattgat gaatgttcag agggaatcat tgagtgccac 1920
aaccattccc gctgcgttaa cctgccgggg tggtaccact gtgagtgcag aagcggtttc 1980
catgacgatg ggacctattc actgtccggg gagtcctgta ttgacattga tgaatgtgcc 2040
ttaagaactc acacctgttg gaacgattct gcctgcatca acctggcagg gggttttgac 2100
tgtctctgcc cctctgggcc ctcctgctct ggtgactgtc ctcatgaagg ggggctgaag 2160
cacaatggcc aggtgtggac cttgaaagaa gacaggtgtt ctgtctgctc ctgcaaggat 2220
ggcaagatat tctgccgacg gacagcttgt gattgccaga atccaagtgc tgacctattc 2280
tgttgcccag aatgtgacac cagagtcaca agtcaatgtt tagaccaaaa tggtcacaag 2340
ctgtatcgaa gtggagacaa ttggacccat agctgtcagc agtgtcggtg tctggaagga 2400
gaggtagatt gctggccact cacttgcccc aacttgagct gtgagtatac agctatctta 2460
gaaggggaat gttgtccccg ctgtgtcagt gacccctgcc tagctgataa catcacctat 2520
gacatcagaa aaacttgcct ggacagctat ggtgtttcac ggcttagtgg ctcagtgtgg 2580
acgatggctg gatctccctg cacaacctgt aaatgcaaga atggaagagt ctgttgttct 2640
gtggattttg agtgtcttca aaataattga agtatttaca gtggactcaa cgcagaagaa 2700
tggacgaaat gaccatccaa cgtgattaag gataggaatc ggtagtttgg ttttttttgtt 2760 tgttttgttt ttttaaccac agataattgc caaagtttcc acctgaggac ggtgtttgga 2820
ggttgccttt tggacctacc actttgctca ttcttgctaa cctagtctag gtgacctaca 2880
gtgccgtgca tttaagtcaa tggttgttaa aagaagtttc ccgtgttgta aatcatgttt 2940
cccttatcag atcatttgca aatacattta aatgatctca tggtaaatgt tgatgtattt 3000
tttggtttat tttgtgtact aacataatag agagagactc agctcctttt atttattttg 3060
ttgatttatg gatcaaattc taaaataaag ttgcctgttg tgacttttgt cccatctact 3120
gcatacttag tgctgagatc cctgtaaaat gttttgatga aaatatgtat gtagagtcca 3180
gtcgcattat acatacattt catagtgctg aaccttctta aatgcctact cattcagctt 3240
aaacaggctg aagccaagta tgacaaagag gggaagggcc aaaaacataa tcaaagaata 3300
attttaaaga gaattcttgt ctctcttgc 3329

<210> SEQ ID NO 2
<211> LENGTH: 1907
<212> TYPE: DNA
<213> ORGANISM: Homo sapiens

<400> SEQUENCE: 2
agagagaatt atgacccaag caagaatcat gggtccagaa ttccacccaa ggaagctagt 60
tcaaagccag agaaagagca cagcttttca cacaattgaa tagatctcaa cttcatgatt 120
ttggtattga agatgctgac agtagccagt ggctctgtga aggcaatttt ccaacctacc 180
attcttggct actcctggga tattttactt ggctgtgaga tccccctgag aagcttctct 240
ttttctcaca caattcctcc atcagcgaag tgtggtgggc agcacacagt gactatgatt 300
cctggagatg gcactgggac tgaacttatg ctgcctgtca agattatgtt cagacatctg 360
tgtgtgcctg tggactttga gggaatgtca gtgacctcca cctctgcctc acatgaagag 420
gaaattcata atgccatcat ggcagttcat tgaaaccgtg tggctttgaa gagtagcgtt 480
aaaactgacg acaccctgcc accatcatac aaatccttca acaacatgtt gcataccacc 540
ctagatctct atgccagtgt cattcattta aaaaatttgc caaacgtgga gacctggcac 600
aaagatgtag acatcctagt tgtttgggaa aacacagagg gtgagtatag caatctggag 660
catgagagtg tgaaaggagt gacagagagc ctaaagatca tgactaaggc caagtctttg 720
cgcattgctg aatatgcctt ccagctggcc cagaagatgg gatgcaaaaa agtgatggct 780
gtgcacaagg tcaacatcac gaaactggga gatggtccct tcctccagtg ctgtggggga 840

-continued

```
ggtggcatcc cgctatcctc agctcacctt agaagacatg attgtggaga atgccacaat    900
gcactttctg tgaagagggc tgcagatacg gtggaacgtg tgtggctccc aacaaatgtg    960
tctgtccatc tggattcaca ggaagccact gcgagaaaga tattgatgaa tgttcagagg   1020
gaatcattga gtgccacaac cattcccgct gcgttaacct gccagggtgg taccactgtg   1080
agtgcagaag cggtttccat gacgatggga cctattcact gtccggggag tcctgtattg   1140
gatggcaaga tattctgccg acggacagct tgtgattgcc agaatccaag tgctgaccta   1200
ttctgttgcc cagaatgtga caccagagtc acaagtcaat gtttagacca aaatggtcac   1260
aagctgtatc gaagtggaga caattggacc catagctgtc agcagtgtcg gtgtctggaa   1320
ggagaggtag attgctggcc actcacttgc cccaacttga gctgtgagta tacagctatc   1380
ttagaagggg aatgttgtcc ccgctgtgtc agtgacccct gcctagctga taacatcacc   1440
tatgacatca gaaaaacttg cctggacagc tatggtgttt cacggcttag tggctcagtg   1500
tggacgatgg ctggatctcc ctgcacaacc tgtaaatgca agaatggaag agtctgttgt   1560
tctgtggatt ttgagtgtct tcaaaataat tgaagtattt acagtggact caacgcagaa   1620
gaatggacga aatgaccatc caacgtgatt aaggatagga atcggtagtt tggttttttt   1680
gtttgttttg tttttttaac cacagataat tgccaaagtt tccacctgag gacggtgttt   1740
ggaggttgcc ttttggacct accactttgc tcattcttgc taacctagtc taggtgacct   1800
acagtgccgt gcatttaagt caatggttgt taaaagaagt ttcccgtgtt gtaaatcatg   1860
tttcccttat cagatcattt gcaaatacat ttaaatgatc tcatggt                 1907
```

<210> SEQ ID NO 3
<211> LENGTH: 3026
<212> TYPE: DNA
<213> ORGANISM: Homo sapiens

<400> SEQUENCE: 3

```
ggcgctgccg agccacctcc cccgccgccc gctagcaagt ttggcggctc caagccaggc     60
gcgcctcagg atccaggctc atttgcttcc acctagcttc ggtgccccct gctaggcggg    120
gaccctcgag agcgatgccg atggatttga ttttagttgt gtggttctgt gtgtgcactg    180
ccaggacagt ggtgggcttt gggatggacc ctgaccttca gatggatatc gtcaccgagc    240
ttgaccttgt gaacaccacc cttggagttg ctcaggtgtc tggaatgcac aatgccagca    300
aagcattttt atttcaagac atagaaagag agatccatgc agctcctcat gtgagtgaga    360
aattaattca gctgttccag aacaagagtg aattcaccat tttggccact gtacagcaga    420
agccatccac ttcaggagtg atactgtcca ttcgagaact ggagcacagc tattttgaac    480
tggagagcag tggcctgagg gatgagattc ggtatcacta catacacaat gggaagccaa    540
ggacagaggc acttccttac cgcatggcag atggacaatg gcacaaggtt gcactgtcag    600
ttagcgcctc tcatctcctg ctccatgtcg actgtaacag gatttatgag cgtgtgatag    660
accctccaga taccaacctt cccccaggaa tcaatttatg gcttggccag cgcaaccaaa    720
agcatggctt attcaaaggg atcatccaag atgggaagat catctttatg ccgaatggat    780
atataacaca gtgtccaaat ctaaatcaca cttgcccaac ctgcagtgat ttcttaagcc    840
tggtgcaagg aataatggat ttacaagagc ttttggccaa gatgactgca aaactaaatt    900
atgcagagac aagacttagt caattggaaa actgtcattg tgagaagact tgtcaagtga    960
gtggactgct ctatcgagat caagactctt gggtagatgg tgaccattgc aggaactgca   1020
cttgcaaaag tggtgccgtg gaatgccgaa ggatgtcctg tccccctctc aattgctccc   1080
```

```
cagactccct cccagtgcac attgctggcc agtgctgtaa ggtctgccga ccaaaatgta   1140

tctatggagg aaaagttctt gcagaaggcc agcggatttt aaccaagagc tgtcgggaat   1200

gccgaggtgg agttttagta aaaattacag aaatgtgtcc tcctttgaac tgctcagaaa   1260

aggatcacat tcttcctgag aatcagtgct gccgtgtctg tagaggtcat aacttttgtg   1320

cagaaggacc taaatgtggt gaaaactcag agtgcaaaaa ctggaataca aaagctactt   1380

gtgagtgcaa gagtggttac atctctgtcc agggagactc tgcctactgt gaagatattg   1440

atgagtgtgc agctaagatg cattactgtc atgccaatac tgtgtgtgtc aaccttcctg   1500

ggttatatcg ctgtgactgt gtcccaggat acattcgtgt ggatgacttc tcttgtacag   1560

aacacgatga atgtggcagc ggccagcaca actgtgatga gaatgccatc tgcaccaaca   1620

ctgtccaggg acacagctgc acctgcaaac cgggctacgt ggggaacggg accatctgca   1680

gagctttctg tgaagagggc tgcagatacg gtggaacgtg tgtggctccc aacaaatgtg   1740

tctgtccatc tggattcaca ggaagccact gcgagaaaga tattgatgaa tgttcagagg   1800

gaatcattga gtgccacaac cattcccgct gcgttaacct gccagggtgg taccactgtg   1860

agtgcagaag cggtttccat gacgatggga cctattcact gtccggggag tcctgtattg   1920

acattgatga atgtgcctta agaactcaca cctgttggaa cgattctgcc tgcatcaacc   1980

tggcaggggg ttttgactgt ctctgcccct ctgggccctc ctgctctggt gactgtcctc   2040

atgaaggggg gctgaagcac aatggccagg tgtggacctt gaaagaagac aggtgttctg   2100

tctgctcctg caaggatggc aagatattct gccgacggac agcttgtgat tgccagaatc   2160

caagtgctga cctattctgt tgcccagaat gtgacaccag agtcacaagt caatgtttag   2220

accaaaatgg tcacaagctg tatcgaagtg gagacaattg gacccatagc tgtcagcagt   2280

gtcggtgtct ggaaggagag gtagattgct ggccactcac ttgccccaac ttgagctgtg   2340

agtatacagc tatcttagaa ggggaatgtt gtccccgctg tgtcagtgac ccctgcctag   2400

ctgataacat cacctatgac atcagaaaaa cttgcctgga cagctatggt gtttcacggc   2460

ttagtggctc agtgtggacg atggctggat ctccctgcac aacctgtaaa tgcaagaatg   2520

gaagagtctg ttgttctgtg gattttgagt gtcttcaaaa taattgaagt atttacagtg   2580

gactcaacgc agaagaatgg acgaaatgac catccaacgt gattaaggat aggaatcggt   2640

agtttggttt ttttgtttgt tttgtttttt taaccacaga taattgccaa agtttccacc   2700

tgaggacggt gtttggaggt tgccttttgg acctaccact ttgctcattc ttgctaacct   2760

agtctaggtg acctacagtg ccgtgcattt aagtcaatgg ttgttaaaag aagtttcccg   2820

tgttgtaaat catgtttccc ttatcagatc atttgcaaat acatttaaat gatctcatgg   2880

taaatgttga tgtatttttt ggtttatttt gtgtactaac ataatagaga gagactcagc   2940

tccttttatt tattttgttg atttatggat caaattctaa aataaagttg cctgttgtga   3000

aaaaaaaaaa aaaaaaaaaa aaaaaa                                        3026
```

<210> SEQ ID NO 4
<211> LENGTH: 2541
<212> TYPE: DNA
<213> ORGANISM: Homo sapiens

<400> SEQUENCE: 4

```
tccaggctca tttgcttcca cctagcttcg gtgccccctg ctaggcgggg accctcgaga     60

gcgatgccga tggatttgat tttagttgtg tggttctgtg tgtgcactgc caggacagtg    120
```

-continued

```
gtgggctttg ggatggaccc tgaccttcag atggatatcg tcaccgagct tgaccttgtg    180
aacaccaccc ttggagttgc tcaggtgtct ggaatgcaca atgccagcaa agcattttta    240
tttcaagaca tagaaagaga gatccatgca gctcctcatg tgagtgagaa attaattcag    300
ctgttccgga acaagagtga attcaccatt ttggccactg tacagcagaa gccatctact    360
tcaggagtga tactgtccat tcgagaactg gagcacagct attttgaact ggagagcagt    420
ggcctgaggg atgagattcg gtatcactac atacacaatg ggaagccaag gacagaggca    480
cttccttacc gcatggcaga tggacaatgg cacaaggttg cactgtcagt tagcgcctct    540
catctcctgc tccatgtcga ctgtaacagg atttatgagc gtgtgataga ccctccagat    600
accaaccttc ccccaggaat caatttatgg cttggccagc gcaaccaaaa gcatggctta    660
ttcaaaggga tcatccaaga tgggaagatc atctttatgc cgaatggata tataacacag    720
tgtccaaatc taaatcacac ttgcccaacc tgcagtgatt tcttaagcct ggtgcaagga    780
ataatggatt tacaagagct tttggccaag atgactgcaa aactaaatta tgcagagaca    840
agacttagtc aattggaaaa ctgtcattgt gagaagactt gtcaagtgag tggactgctc    900
tatcgagatc aagactcttg ggtagatggt gaccattgca ggaactgcac ttgcaaaagt    960
ggtgccgtgg aatgccgaag gatgtcctgt ccccctctca attgctcccc agactccctc   1020
ccagtgcaca ttgctggcca gtgctgtaag gtctgccgac caaaatgtat ctatggagga   1080
aaagttcttg cagaaggcca gcggatttta accaagagct gtcgggaatg ccgaggtgga   1140
gttttagtaa aaattacaga aatgtgtcct cctttgaact gctcagaaaa ggatcacatt   1200
cttcctgaga atcagtgctg ccgtgtctgt agaggtcata acttttgtgc agaaggacct   1260
aaatgtggtg aaaactcaga gtgcaaaaac tggaatacaa aagctacttg tgagtgcaag   1320
agtggttaca tctctgtcca gggagactct gcctactgtg aagatattga tgagtgtgca   1380
gctaagatgc attactgtca tgccaatact gtgtgtgtca accttcctgg gttatatcgc   1440
tgtgactgtg tcccaggata cattcgtgtg gatgacttct cttgtacaga acacgatgaa   1500
tgtggcagcg gccagcacaa ctgtgatgag aatgccatct gcaccaacac tgtccaggga   1560
cacagctgca cctgcaaacc gggctacgtg gggaacggga ccatctgcag agctttctgt   1620
gaagagggct gcagatacgg tggaacgtgt gtggctccca acaaatgtgt ctgtccatct   1680
ggattcacag gaagccactg cgagaaagat attgatgaat gttcagaggg aatcattgag   1740
tgccacaacc attcccgctg cgttaacctg ccagggtggt accactgtga gtgcagaagc   1800
ggtttccatg acgatgggac ctattcactg tccggggagt cctgtattga cattgatgaa   1860
tgtgccttaa gaactcacac ctgttggaac gattctgcct gcatcaacct ggcagggggt   1920
tttgactgtc tctgcccctc tggccctcc tgctctggtg actgtcctca tgaagggggg   1980
ctgaagcaca atggccaggt gtggaccttg aaagaagaca ggtgttctgt ctgctcctgc   2040
aaggatggca agatattctg ccgacggaca gcttgtgatt gccagaatcc aagtgctgac   2100
ctattctgtt gcccagaatg tgacaccaga gtcacaagtc aatgtttaga ccaaaatggt   2160
cacaagctgt atcgaagtgg agacaattgg acccatagct gtcagcagtg tcggtgtctg   2220
gaaggagagg tagattgctg gccactcact tgccccaact tgagctgtga gtatacagct   2280
atcttagaag ggaatgttg tccccgctgt gtcagtgacc cctgcctagc tgataacatc   2340
acctatgaca tcagaaaaac ttgcctggac agctatggtg tttcacggct tagtggctca   2400
gtgtggacga tggctggatc tccctgcaca acctgtaaat gcaagaatgg aagagtctgt   2460
tgttctgtgg attttgagtg tcttcaaaat aattgaagta tttacagtgg actcaacgca   2520
```

gaagaatgga cgaaatgacc a 2541

<210> SEQ ID NO 5
<211> LENGTH: 2400
<212> TYPE: DNA
<213> ORGANISM: Homo sapiens

<400> SEQUENCE: 5
tccaggctca tttgcttcca cctagcttcg gtgccccctg ctaggcgggg accctcgaga 60
gcgatgccga tggatttgat tttagttgtg tggttctgtg tgtgcactgc caggacagtg 120
gtgggctttg ggatggaccc tgaccttcag atggatatcg tcaccgagct tgaccttgtg 180
aacaccaccc ttggagttgc tcaggtgtct ggaatgcaca atgccagcaa agcattttta 240
tttcaagaca tagaaagaga gatccatgca gctcctcatg tgagtgagaa attaattcag 300
ctgttccaga acaagagtga attcaccatt ttggccactg tacagcagaa gccatccact 360
tcaggagtga tactgtccat tcgagaactg gagcacagct attttgaact ggagagcagt 420
ggcctgaggg atgagattcg gtatcactac atacacaatg ggaagccaag gacagaggca 480
cttccttacc gcatggcaga tggacaatgg cacaaggttg cactgtcagt tagcgcctct 540
catctcctgc tccatgtcga ctgtaacagg atttatgagc gtgtgataga ccctccagat 600
accaaccttc ccccaggaat caatttatgg cttggccagc gcaaccaaaa gcatggctta 660
ttcaaaggga tcatccaaga tgggaagatc atctttatgc cgaatggata tataacacag 720
tgtccaaatc taaatcacac ttgcccaacc tgcagtgatt tcttaagcct ggtgcaagga 780
ataatggatt tacaagagct tttggccaag atgactgcaa aactaaatta tgcagagaca 840
agacttagtc aattggaaaa ctgtcattgt gagaagactt gtcaagtgag tggactgctc 900
tatcgagatc aagactcttg ggtagatggt gaccattgca ggaactgcac ttgcaaaagt 960
ggtgccgtgg aatgccgaag gatgtcctgt ccccctctca attgctcccc agactccctc 1020
ccagtgcaca ttgctggcca gtgctgtaag gtctgccgac caaaatgtat ctatggagga 1080
aaagttcttg cagaaggcca gcggatttta accaagagct gtcgggaatg ccgaggtgga 1140
gttttagtaa aaattacaga aatgtgtcct cctttgaact gctcagaaaa ggatcacatt 1200
cttcctgaga atcagtgctg ccgtgtctgt agaggtcata acttttgtgc agaaggacct 1260
aaatgtggtg aaaactcaga gtgcaaaaac tggaatacaa aagctacttg tgagtgcaag 1320
agtggttaca tctctgtcca gggagactct gcctactgtg aagatattga tgagtgtgca 1380
gctaagatgc attactgtca tgccaatact gtgtgtgtca accttcctgg gttatatcgc 1440
tgtgactgtg tcccaggata cattcgtgtg gatgacttct cttgtacaga acacgatgaa 1500
tgtggcagcg gccagcacaa ctgtgatgag aatgccatct gcaccaacac tgtccaggga 1560
cacagctgca cctgcaaacc gggctacgtg gggaacggga ccatctgcag agctttctgt 1620
gaagagggct gcagatacgg tggaacgtgt gtggctccca acaaatgtgt ctgtccatct 1680
ggattcacag gaagccactg cgagaaagac attgatgaat gtgccttaag aactcacacc 1740
tgttggaacg attctgcctg catcaacctg gcagggggtt ttgactgtct ctgcccctct 1800
gggccctcct gctctggtga ctgtcctcat gaagggggc tgaagcacaa tggccaggtg 1860
tggaccttga aagaagacag gtgttctgtc tgctcctgca aggatggcaa gatattctgc 1920
cgacggacag cttgtgattg ccagaatcca agtgctgacc tattctgttg cccagaatgt 1980
gacaccagag tcacaagtca atgtttagac caaaatggtc acaagctgta tcgaagtgga 2040

```
gacaattgga cccatagctg tcagcagtgt cggtgtctgg aaggagaggt agattgctgg   2100

ccactcactt gccccaactt gagctgtgag tatacagcta tcttagaagg ggaatgttgt   2160

ccccgctgtg tcagtgaccc ctgcctagct gataacatca cctatgacat cagaaaaact   2220

tgcctggaca gctatggtgt ttcacggctt agtggctcag tgtggacgat ggctggatct   2280

ccctgcacaa cctgtaaatg caagaatgga agagtctgtt gttctgtgga ttttgagtgt   2340

cttcaaaata attgaagtat ttacagtgga ctcaacgcag aagaatggac gaaatgacca   2400
```

<210> SEQ ID NO 6
<211> LENGTH: 2400
<212> TYPE: DNA
<213> ORGANISM: Homo sapiens

<400> SEQUENCE: 6

```
tccaggctca tttgcttcca cctagcttcg gtgccccctg ctaggcgggg accctcgaga     60

gcgatgccga tggatttgat tttagttgtg tggttctgtg tgtgcactgc caggacagtg    120

gtgggctttg ggatggaccc tgaccttcag atggatatcg tcaccgagct tgaccttgtg    180

aacaccaccc ttggagttgc tcaggtgtct ggaatgcaca atgccagcaa agcatttttta    240

tttcaagaca tagaaagaga gatccatgca gctcctcatg tgagtgagaa attaattcag    300

ctgttccaga acaagagtga attcaccatt ttggccactg tacagcagaa gccatccact    360

tcaggagtga tactgtccat tcgagaactg gagcacagct attttgaact ggagagcagt    420

ggcctgaggg atgagattcg gtatcactac atacacaatg ggaagccaag gacagaggca    480

cttccttacc gcatggcaga tggacaatgg cacaaggttg cactgtcagt tagcgcctct    540

catctcctgc tccatgtcga ctgtaacagg atttatgagc gtgtgataga ccctccagat    600

accaaccttc cccaggaat caatttatgg cttggccagc gcaaccaaaa gcatggctta    660

ttcaaaggga tcatccaaga tgggaagatc atctttatgc cgaatggata tataacacag    720

tgtccaaatc taaatcacac ttgcccaacc tgcagtgatt tcttaagcct ggtgcaagga    780

ataatggatt tacaagagct tttggccaag atgactgcaa aactaaatta tgcagagaca    840

agacttagtc aattggaaaa ctgtcattgt gagaagactt gtcaagtgag tggactgctc    900

tatcgagatc aagactcttg ggtagatggt gaccattgca ggaactgcac ttgcaaaagt    960

ggtgccgtgg aatgccgaag gatgtcctgt ccccctctca attgctcccc agactccctc   1020

ccagtgcaca ttgctggcca gtgctgtaag gtctgccgac caaaatgtat ctatggagga   1080

aaagttcttg cagaaggcca gcggatttta accaagagct gttgggaatg ccgaggtgga   1140

gttttagtaa aaattacaga aatgtgtcct cctttgaact gctcagaaaa ggatcacatt   1200

cttcctgaga atcagtgctg ccgtgtctgt agaggtcata acttttgtgc agaaggacct   1260

aaatgtggtg aaaactcaga gtgcaaaaac tggaatacaa aagctacttg tgagtgcaag   1320

agtggttaca tctctgtcca gggagactct gcctactgtg aagatattga tgagtgtgca   1380

gctaagatgc attactgtca tgccaatact gtgtgtgtca accttcctgg gttatatcgc   1440

tgtgactgtg tcccaggata cattcgtgtg gatgacttct cttgtacaga acacgatgaa   1500

tgtggcagcg gccagcacaa ctgtgatgag aatgccatct gcaccaacac tgtccaggga   1560

cacagctgca cctgcaaacc gggctacgtg gggaacggga ccatctgcag agctttctgt   1620

gaagagggct gcagatacgg tggaacgtgt gtggctccca acaaatgtgt ctgtccatct   1680

ggattcacag gaagccactg cgagaaagac attgatgaat gtgccttaag aactcacacc   1740

tgttggaacg attctgcctg catcaacctg gcagggggtt ttgactgtct ctgcccctct   1800
```

gggccctcct gctctggtga ctgtcctcat gaagggggc tgaagcacaa tggccaggtg 1860
tggaccttga aagaagacag gtgttctgtc tgctcctgca aggatggcaa gatattctgc 1920
cgacggacag cttgtgattg ccagaatcca agtgctgacc tattctgttg cccagaatgt 1980
gacaccagag tcacaagtca atgtttagac caaaatggtc acaagctgta tcgaagtgga 2040
gacaattgga cccatagctg tcagcagtgt cggtgtctgg aaggagaggt agattgctgg 2100
ccactcactt gccccaactt gagctgtgag tatacagcta tcttagaagg ggaatgttgt 2160
ccccgctgtg tcagtgaccc ctgcctagct gataacatca cctatgacat cagaaaaact 2220
tgcctggaca gctatggtgt ttcacggctt agtggctcag tgtggacgat ggctggatct 2280
ccctgcacaa cctgtaaatg caagaatgga agagtctgtt gttctgtgga ttttgagtgt 2340
cttcaaaata attgaagtat ttacagtgga ctcaacgcag aagaatggac gaaatgacca 2400

<210> SEQ ID NO 7
<211> LENGTH: 2541
<212> TYPE: DNA
<213> ORGANISM: Homo sapiens

<400> SEQUENCE: 7
tccaggctca tttgcttcca cctagcttcg gtgccccctg ctaggcgggg accctcgaga 60
gcgatgccga tggatttgat tttagttgtg tggttctgtg tgtgcactgc caggacagtg 120
gtgggctttg ggatggaccc tgaccttcag atggatatcg tcaccgagct tgaccttgtg 180
aacaccaccc ttggagttgc tcaggtgtct ggaatgcaca atgccagcaa agcattttta 240
tttcaagaca tagaaagaga gatccatgca gctcctcatg tgagtgagaa attaattcag 300
ctgttccaga acaagagtga attcaccatt ttggccactg tacagcagaa gccatccact 360
tcaggagtga tactgtccat tcgagaactg gagcacagct attttgaact ggagagcagt 420
ggcctgaggg atgagattcg gtatcactac atacacaatg ggaagccaag gacagaggca 480
cttccttacc gcatggcaga tggacaatgg cacaaggttg cactgtcagt tagcgcctct 540
catctcctgc tccatgtcga ctgtaacagg atttatgagc gtgtgataga ccctccagat 600
accaaccttc ccccaggaat caatttatgg cttggccagc gcaaccaaaa gcatggctta 660
ttcaaaggga tcatccaaga tgggaagatc atctttatgc cgaatggata tataacacag 720
tgtccaaatc taaatcacac ttgcccaacc tgcagtgatt tcttaagcct ggtgcaagga 780
ataatggatt tacaagagct tttggccaag atgactgcaa aactaaatta tgcagagaca 840
agacttagtc aattggaaaa ctgtcattgt gagaagactt gtcaagtgag tggactgctc 900
tatcgagatc aagactcttg ggtagatggt gaccattgca ggaactgcac ttgcaaaagt 960
ggtgccgtgg aatgccgaag gatgtcctgt ccccctctca attgctcccc agactccctc 1020
ccagtgcaca ttgctggcca gtgctgtaag gtctgccgac caaaatgtat ctatggagga 1080
aaagttcttg cagaaggcca gcggatttta accaagagct gtcgggaatg ccgaggtgga 1140
gttttagtaa aaattacaga aatgtgtcct cctttgaact gctcagaaaa ggatcacatt 1200
cttcctgaga atcagtgctg ccgtgtctgt agaggtcata acttttgtgc agaaggacct 1260
aaatgtggtg aaaactcaga gtgcaaaaac tggaatacaa aagctacttg tgagtgcaag 1320
agtggttaca tctctgtcca gggagactct gcctactgtg aagatattga tgagtgtgca 1380
gctaagatgc attactgtca tgccaatact gtgtgtgtca accttcctgg gttatatcgc 1440
tgtgactgtg tcccaggata cattcgtgtg gatgacttct cttgtacaga acacgatgaa 1500

```
tgtggcagcg gccagcacaa ctgtgatgag aatgccatct gcaccaacac tgtccaggga   1560
cacagctgca cctgcaaacc gggctacgtg gggaacggga ccatctgcag agctttctgt   1620
gaagagggct gcagatacgg tggaacgtgt gtggctccca acaaatgtgt ctgtccatct   1680
ggattcacag gaagccactg cgagaaagat attgatgaat gttcagaggg aatcattgag   1740
tgccacaacc attcccgctg cgttaacctg ccagggtggt accactgtga gtgcagaagc   1800
ggtttccatg acgatgggac ctattcactg tccggggagt cctgtattga cattgatgaa   1860
tgtgccttaa gaactcacac ctgttggaac gattctgcct gcatcaacct ggcagggggt   1920
tttgactgtc tctgcccctc tgggccctcc tgctctggtg actgtcctca tgaagggggg   1980
ctgaagcaca atggccaggt gtggaccttg aaagaagaca ggtgttctgt ctgctcctgc   2040
aaggatggca agatattctg ccgacggaca gcttgtgatt gccagaatcc aagtgctgac   2100
ctattctgtt gcccagaatg tgacaccaga gtcacaagtc aatgtttaga ccaaaatggt   2160
cacaagctgt atcgaagtgg agacaattgg acccatagct gtcagcagtg tcggtgtctg   2220
gaaggagagg tagattgctg gccactcact tgccccaact tgagctgtga gtatacagct   2280
atcttagaag ggaatgttg tccccgctgt gtcagtgacc cctgcctagc tgataacatc   2340
acctatgaca tcagaaaaac ttgcctggac agctatggtg tttcacggct tagtggctca   2400
gtgtggacga tggctggatc tccctgcaca acctgtaaat gcaagaatgg aagagtctgt   2460
tgttctgtgg attttgagtg tcttcaaaat aattgaagta tttacagtgg actcaacgca   2520
gaagaatgga cgaaatgacc a                                             2541
```

```
<210> SEQ ID NO 8
<211> LENGTH: 2932
<212> TYPE: DNA
<213> ORGANISM: Homo sapiens

<400> SEQUENCE: 8

atccaggctc atttgcttcc acctagcttc ggtgcccccct gctaggcggg gaccctcgag    60
agcgatgccg atggatttga ttttagttgt gtggttctgt gtgtgcactg ccaggacagt   120
ggtgggcttt gggatggacc ctgaccttca gatggatatc gtcaccgagc ttgaccttgt   180
gaacaccacc cttggagttg ctcaggtgtc tggaatgcac aatgccagca aagcattttt   240
atttcaagac atagaaagag agatccatgc agctcctcat gtgagtgaga aattaattca   300
gctgttccgg aacaagagtg aattcaccat tttggccact gtacagcaga agccatctac   360
ttcaggagtg atactgtcca ttcgagaact ggagcacagc tattttgaac tggagagcag   420
tggcctgagg gatgagattc ggtatcacta catacacaat gggaagccaa ggacagaggc   480
acttccttac cgcatggcag atggacaatg gcacaaggtt gcactgtcag ttagcgcctc   540
tcatctcctg ctccatgtcg actgtaacag gatttatgag cgtgtgatag accctccaga   600
taccaacctt cccccaggaa tcaatttatg gcttggccag cgcaaccaaa agcatggctt   660
attcaaaggg atcatccaag atgggaagat catctttatg ccgaatggat atataacaca   720
gtgtccaaat ctaaatcaca cttgcccaac ctgcagtgat ttcttaagcc tggtgcaagg   780
aataatggat ttacaagagc ttttggccaa gatgactgca aaactaaatt atgcagagac   840
aagacttagt caattggaaa actgtcattg tgagaagact tgtcaagtga gtggactgct   900
ctatcgagat caagactctt gggtagatgg tgaccattgc aggaactgca cttgcaaaag   960
tggtgccgtg gaatgccgaa ggatgtcctg tccccctctc aattgctccc cagactccct  1020
cccagtgcac attgctggcc agtgctgtaa ggtctgccga ccaaaatgta tctatggagg  1080
```

aaaagttctt gcagaaggcc agcggatttt aaccaagagc tgtcgggaat gccgaggtgg 1140
agttttagta aaaattacag aaatgtgtcc tcctttgaac tgctcagaaa aggatcacat 1200
tcttcctgag aatcagtgct gccgtgtctg tagaggtcat aacttttgtg cagaaggacc 1260
taaatgtggt gaaaactcag agtgcaaaaa ctggaataca aaagctactt gtgagtgcaa 1320
gagtggttac atctctgtcc agggagactc tgcctactgt gaagatattg atgagtgtgc 1380
agctaagatg cattactgtc atgccaatac tgtgtgtgtc aaccttcctg ggttatatcg 1440
ctgtgactgt gtcccaggat acattcgtgt ggatgacttc tcttgtacag aacacgatga 1500
atgtggcagc ggccagcaca actgtgatga gaatgccatc tgcaccaaca ctgtccaggg 1560
acacagctgc acctgcaaac cgggctacgt ggggaacggg accatctgca gagctttctg 1620
tgaagagggc tgcagatacg gtggaacgtg tgtggctccc aacaaatgtg tctgtccatc 1680
tggattcaca ggaagccact gcgagaaaga tattgatgaa tgttcagagg gaatcattga 1740
gtgccacaac cattcccgct gcgttaacct gccagggtgg taccactgtg agtgcagaag 1800
cggtttccat gacgatggga cctattcact gtccggggag tcctgtattg acattgatga 1860
atgtgcctta agaactcaca cctgttggaa cgattctgcc tgcatcaacc tggcaggggg 1920
ttttgactgt ctctgcccct ctgggccctc ctgctctggt gactgtcctc atgaaggggg 1980
gctgaagcac aatggccagg tgtggacctt gaaagaagac aggtgttctg tctgctcctg 2040
caaggatggc aagatattct gccgacggac agcttgtgat tgccagaatc caagtgctga 2100
cctattctgt tgcccagaat gtgacaccag agtcacaagt caatgtttag accaaaatgg 2160
tcacaagctg tatcgaagtg gagacaattg gacccatagc tgtcagcagt gtcggtgtct 2220
ggaaggagag gtagattgct ggccactcac ttgccccaac ttgagctgtg agtatacagc 2280
tatcttagaa ggggaatgtt gtccccgctg tgtcagtgac ccctgcctag ctgataacat 2340
cacctatgac atcagaaaaa cttgcctgga cagctatggt gtttcacggc ttagtggctc 2400
agtgtggacg atggctggat ctccctgcac aacctgtaaa tgcaagaatg gaagagtctg 2460
ttgttctgtg gattttgagt gtcttcaaaa taattgaagt atttacagtg gactcaacgc 2520
agaagaatgg acgaaatgac catccaacgt gattaaggat aggaatcggt agtttggttt 2580
ttttgtttgt tttgtttttt taaccacaga taattgccaa agtttccacc tgaggacggt 2640
gtttggaggt tgccttttgg acctaccact ttgctcattc ttgctaacct agtctaggtg 2700
acctacagtg ccgtgcattt aagtcaatgg ttgttaaaag aagtttcccg tgttgtaaat 2760
catgtttccc ttatcagatc atttgcaaat acatttaaat gatctcatgg taaatgttga 2820
tgtatttttt ggtttatttt gtgtactaac cataatagag agagactcag ctccttttat 2880
ttattttgtt gatttatgga tcaaattcta aaataaagtt gcctgttgtg ac 2932

<210> SEQ ID NO 9
<211> LENGTH: 3198
<212> TYPE: DNA
<213> ORGANISM: Homo sapiens

<400> SEQUENCE: 9
ttgggaggag cagtctctcc gctcgtctcc cggagctttc tccattgtct ctgcctttac 60
aacagaggga gacgatggac tgagctgatc cgcaccatgg agtctcgggt cttactgaga 120
acattctgtt tgatcttcgg tctcggagca gtttgggggc ttggtgtgga cccttcccta 180
cagattgacg tcttaacaga gttagaactt ggggagtcca cgaccggagt gcgtcaggtc 240

-continued

```
ccggggctgc ataatgggac gaaagccttt ctctttcaag atactcccag aagcataaaa    300
gcatccactg ctacagctga acagtttttt cagaagctga gaaataaaca tgaatttact    360
attttggtga ccctaaaaca gacccactta aattcaggag ttattctctc aattcaccac    420
ttggatcaca ggtacctgga actggaaagt agtggccatc ggaatgaagt cagactgcat    480
taccgctcag gcagtcaccg ccctcacaca gaagtgtttc cttacatttt ggctgatgac    540
aagtggcaca agctctcctt agccatcagt gcttcccatt tgattttaca cattgactgc    600
aataaaattt atgaaagggt agtagaaaag ccctccacag acttgcctct aggcacaaca    660
ttttggctag gacagagaaa taatgcgcat ggatatttta agggtataat gcaagatgtc    720
caattacttg tcatgcccca gggatttatt gctcagtgcc cagatcttaa tcgcacctgt    780
ccaacttgca atgacttcca tggacttgtg cagaaaatca tggagctaca ggatatttta    840
gccaaaacat cagccaagct gtctcgagct gaacagcgaa tgaatagatt ggatcagtgc    900
tattgtgaaa ggacttgcac catgaaggga accacctacc gagaatttga gtcctggata    960
gacggctgta agaactgcac atgcctgaat ggaaccatcc agtgtgaaac tctaatctgc   1020
ccaaatcctg actgcccact taagtcggct cttgcgtatg tggatggcaa atgctgtaag   1080
gaatgcaaat cgatatgcca atttcaagga cgaacctact ttgaaggaga aagaaataca   1140
gtctattcct cttctggagt atgtgttctc tatgagtgca aggaccagac catgaaactt   1200
gttgagagtt caggctgtcc agctttggat tgtccagagt ctcatcagat aaccttgtct   1260
cacagctgtt gcaaagtttg taaaggttat gacttttgtt ctgaaaggca taactgcatg   1320
gagaattcca tctgcagaaa tctgaatgac agggctgttt gtagctgtcg agatggtttt   1380
agggctcttc gagaggataa tgcctactgt gaagacatcg atgagtgtgc tgaagggcgc   1440
cattactgtc gtgaaaatac aatgtgtgtc aacaccccgg gttcttttat gtgcatctgc   1500
aaaactggat acatcagaat tgatgattat tcatgtacag aacatgatga gtgtatcaca   1560
aatcagcaca actgtgatga aaatgcttta tgcttcaaca ctgttggagg acacaactgt   1620
gtttgcaagc cgggctatac agggaatgga acgacatgca aagcattttg caaagatggc   1680
tgtaggaatg gaggagcctg tattgccgct aatgtgtgtg cctgcccaca aggcttcact   1740
ggacccagct gtgaaacgga cattgatgaa tgctctgatg gttttgttca atgtgacagt   1800
cgtgctaatt gcattaacct gcctggatgg taccactgtg agtgcagaga tggctaccat   1860
gacaatggga tgttttcacc aagtggagaa tcgtgtgaag atattgatga gtgtgggacc   1920
gggaggcaca gctgtgccaa tgataccatt tgcttcaatt tggatggcgg atatgattgt   1980
cgatgtcctc atggaaagaa ttgcacaggg gactgcatcc atgatggaaa agttaagcac   2040
aatggtcaga tttgggtgtt ggaaaatgac aggtgctctg tgtgctcatg tcagaatgga   2100
ttcgttatgt gtcgacggat ggtctgtgac tgtgagaatc ccacagttga tcttttttgc   2160
tgccctgaat gtgacccaag gcttagtagt cagtgcctcc atcaaaatgg ggaaactttg   2220
tataacagtg gtgacacctg ggtccagaat tgtcaacagt gccgctgctt gcaaggggaa   2280
gttgattgtt ggcccctgcc ttgcccagat gtggagtgtg aattcagcat tctcccagag   2340
aatgagtgct gcccgcgctg tgtcacagac ccttgccagg ctgacaccat ccgcaatgac   2400
atcaccaaga cttgcctgga cgaaatgaat gtggttcgct tcaccgggtc ctcttggatc   2460
aaacatggca ctgagtgtac tctctgccag tgcaagaatg gccacatctg ttgctcagtg   2520
gatccacagt gccttcagga actgtgaagt taactgtctc atgggagatt tctgttaaaa   2580
gaatgttctt tcattaaaag accaaaaaga agttaaaact taaattgggt gatttgtggg   2640
```

```
cagctaaatg cagctttgtt aatagctgag tgaactttca attatgaaat ttgtggagct   2700
tgacaaaatc acaaaaggaa aattactggg gcaaaattag acctcaagtc tgcctctact   2760
gtgtctcaca tcaccatgta gaagaatggg cgtacagtat ataccgtgac atcctgaacc   2820
ctggatagaa agcctgagcc cattggatct gtgaaagcct ctagcttcac tggtgcagaa   2880
aattttcctc tagatcagaa tcttcagaat cagttaggtt cctcactgca agaaataaaa   2940
tgtcaggcag tgaatgaatt atattttcag aagtaaagca aagaagctat aacatgttat   3000
gtacagtaca ctctgaaaag aaatctgaaa caagttattg taatgataaa aataatgcac   3060
aggcatggtt acttaatatt ttctaacagg aaaagtcatc cctatttcct tgttttactg   3120
cacttaatat tatttggttg aatttgttca gtataagctc gttcttgtgc aaaattaaat   3180
aaatatttct cttacctt                                                 3198
```

<210> SEQ ID NO 10
<211> LENGTH: 706
<212> TYPE: DNA
<213> ORGANISM: Homo sapiens
<220> FEATURE:
<221> NAME/KEY: modified_base
<222> LOCATION: (679)
<223> OTHER INFORMATION: a, c, g, t, unknown or other

<400> SEQUENCE: 10

```
gcacgaggcc aagccaggcg cgcctcagga tccaggctca tttgcttcca cctagcttcg     60
gtgccccctg ctaggcgggg accctcgaga gcgatgccga tggatttgat tttagttgtg    120
tggttctgtg tgtgcactgc caggacagtg gtgggctttg ggatggaccc tgaccttcag    180
atggatatcg tcaccgagct tgaccttgtg aacaccaccc ttggagttgc tcaggtgtct    240
ggaatgcaca atgccagcaa agcattttta tttcaagaca tagaaagaga gatccatgca    300
gctcctcatg tgagtgagaa attaattcag ctgttccgga acaagagtga attcaccatt    360
ttggccactg tacagcagaa gccatctact tcaggagtga tactgtccat tcgagaactg    420
gagcacagct attttgaact ggagagcagt ggcctgaggg atgagattcg gtatcactac    480
atacacaatg ggaagccaag gacagaggca cttccttacc gcatggcaga tggacaatgg    540
cacaaggttg cactgtcagt tagcgcctct catctcctgc tccatgtcga ctgtaacagg    600
atttatgagc gtgtgataga ccctccagat accaaccttc ccccaggaat caatttatgg    660
cttggccagc gcaaccaana gcatggctta ttcaaagggg atcatc                   706
```

<210> SEQ ID NO 11
<211> LENGTH: 2977
<212> TYPE: DNA
<213> ORGANISM: Homo sapiens

<400> SEQUENCE: 11

```
tagcaagttt ggcggctcca agccaggcgc gcctcaggat ccaggctcat ttgcttccac     60
ctagcttcgg tgcccccctgc taggcgggga ccctcgagag cgatgccgat ggatttgatt   120
ttagttgtgt ggttctgtgt gtgcactgcc aggacagtgg tgggctttgg gatggaccct    180
gaccttcaga tggatatcgt caccgagctt gaccttgtga acaccaccct tggagttgct    240
caggtgtctg gaatgcacaa tgccagcaaa gcatttttat ttcaagacat agaaagagag    300
atccatgcag ctcctcatgt gagtgagaaa ttaattcagc tgttccagaa caagagtgaa    360
ttcaccattt tggccactgt acagcagaag ccatccactt caggagtgat actgtccatt    420
```

-continued

```
cgagaactgg agcacagcta ttttgaactg gagagcagtg gcctgaggga tgagattcgg    480
tatcactaca tacacaatgg gaagccaagg acagaggcac ttccttaccg catggcagat    540
ggacaatggc acaaggttgc actgtcagtt agcgcctctc atctcctgct ccatgtcgac    600
tgtaacagga tttatgagcg tgtgatagac cctccagata ccaaccttcc cccaggaatc    660
aatttatggc ttggccagcg caaccaaaag catggcttat tcaaagggat catccaagat    720
gggaagatca tctttatgcc gaatggatat ataacacagt gtccaaatct aaatcacact    780
tgcccaacct gcagtgattt cttaagcctg gtgcaaggaa taatggattt acaagagctt    840
ttggccaaga tgactgcaaa actaaattat gcagagacaa gacttagtca attggaaaac    900
tgtcattgtg agaagacttg tcaagtgagt ggactgctct atcgagatca agactcttgg    960
gtagatggtg accattgcag gaactgcact tgcaaaagtg gtgccgtgga atgccgaagg   1020
atgtcctgtc cccctctcaa ttgctcccca gactccctcc cagtacacat tgctggccag   1080
tgctgtaagg tctgccgacc aaaatgtatc tatggaggaa aagttcttgc agaaggccag   1140
cggattttaa ccaagagctg tcgggaatgc cgaggtggag ttttagtaaa aattacagaa   1200
atgtgtcctc ctttgaactg ctcagaaaag gatcacattc ttcctgagaa tcagtgctgc   1260
cgtgtctgta gaggtcataa cttttgtgca gaaggaccta aatgtggtga aaactcagag   1320
tgcaaaaact ggaatacaaa agctacttgt gagtgcaaga gtggttacat ctctgtccag   1380
ggagactctg cctactgtga agatattgat gagtgtgcag ctaagatgca ttactgtcat   1440
gccaatactg tgtgtgtcaa ccttcctggg ttatatcgct gtgactgtgt cccaggatac   1500
attcgtgtgg atgacttctc ttgtacagaa cacgatgaat gtggcagcgg ccagcacaac   1560
tgtgatgaga atgccatctg caccaacact gtccagggac acagctgcac ctgcaaaccg   1620
ggctacgtgg ggaacgggac catctgcaga gctttctgtg aagagggctg cagatacggt   1680
ggaacgtgtg tggctcccaa caaatgtgtc tgtccatctg gattcacagg aagccactgc   1740
gagaaagata ttgatgaatg ttcagaggga atcattgagt gccacaacca ttcccgctgc   1800
gttaacctgc cagggtggta ccactgtgag tgcagaagcg gtttccatga cgatgggacc   1860
tattcactgt ccggggagtc ctgtattgac attgatgaat gtgccttaag aactcacacc   1920
tgttggaacg attctgcctg catcaacctg gcagggggtt ttgactgtct ctgcccctct   1980
gggccctcct gctctggtga ctgtcctcat gaagggggggc tgaagcacaa tggccaggtg   2040
tggaccttga aagaagacag gtgttctgtc tgctcctgca aggatggcaa gatattctgc   2100
cgacggacag cttgtgattg ccagaatcca agtgctgacc tattctgttg cccagaatgt   2160
gacaccagag tcacaagtca atgtttagac caaaatggtc acaagctgta tcgaagtgga   2220
gacaattgga cccatagctg tcagcagtgt cggtgtctgg aaggagaggt agattgctgg   2280
ccactcactt gccccaactt gagctgtgag tatacagcta tcttagaagg ggaatgttgt   2340
ccccgctgtg tcagtgaccc ctgcctagct gataacatca cctatgacat cagaaaaact   2400
tgcctggaca gctatggtgt ttcacggctt agtggctcag tgtggacgat ggctggatct   2460
ccctgcacaa cctgtaaatg caagaatgga agagtctgtt gttctgtgga ttttgagtgt   2520
cttcaaaata attgaagtat ttacagtgga ctcaacgcag aagaatggac gaaatgacca   2580
tccaacgtga ttaaggatag gaatcggtag tttggttttt ttgtttgttt tgttttttta   2640
accacagata attgccaaag tttccacctg aggacggtgt ttcggaggtt gccttttgga   2700
cctaccactt tgctcattct tgctaaccta gtctaggtga cctacagtgc cgtgcattta   2760
agtcaatggt tgttaaaaga agtttcccgt gttgtaaatc atgtttccct tatcagatca   2820
```

tttgcaaata catttaaatg atctcatggt aaatggttga tgtatttttt gggtttattt 2880
tgtgtactaa ccataataga gagagactca gctcctttta tttattttgt tgatttatgg 2940
atcaaattct aaaataaagt tgcctgttgt gactttt 2977

<210> SEQ ID NO 12
<211> LENGTH: 3198
<212> TYPE: DNA
<213> ORGANISM: Homo sapiens

<400> SEQUENCE: 12
ttgggaggag cagtctctcc gctcgtctcc cggagctttc tccattgtct ctgcctttac 60
aacagaggga gacgatggac tgagctgatc cgcaccatgg agtctcgggt cttactgaga 120
acattctgtt tgatcttcgg tctcggagca gtttgggggc ttggtgtgga cccttcccta 180
cagattgacg tcttaacaga gttagaactt ggggagtcca cgaccggagt gcgtcaggtc 240
ccggggctgc ataatgggac gaaagccttt ctctttcaag atactcccag aagcataaaa 300
gcatccactg ctacagctga acagtttttt cagaagctga gaaataaaca tgaatttact 360
attttggtga ccctaaaaca gacccactta aattcaggag ttattctctc aattcaccac 420
ttggatcaca ggtacctgga actggaaagt agtggccatc ggaatgaagt cagactgcat 480
taccgctcag gcagtcaccg ccctcacaca gaagtgtttc cttacatttt ggctgatgac 540
aagtggcaca agctctcctt agccatcagt gcttcccatt tgattttaca cattgactgc 600
aataaaattt atgaaagggt agtagaaaag ccctccacag acttgcctct aggcacaaca 660
ttttggctag gacagagaaa taatgcgcat ggatatttta agggtataat gcaagatgtc 720
caattacttg tcatgcccca gggatttatt gctcagtgcc cagatcttaa tcgcacctgt 780
ccaacttgca atgacttcca tggacttgtg cagaaaatca tggagctaca ggatatttta 840
gccaaaacat cagccaagct gtctcgagct gaacagcgaa tgaatagatt ggatcagtgc 900
tattgtgaaa ggacttgcac catgaaggga accacctacc gagaatttga gtcctggata 960
gacggctgta agaactgcac atgcctgaat ggaaccatcc agtgtgaaac tctaatctgc 1020
ccaaatcctg actgcccact taagtcggct cttgcgtatg tggatggcaa atgctgtaag 1080
gaatgcaaat cgatatgcca atttcaagga cgaacctact ttgaaggaga aagaaataca 1140
gtctattcct cttctggagt atgtgttctc tatgagtgca aggaccagac catgaaactt 1200
gttgagagtt caggctgtcc agctttggat tgtccagagt ctcatcagat aaccttgtct 1260
cacagctgtt gcaaagtttg taaaggttat gacttttgtt ctgaaaggca taactgcatg 1320
gagaattcca tctgcagaaa tctgaatgac agggctgttt gtagctgtcg agatggtttt 1380
agggctcttc gagaggataa tgcctactgt gaagacatcg atgagtgtgc tgaagggcgc 1440
cattactgtc gtgaaaatac aatgtgtgtc aacaccccgg gttcttttat gtgcatctgc 1500
aaaactggat acatcagaat tgatgattat tcatgtacag aacatgatga gtgtatcaca 1560
aatcagcaca actgtgatga aaatgcttta tgcttcaaca ctgttggagg acacaactgt 1620
gtttgcaagc cgggctatac agggaatgga acgacatgca aagcattttg caaagatggc 1680
tgtaggaatg gaggagcctg tattgccgct aatgtgtgtg cctgcccaca aggcttcact 1740
ggacccagct gtgaaacgga cattgatgaa tgctctgatg gttttgttca atgtgacagt 1800
cgtgctaatt gcattaacct gcctggatgg taccactgtg agtgcagaga tggctaccat 1860
gacaatggga tgttttcacc aagtggagaa tcgtgtgaag atattgatga gtgtgggacc 1920

-continued

```
gggaggcaca gctgtgccaa tgataccatt tgcttcaatt tggatggcgg atatgattgt   1980

cgatgtcctc atggaaagaa ttgcacaggg gactgcatcc atgatggaaa agttaagcac   2040

aatggtcaga tttgggtgtt ggaaaatgac aggtgctctg tgtgctcatg tcagaatgga   2100

ttcgttatgt gtcgacggat ggtctgtgac tgtgagaatc ccacagttga tcttttttgc   2160

tgccctgaat gtgacccaag gcttagtagt cagtgcctcc atcaaaatgg ggaaactttg   2220

tataacagtg gtgacacctg ggtccagaat tgtcaacagt gccgctgctt gcaaggggaa   2280

gttgattgtt ggcccctgcc ttgcccagat gtggagtgtg aattcagcat tctcccagag   2340

aatgagtgct gcccgcgctg tgtcacagac ccttgccagg ctgacaccat ccgcaatgac   2400

atcaccaaga cttgcctgga cgaaatgaat gtggttcgct tcaccgggtc ctcttggatc   2460

aaacatggca ctgagtgtac tctctgccag tgcaagaatg gccacatctg ttgctcagtg   2520

gatccacagt gccttcagga actgtgaagt taactgtctc atgggagatt tctgttaaaa   2580

gaatgttctt tcattaaaag accaaaaaga agttaaaact taaattgggt gatttgtggg   2640

cagctaaatg cagctttgtt aatagctgag tgaactttca attatgaaat ttgtggagct   2700

tgacaaaatc acaaaaggaa aattactggg gcaaaattag acctcaagtc tgcctctact   2760

gtgtctcaca tcaccatgta gaagaatggg cgtacagtat ataccgtgac atcctgaacc   2820

ctggatagaa agcctgagcc cattggatct gtgaaagcct ctagcttcac tggtgcagaa   2880

aattttcctc tagatcagaa tcttcagaat cagttaggtt cctcactgca agaaataaaa   2940

tgtcaggcag tgaatgaatt atattttcag aagtaaagca aagaagctat aacatgttat   3000

gtacagtaca ctctgaaaag aaatctgaaa caagttattg taatgataaa aataatgcac   3060

aggcatggtt acttaatatt ttctaacagg aaaagtcatc cctatttcct tgttttactg   3120

cacttaatat tatttggttg aatttgttca gtataagctc gttcttgtgc aaaattaaat   3180

aaatatttct cttacctt                                                  3198
```

<210> SEQ ID NO 13
<211> LENGTH: 3532
<212> TYPE: DNA
<213> ORGANISM: Homo sapiens

<400> SEQUENCE: 13

```
gctcagttcc ccttgccttc tgctgtatgc tggtcccaga gagcccgagt ccgggtctcc     60

acgctttatt tggcaggggg cgcgcgggtt ccggagctgt ccagcacctc ctggccaagt    120

tctctgcgct ctccgcgccc gggaagctct ccgcgccggg gaagctctcc agcgccccgc    180

ccccggcagg gaacctctcc accaggacac ccggggctcc ccaggctcgc catccgtccc    240

caccagtctc tacctacttt gcccagctcc acctcagcag tgcagcgtgt tttggtggcc    300

ttcctccgca cgccctggag ggggagtgcc ctgcaccccg gggctgctcc ggagcccagt    360

gcacgagtgc acatgggctt ccctcctttg cttaaagggc aggcgagcgc tactcgctcc    420

agccttgcct cctgcagctg ggtggtcttt tttctctcct gtctttcaag acacgcgccc    480

gaaatcgagg ggtgagagca aagaccgccc atcaacttag caccttggat ttagagcttt    540

caatcccgaa aggagaggga gacgatggac tgagctgatc cgcaccatgg agtctcgggt    600

cttactgaga acattctgtt tgatcttcgg tctcggagca gtttgggggc ttggtgtgga    660

cccttcccta cagattgacg tcttaacaga gttagaactt ggggagtcca cgaccggagt    720

gcgtcaggtc ccggggctgc ataatgggac gaaagccttt cactttcagg atactcccag    780

aagcataaaa gcatccactg ctacagctga acagtttttt cagaagctga gaaataaaca    840
```

-continued tgaatttact attttggtga ccctaaaaca gacccactta aattcaggag ttattctctc 900
aattcaccac ttggatcaca ggtacctgga actggaaagt agtggccatc ggaatgaagt 960
cagactgcat taccgctcag gcagtcaccg ccctcacaca gaagtgtttc cttacatttt 1020
ggctgatgac aagtggcaca agctctcctt agccatcagt gcttcccatt tgattttaca 1080
cattgactgc aataaaattt atgaaagggt agtagaaaag ccctccacag acttgcctct 1140
aggcacaaca ttttggctag gacagagaaa taatgcgcat ggatatttta agggtataat 1200
gcaagatgtc caattacttg tcatgcccca gggatttatt gctcagtgcc cagatcttaa 1260
tcgcacctgt ccaacttgca atgacttcca tggacttgtg cagaaaatca tggagctaca 1320
ggatatttta gccaaaacat cagccaagct gtctcgagct gaacagcgaa tgaatagatt 1380
ggatcagtgc tattgtgaaa ggacttgcac catgaaggga accacctacc gagaatttga 1440
gtcctggata gacggctgta agaactgcac atgcctgaat ggaaccatcc agtgtgaaac 1500
tctaatctgc ccaaatcctg actgcccact taagtcggct cttgcgtatg tggatggcaa 1560
atgctgtaag gaatgcaaat cgatatgcca atttcaagga cgaacctact ttgaaggaga 1620
aagaaataca gtctattcct cttctggagt atgtgttctc tatgagtgca aggaccagac 1680
catgaaactt gttgagagtt caggctgtcc agctttggat tgtccagagt ctcatcagat 1740
aaccttgtct cacagctgtt gcaaagtttg taaaggttat gacttttgtt ctgaaaggca 1800
taactgcatg gagaattcca tctgcagaaa tctgaatgac agggctgttt gtagctgtcg 1860
agatggtttt agggctcttc gagaggataa tgcctactgt gaagacatcg atgagtgtgc 1920
tgaagggcgc cattactgtc gtgaaaatac aatgtgtgtc aacaccccgg gttcttttat 1980
gtgcatctgc aaaactggat acatcagaat tgatgattat tcatgtacag aacatgatga 2040
gtgtatcaca aatcagcaca actgtgatga aaatgcttta tgcttcagca ctgttggagg 2100
acacaactgt gtttgcaagc cgggctatac agggaatgga acgacatgca aagcattttg 2160
caaagatggc tgtaggaatg gaggagcctg tattgccgct aatgtgtgtg cctgcccaca 2220
aggcttcact ggacccagct gtgaaacgga cattgatgaa tgctctgatg gttttgttca 2280
atgtgacagt cgtgctaatt gcattaacct gcctggatgg taccactgtg agtgcagaga 2340
tggctaccat gacaatggga tgttttcacc aagtggagaa tcgtgtgaag atattgatga 2400
gtgtgggacc gggaggcaca gctgtgccaa tgataccatt tgcttcaatt tggatggcgg 2460
atatgattgt cgatgtcctc atggaaagaa ttgcacaggg gactgcatcc aaggcttagt 2520
agtcagtgcc tccatcaaaa tggggaaact ttgtataaca gtggtgacac ctgggtccag 2580
aattgtcaac agtgccgctg cttgcaaggg gaagttgatt gttggcccct gccttgccca 2640
gatgtggagt gtgaattcag cattctccca gagaatgagt gctgcccgcg ctgtgtcaca 2700
gacccttgcc aggctgacac catccgcaat gacatcacca agacttgcct ggacgaaatg 2760
aatgtggttc gcttcaccgg gtcctcttgg atcaaacatg gcactgagtg tactctctgc 2820
cagtgcaaga atggccacat ctgttgctca gtggatccac agtgccttca ggaactgtga 2880
agttaactgt ctcatgggag atttctgtta aaagaatgtt ctttcattaa aagaccaaaa 2940
agaagttaaa acttaagttg ggtgatttgt gggcagctaa atgcagcttt gttaatagct 3000
gagtgaactt tcaattatga aatttgtgga gcttgacaaa atcacaaaag gaaaattact 3060
ggggcaaaat tagacctcaa gtctgcctct actgtgtctc acatcaccat gtagaagaat 3120
gggcgtacag tatataccgt gacatcctga accctggata gaaagcctga gcccattgga 3180

```
tctgtgaaag cctctagctt cactggtgca gaaaattttc ctctagatca gaatcttcaa   3240

gaatcagtta ggttcctcac tgcaagaaat aaaatgtcag gcagtgaatg aattatattt   3300

tcagaagtaa agcaaagaag ctataacatg ttatgtacag tacactctga aaagaaatct   3360

gaaacaagtt attgtaatga taaaaataat gcacaggcat ggttacttaa tattttctaa   3420

caggaaaagt catccctatt tccttgtttt actgcactta atattatttg gttgaatttg   3480

ttcagtataa gctcgttctt gtgcaaaact aaataaatat ttctcttacc tt           3532
```

<210> SEQ ID NO 14
<211> LENGTH: 1938
<212> TYPE: DNA
<213> ORGANISM: Homo sapiens

<400> SEQUENCE: 14

```
attgtctctg cctttacaac aggttcgggc ggcggggaag acggggggt gcggggccgc     60

cccagcccgg gctttcttgg ggccgccccc cttctaccgg gtgtgcgagt ctttggctgc    120

ttttattcgg ctcgggagct aattccccga cggagccgcg ccggggcgag tccgacccct    180

ccctccgggc cccctccggg ccgcgctgcc gcctcggccc tgcgtgtggg aatgatgtgc    240

gcattggagg gtctaagttc ttcacgcgcc tggggaggcc tccctttct ttcttaggca     300

accaaagcgt attaatccta ctgatcagta aatccgaggc agcagcagga gagacaaacg    360

ttattttccc gcttgattcc aagaacctct tcgattttta tttttatttt taaagaggga    420

gacgatggac tgagctgatc cgcaccatgg agtctcgggt cttactgaga acattctgtt    480

tgatcttcgg tctcggagca gtttgggggc ttggtgtgga cccttcccta cagattgacg    540

tcttaacaga gttagaactt ggggagtcca cgaccggagt gcgtcaggtc ccggggctgc    600

ataatgggac gaaagccttt ctctttcaag atactcccag aagcataaaa gcatccactg    660

ctacagctga acagtttttt cagaagctga gaaataaaca tgaatttact attttggtga    720

ccctaaaaca gacccactta aattcaggag ttattctctc aattcaccac ttggatcaca    780

ggtacctgga actggaaagt agtggccatc ggaatgaagt cagactgcat taccgctcag    840

gcagtcaccg ccctcacaca gaagtgtttc cttacatttt ggctgatgac aagtggcaca    900

agctctcctt agccatcagt gcttcccatt tgattttaca cattgactgc aataaaattt    960

atgaaagggt agtagaaaag ccctccactg acttgcctct aggcacaaca ttttggctag   1020

gacagagaaa taatgcgcat ggatatttta agggtataat gcaagatgtc caattacttg   1080

tcatgcccca gggatttatt gctcagtgcc cagatcttaa tcgcacctgt ccaacttgca   1140

atgacttcca tggacttgtg cagaaaatca tggagctaca ggatatttta gccaaaacat   1200

cagccaagct gtctcgagct gaacagcgaa tgaatagatt ggatcagtgc tattgtgaaa   1260

ggacttgcac catgaaggga accacctacc gagaatttga gtcctggata gacggctgta   1320

agaactgcac atgcctgaat ggaaccatcc agtgtgaaac tctaatctgc ccaaatcctg   1380

actgcccact taagtcggct cttgcgtatg tggatggcaa atgctgtaag gaatgcaaat   1440

cgatatgcca atttcaagga cgaacctact ttgaaggaga aagaaataca gtctattcct   1500

cttctggagt atgtgttctc tatgagtgca aggaccagac catgaaactt gttgagagtt   1560

caggctgtcc agctttggat tgtccagagt ctcatcagat aaccttgtct cacagctgtt   1620

gcaaagtttg taaaggttat gacttttgtt ctgaaaggca taactgcatg gagaattcca   1680

tctgcagaaa tctgaatgac agggctgttt gtagctgtcg agatggtttt agggctcttc   1740

gagaggataa tgcctactgt gaagacatcg atgagtgtgc tgaagggcgc cattactgtc   1800
```

gtgaaaatac aatgtgtgtc aacaccccgg gttcttttat gtgcatctgc aaaactggat 1860
acatcagaat tgatgattat tcatgtacag gtaaacggtg gctatttgtg aaataaaata 1920
tttttatgtc ttaagttt 1938

<210> SEQ ID NO 15
<211> LENGTH: 3422
<212> TYPE: DNA
<213> ORGANISM: Homo sapiens

<400> SEQUENCE: 15
ccccgacgga gccgcgccgg ggcgagtccg acccctccct ccgggccccc tccgggccgc 60
gctgccgcct cggccctgcg tgtgggaatg atgtgcgcat tggagggtct aagttcttca 120
cgcgcctggg gaggcctccc ttttctttct taggcaacca aagcgtatta atcctactga 180
tcagtaaatc cgaggcagca gcaggagaga caaacgttat tttcccgctt gattccaaga 240
acctcttcga tttttatttt tatttttaaa gagggagacg atggactgag ctgatccgca 300
ccatggagtc tcgggtctta ctgagaacat tctgtttgat cttcggtctc ggagcagttt 360
gggggcttgg tgtggaccct tccctacaga ttgacgtctt aacagagtta gaacttgggg 420
agtccacgac cggagtgcgt caggtcccgg ggctgcataa tgggacgaaa gcctttctct 480
ttcaagatac tcccagaagc ataaaagcat ccactgctac agctgaacag tttttcaga 540 agctgagaaa taaacatgaa tttactattt tggtgaccct aaaacagacc cacttaaatt 600
caggagttat tctctcaatt caccacttgg atcacaggta cctggaactg gaaagtagtg 660
gccatcggaa tgaagtcaga ctgcattacc gctcaggcag tcaccgccct cacacagaag 720
tgtttcctta cattttggct gatgacaagt ggcacaagct ctccttagcc atcagtgctt 780
cccatttgat tttacacatt gactgcaata aaatttatga aagggtagta gaaaagccct 840
ccacagactt gcctctaggc acaacatttt ggctaggaca gagaaataat gcgcatggat 900
attttaaggg tataatgcaa gatgtccaat tacttgtcat gccccaggga tttattgctc 960
agtgcccaga tcttaatcgc acctgtccaa cttgcaatga cttccatgga cttgtgcaga 1020
aaatcatgga gctacaggat attttagcca aaacatcagc caagctgtct cgagctgaac 1080
agcgaatgaa tagattggat cagtgctatt gtgaaaggac ttgcaccatg aagggaacca 1140
cctaccgaga atttgagtcc tggatagacg gctgtaagaa ctgcacatgc ctgaatggaa 1200
ccatccagtg tgaaactcta atctgcccaa atcctgactg cccacttaag tcggctcttg 1260
cgtatgtgga tggcaaatgc tgtaaggaat gcaaatcgat atgccaattt caaggacgaa 1320
cctactttga aggagaaaga aatacagtct attcctcttc tggagtatgt gttctctatg 1380
agtgcaagga ccagaccatg aaacttgttg agagttcagg ctgtccagct ttggattgtc 1440
cagagtctca tcagataacc ttgtctcaca gctgttgcaa agtttgtaaa ggttatgact 1500
tttgttctga aaggcataac tgcatggaga attccatctg cagaaatctg aatgacaggg 1560
ctgtttgtag ctgtcgagat ggttttaggg ctcttcgaga ggataatgcc tactgtgaag 1620
acatcgatga gtgtgctgaa gggcgccatt actgtcgtga aaatacaatg tgtgtcaaca 1680
ccccgggttc ttttatgtgc atctgcaaaa ctggatacat cagaattgat gattattcat 1740
gtacagaaca tgatgagtgt atcacaaatc agcacaactg tgatgaaaat gctttatgct 1800
tcaacactgt tggaggacac aactgtgttt gcaagccggg ctatacaggg aatggaacga 1860
catgcaaagc attttgcaaa gatggctgta ggaatggagg agcctgtatt gccgctaatg 1920

```
tgtgtgcctg cccacaaggc ttcactggac ccagctgtga aacggacatt gatgaatgct   1980
ctgatggttt tgttcaatgt gacagtcgtg ctaattgcat taacctgcct ggatggtacc   2040
actgtgagtg cagagatggc taccatgaca atgggatgtt ttcaccaagt ggagaatcgt   2100
gtgaagatat tgatgagtgt gggaccggga ggcacagctg tgccaatgat accatttgct   2160
tcaatttgga tggcggatat gattgtcgat gtcctcatgg aaagaattgc acaggggact   2220
gcatccatga tggaaaagtt aagcacaatg gtcagatttg ggtgttggaa aatgacaggt   2280
gctctgtgtg ctcatgtcag aatggattcg ttatgtgtcg acggatggtc tgtgactgtg   2340
agaatcccac agttgatctt ttttgctgcc ctgaatgtga cccaaggctt agtagtcagt   2400
gcctccatca aaatggggaa actttgtata acagtggtga cacctgggtc cagaattgtc   2460
aacagtgccg ctgcttgcaa ggggaagttg attgttggcc cctgccttgc ccagatgtgg   2520
agtgtgaatt cagcattctc ccagagaatg agtgctgccc gcgctgtgtc acagaccctt   2580
gccaggctga caccatccgc aatgacatca ccaagacttg cctggacgaa atgaatgtgg   2640
ttcgcttcac cgggtcctct tggatcaaac atggcactga gtgtactctc tgccagtgca   2700
agaatggcca catctgttgc tcagtggatc cacagtgcct tcaggaactg tgaagttaac   2760
tgtctcatgg gagatttctg ttaaaagaat gttctttcat taaaagacca aaaagaagtt   2820
aaaacttaaa ttgggtgatt tgtgggcagc taaatgcagc tttgttaata gctgagtgaa   2880
ctttcaatta tgaaatttgt ggagcttgac aaaatcacaa aaggaaaatt actggggcaa   2940
aattagacct caagtctgcc tctactgtgt ctcacatcac catgtagaag aatgggcgta   3000
cagtatatac cgtgacatcc tgaaccctgg atagaaagcc tgagcccatt ggatctgtga   3060
aagcctctag cttcactggt gcagaaaatt ttcctctaga tcagaatctt caagaatcag   3120
ttaggttcct cactgcaaga aataaaatgt caggcagtga atgaattata ttttcagaag   3180
taaagcaaag aagctataac atgttgtgta cagtacactc tgaaaagaaa tctgaaacaa   3240
gttattgtaa tgataaaaat aatgcacagg catggttact taatattttc taacaggaaa   3300
agtcatccct atttccttgt tttactgcac ttaatattat ttggttgaat ttgttcagta   3360
taagctcgtt cttgtgcaaa attaaataaa tatttctctt accttataaa aaaaaaaaaa   3420
aa                                                                  3422
```

<210> SEQ ID NO 16
<211> LENGTH: 601
<212> TYPE: DNA
<213> ORGANISM: Homo sapiens

<400> SEQUENCE: 16

```
cacgaggggg aaaacggggg ggtgcggggc cgccccagcc cgggctttct tggggccgcc     60
ccccttctac cgggtgtgcg agtctttggc tgcttttatt cggctcggga gctaattccc    120
cgacggagcc gcgccggggc gagtccgacc cctccctccg ggccccctcc gggccgcgct    180
gccgcctcgg ccctgcgtgt gggaatgatg tgcgcattgg agggtctaag ttcttcacgc    240
gcctggggag gcctcccttt tctttcttag gcaaccaaag cgtattaatc ctactgatca    300
gtaaatccga ggcagcagca ggagagacaa acgttatttt cccgcttgat tccaagaacc    360
tcttcgattt ttatttttat ttttaaagag ggagacgatg gactgagctg atccgcacca    420
tggagtctcg ggtcttactg agaacattct gtttgatctt cggtctcgga gcagtttggg    480
ggcttggtgt ggacccttcc ctacagattg acgtcttaac agagttagaa cttggggagt    540
ccacgaccgg agtgcgtcag gtcccggggc tgcataatgg gacgaaagcc tttctctttc    600
```

a 601

<210> SEQ ID NO 17
<211> LENGTH: 2813
<212> TYPE: DNA
<213> ORGANISM: Mus musculus

<400> SEQUENCE: 17
gcgttggtgc gccctgcttg gcggggggcc tccggagcga tgccgatgga tgtgatttta 60
gttttgtggt tctgtgtgtg caccgccagg acagtgctgg gctttgggat ggaccctgac 120
cttcagatgg acatcatcac tgaacttgac cttgtgaaca ccaccctggg cgtcactcag 180
gtggctggac tacacaatgc cagtaaggca tttctgtttc aagatgtaca gagagagatc 240
cactcagccc ctcatgtgag tgagaagctg atccagctat tccggaataa gagtgagttt 300
acctttttgg ctacagtgca gcagaagccg tccacctcag gggtgatact gtcgatccgg 360
gagctggaac acagctattt tgaactggag agcagtggcc caagagaaga gatacgctat 420
cattacatcc atggcggcaa gcccaggact gaggcccttc cctaccgcat ggccgatgga 480
cagtggcaca aggtcgcgct gtctgtgagc gcctctcacc tcctactcca tgtcgactgc 540
aataggattt atgagcgtgt gatagatcct ccggagacca accttcctcc aggaagcaat 600
ctatggcttg ggcaacgtaa tcaaaagcat ggctttttca aaggaatcat ccaagatggc 660
aagatcatct tcatgccgaa cggcttcatc acacagtgcc ccaacctaaa tcgcacttgc 720
ccaacatgca gtgatttcct gagcctggtt caaggaataa tggatttgca agagcttttg 780
gccaagatga ctgcaaaact gaattatgca gagacgagac ttggtcaact ggaaaattgc 840
cactgtgaga agacctgcca agtgagtggg ctgctctaca gggaccaaga ctcctgggta 900
gatggtgaca actgcaggaa ctgcacatgc aaaagtggtg ctgtggagtg ccgaaggatg 960
tcctgtcccc cactcaactg ttccccagac tcacttcctg tgcatatttc tggccaatgt 1020
tgtaaagttt gcagaccaaa atgtatctat ggaggaaaag ttcttgctga gggccagcgg 1080
attttaacca agacctgccg ggaatgtcga ggtggagtct tggtaaaaat cacagaagct 1140
tgccctcctt tgaactgctc agagaaggat catattcttc cggagaacca gtgctgcagg 1200
gtctgccgag gtcataactt ctgtgcagaa gcacctaagt gtggagaaaa ctcggaatgc 1260
aaaaattgga atacaaaagc gacttgtgag tgcaagaatg gatacatctc tgtccagggc 1320
aactctgcat actgtgaaga tatcgatgag tgtgcagcaa agatgcacta ctgtcatgcc 1380
aacacggtgt gtgtcaactt gccggggtta tatcgctgtg actgcatccc aggatacatc 1440
cgtgtggatg acttctcttg tacggagcat gatgattgtg gcagcggaca acacaactgt 1500
gacaaaaatg ccatctgtac caacacagtc cagggacaca gctgtacctg ccagccaggc 1560
tacgtgggaa atggtactgt ctgcaaagca ttctgtgaag agggttgcag atacggaggt 1620
acctgtgtgg cccctaacaa atgtgtctgt ccttctggat tcacaggaag ccactgtgag 1680
aaagatattg atgaatgtgc agagggattc gttgagtgcc acaaccactc ccgctgcgtt 1740
aaccttccag ggtggtacca ctgtgagtgc agaagcggtt tccatgacga tgggacctat 1800
tcactgtccg gggagtcctg cattgatatt gatgaatgtg ccttaagaac tcacacttgt 1860
tggaatgact ctgcctgcat caacttagca ggaggatttg actgcctgtg tccctctggg 1920
ccctcctgct ctggtgactg tccccacgaa ggggggctga agcataatgg gcaggtgtgg 1980
attctgagag aagacaggtg ttcagtctgt tcctgtaagg atgggaagat attctgccgg 2040

```
cggacagctt gtgattgcca gaatccaaat gttgaccttt tctgctgccc agagtgtgac   2100
accagggtca ctagccaatg tttagatcaa agcggacaga agctctatcg aagtggagac   2160
aactggaccc acagctgcca gcagtgccga tgtctggaag gagaggcaga ctgctggcct   2220
ctagcttgcc ctagtttgag ctgtgaatac acagccatct ttgaaggaga gtgttgtccc   2280
cgctgtgtca gtgacccctg cctggctgat aatattgcct atgacatcag aaaaacttgc   2340
ctggacagct ctggtatttc gaggctgagc ggcgcagtgt ggacaatggc tggatctccc   2400
tgtacaacct gtcaatgcaa gaatgggaga gtctgctgct ctgtggatct ggtgtgtctt   2460
gagaataact gaagatttta aatggactca tcacatgaga aaatggacaa aatgaccatc   2520
taacctgagg aagaggaggg gctgatttct tttctttttt aaccacagtc aattaccaaa   2580
gtctccatca gaggaaggcg tttgggttgc ctttaccact ttgctcatcc ttgctgacct   2640
agtctagatg cctgcagtac cgtgtatttc ggtcgatggt tgttgagtct ccgtgctgta   2700
aatcacattc cccttgtcag atcatttaca gatacattta aaggattcca tgataaatgt   2760
taaagtacct tttgtttatt ttgtgtactg acataataga gacttggcac caa          2813
```

<210> SEQ ID NO 18
<211> LENGTH: 2813
<212> TYPE: DNA
<213> ORGANISM: Mus musculus

<400> SEQUENCE: 18

```
gcgttggtgc gccctgcttg gcgggggcc tccggagcga tgccgatgga tgtgatttta     60
gttttgtggt tctgtgtgtg caccgccagg acagtgctgg gctttgggat ggaccctgac    120
cttcagatgg acatcatcac tgaacttgac cttgtgaaca ccaccctggg cgtcactcag    180
gtggctggac tacacaatgc cagtaaggca tttctgtttc aagatgtaca gagagagatc    240
cactcagccc ctcatgtgag tgagaagctg atccagctat tccggaataa gagtgagttt    300
acctttttgg ctacagtgca gcagaagccg tccacctcag ggtgatact gtcgatccgg     360
gagctggaac acagctattt tgaactggag agcagtggcc caagagaaga gatacgctat    420
cattacatcc atggcggcaa gcccaggact gaggcccttc cctaccgcat ggccgatgga    480
cagtggcaca aggtcgcgct gtctgtgagc gcctctcacc tcctactcca tgtcgactgc    540
aataggattt atgagcgtgt gatagatcct ccggagacca accttcctcc aggaagcaat    600
ctatggcttg ggcaacgtaa tcaaaagcat ggctttttca aaggaatcat ccaagatggc    660
aagatcatct tcatgccgaa cggcttcatc acacagtgcc ccaacctaaa tcgcacttgc    720
ccaacatgca gtgatttcct gagcctggtt caaggaataa tggatttgca agagcttttg    780
gccaagatga ctgcaaaact gaattatgca gagacgagac ttggtcaact ggaaaattgc    840
cactgtgaga agacctgcca agtgagtggg ctgctctaca gggaccaaga ctcctgggta    900
gatggtgaca actgcaggaa ctgcacatgc aaaagtggtg ctgtggagtg ccgaaggatg    960
tcctgtcccc cactcaactg ttccccagac tcacttcctg tgcatatttc tggccaatgt   1020
tgtaaagttt gcagaccaaa atgtatctat ggaggaaaag ttcttgctga gggccagcgg   1080
attttaacca agacctgccg ggaatgtcga ggtggagtct tggtaaaaat cacagaagct   1140
tgccctcctt tgaactgctc agagaaggat catattcttc cggagaacca gtgctgcagg   1200
gtctgccgag gtcataactt ctgtgcagaa gcacctaagt gtggagaaaa ctcggaatgc   1260
aaaaattgga atacaaaagc gacttgtgag tgcaagaatg gatacatctc tgtccagggc   1320
aactctgcat actgtgaaga tatcgatgag tgtgcagcaa agatgcacta ctgtcatgcc   1380
```

```
aacacggtgt gtgtcaactt gccggggtta tatcgctgtg actgcatccc aggatacatc   1440
cgtgtggatg acttctcttg tacggagcat gatgattgtg gcagcggaca acacaactgt   1500
gacaaaaatg ccatctgtac caacacagtc cagggacaca gctgtacctg ccagccaggc   1560
tacgtgggaa atggtactgt ctgcaaagca ttctgtgaag agggttgcag atacggaggt   1620
acctgtgtgg cccctaacaa atgtgtctgt ccttctggat tcacaggaag ccactgtgag   1680
aaagatattg atgaatgtgc agagggattc gttgagtgcc acaaccactc ccgctgcgtt   1740
aaccttccag ggtggtacca ctgtgagtgc agaagcggtt tccatgacga tgggacctat   1800
tcactgtccg gggagtcctg cattgatatt gatgaatgtg ccttaagaac tcacacttgt   1860
tggaatgact ctgcctgcat caacttagca ggaggatttg actgcctgtg tccctctggg   1920
ccctcctgct ctggtgactg tccccacgaa ggggggctga agcataatgg gcaggtgtgg   1980
attctgagag aagacaggtg ttcagtctgt tcctgtaagg atgggaagat attctgccgg   2040
cggacagctt gtgattgcca gaatccaaat gttgaccttt tctgctgccc agagtgtgac   2100
accagggtca ctagccaatg tttagatcaa agcggacaga agctctatcg aagtggagac   2160
aactggaccc acagctgcca gcagtgccga tgtctggaag gagaggcaga ctgctggcct   2220
ctagcttgcc ctagtttgag ctgtgaatac acagccatct ttgaaggaga gtgttgtccc   2280
cgctgtgtca gtgacccctg cctggctgat aatattgcct atgacatcag aaaaacttgc   2340
ctggacagct ctggtatttc gaggctgagc ggcgcagtgt ggacaatggc tggatctccc   2400
tgtacaacct gtcaatgcaa gaatgggaga gtctgctgct ctgtggatct ggtgtgtctt   2460
gagaataact gaagatttta aatggactca tcacatgaga aaatggacaa aatgaccatc   2520
taacctgagg aagaggaggg gctgatttct ttttcttttt aaccacagtc aattaccaaa   2580
gtctccatca gaggaaggcg tttgggttgc ctttaccact ttgctcatcc ttgctgacct   2640
agtctagatg cctgcagtac cgtgtatttc ggtcgatggt tgttgagtct ccgtgctgta   2700
aatcacattc cccttgtcag atcatttaca gatacattta aaggattcca tgataaatgt   2760
taaagtacct tttgtttatt ttgtgtactg acataataga gacttggcac caa          2813
```

<210> SEQ ID NO 19
<211> LENGTH: 4107
<212> TYPE: DNA
<213> ORGANISM: Mus musculus

<400> SEQUENCE: 19

```
ttcatgccga acggcttcat cacacagtgc cccaacctaa atcgcacttg cccaacatgc     60
agtgatttcc tgagcctggt tcaaggaata atggatttgc aagagctttt ggccaagatg    120
actgcaaaac tgaattatgc agagacgaga cttggtcaac tggaaaattg ccactgtgag    180
aagacctgcc aagtgagtgg gctgctctac agggaccaag actcctgggt agatggtgac    240
aactgcagga actgcacatg caaaagtggt gctgtggagt gccgaaggat gtcctgtccc    300
ccactcaact gttccccaga ctcacttcct gtgcatattt ctggccaatg ttgtaaagtt    360
tgcagaccaa aatgtatcta tggaggaaaa gttcttgctg agggccagcg gattttaacc    420
aagacctgcc gggaatgtcg aggtggagtc ttggtaaaaa tcacagaagc ttgccctcct    480
ttgaactgct cagagaagga tcatattctt ccggagaacc agtgctgggg tctgccgagg    540
tcataacttc tgtgcagaag cacctaagtg tggagaaaac tcggaatgca aaaattggaa    600
tacaaaagcg acttgtgagt gcaagaatgg atacatctct gtccagggca actctgcata    660
```

-continued

```
ctgtgaagat atcgatgagt gtgcagcaaa gatgcactac tgtcatgcca acacggtgtg    720
tgtcaacttg ccggggttat atcgctgtga ctgcatccca ggatacatcc gtgtggatga    780
cttctcttgt acggagcatg atgattgtgg cagcggacaa cacaactgtg acaaaaatgc    840
catctgtacc aacacagtcc agggacacag ctgtacctgc cagccaggct acgtgggaaa    900
tggtactgtc tgcaaagcat tctgtgaaga gggttgcaga tacggaggta cctgtgtggc    960
ccctaacaaa tgtgtctgtc cttctggatt cacaggaagc cactgtgaga aagatattga   1020
tgaatgtgca gagggattcg ttgagtgcca caaccactcc cgctgcgtta accttccagg   1080
gtggtaccac tgtgagtgca gaagcggttt ccatgacgat gggacctatt cactgtccgg   1140
ggagtcctgc attgatattg atgaatgtgc cttaagaact cacacttgtt ggaatgactc   1200
tgcctgcatc aacttagcag gaggatttga ctgcctgtgt ccctctgggc cctcctgctc   1260
tggtgactgt ccccacgaag gggggctgaa gcataatggg caggtgtgga ttctgagaga   1320
agacaggtgt tcagtctgtt cctgtaagga tgggaagata ttctgccggc ggacagcttg   1380
tgattgccag aatccaaatg ttgacctttt ctgctgccca gagtgtgaca ccagggtcac   1440
tagccaatgt ttagatcaaa gcggacagaa gctctatcga agtggagaca actggaccca   1500
cagctgccag cagtgccgat gtctggaagg agaggcagac tgctggcctc tagcttgccc   1560
tagtttgagc tgtgaataca cagccatctt tgaaggagag tgttgtcccc gctgtgtcag   1620
tgacccctgc ctggctgata atattgccta tgacatcaga aaaacttgcc tggacagctc   1680
tggtatttcg aggctgagcg gcgcagtgtg gacaatggct ggatctccct gtacaacctg   1740
tcaatgcaag aatgggagag tctgctgctc tgtggatctg gtgtgtcttg agaataactg   1800
aagattttaa atggactcat cacatgagaa aatggacaaa atgaccatcc aacctgagga   1860
agaggagggg ctgatttctt tttcttttta accacagtca attaccaaag tctccatcag   1920
aggaaggcgt ttgggttgcc tttaccactt tgctcatcct tgctgaccta gtctagatgc   1980
ctgcagtacc gtgtatttcg gtcgatggtt gttgagtctc cgtgctgtaa atcacatttc   2040
ccttgtcaga tcatttacag atacatttaa aggattccat gataaatgtt aaagtacctt   2100
ttgtttattt tgtgtaccaa cataatagag acttggcacc atttatttat ttttcttgat   2160
ttttggatca aattctaaaa ataaagttgc ctgttgtgac ttctatctca tccgctgcac   2220
acagaatggc ggttcctgag ggacgtgttg atggagatgt gtagcatctg tccacagcat   2280
ctttctgttt caaactgttg aacacagatg cccactcact cagctaaaaa ctgcttaggg   2340
caattatgat acactaaagg ggaaaggatg ccagacatca ttaaacatca tttcaaaaag   2400
tactatctcc tccctgttgc aaaaataaat gaagtgacac atttactcac aatgtccaaa   2460
cagtgatatt aaaagcactt cttggcattg gacaccaatt tatgtttata tcagctttac   2520
ataatgctca aaaccagcaa atcactttaa tagtgcttaa taaagtgaaa ttatacaagt   2580
ctcccacata ttatataaac ctgtttggcc attttttta tttttattct tttcagagta   2640
tttggtttat gtcctttgca cctgacagtt aaggtttctg attcctgcgc agtgctgttc   2700
ctctaaggac attgctctat ggataaaggg ggaaagcctt taagacaagt ttggcttggt   2760
gattgctccc acgtcagctg ctccctgctt gctgatttac tgactgattg atcaattcat   2820
tttatttaaa gtatatgaat cttttacctg catgtatgtc tgtgcaccat gtgtgtgtgt   2880
gtggtgcctg tggtgatcag aagaaggtac cctgccccta gaactgaagt tacagatgtt   2940
ggttaactgc cacatgggtg ctgggaatag aagccagatc tctgcaagaa cagcaaatgc   3000
tcttaacaga tgagacagtt ttccagcccc aaacaatgct atatttttaa ggatcagcag   3060
```

-continued

```
ttattaggtt atacaaatga ttacatttca tcagagttga gcatcaaacc ttaggtggta   3120

cttttaagaa gatcatgcat tgccctgaat taagttagtc cctggactgc tcctcagtgc   3180

tcccatatca caaagtccta acttgttaca ccagcaatgc tacaagtaat gtttaaattc   3240

taaatactaa cattattaat ttaaaattat aagttccaaa cactatcatt cactagtatt   3300

ttttccaaca gagataatag ccaatatttt ttgggaaaat ggagtgctct acatgaaacc   3360

gactctatgt gatgaatcac aatgacaaca aattgaatat aacacttggc aaagcccgat   3420

gcaatgtgat aaattacagc acatcatatt ttatctcaat tccttacatg taaccctggg   3480

gtaaagaatt gaaaattacc ctttgaaagc atttatgaca actcaattaa agagaagcct   3540

ttccaatgtt ataaaaacaa agacatttac aggacttgca actgcatcta cagatctctg   3600

cgtgaaacag cgtcctcctg ttcgattagc acctgcccca cacttacatg tcctgaaggc   3660

aagtctggga gttcccacaa aggctaagag actctcaaag ttaacactat tcttttcctc   3720

ctctgtagaa agtctgctga cctctgccac agagaaagta catatgtatg tcttagaact   3780

gtttctccaa gacattatca aaatgccaca attttatttg aattccagtg tattggtttt   3840

tagctgaagt acaatgaaaa tcgatagggc aaagtactta tttttacaaa tgccatcctt   3900

agactcaata ttttcttttc ttcttgaaac ctaatggagt gagtttaatc tggataattt   3960

taaaccatgg tagtctctat caatatggaa tatacatcat ataatacact gggtggcatt   4020

taattgttaa aaacacattg atccattttg tttaaattga acttgttaga tatggctgac   4080

tgatgggata aatgttattt aagcttc                                       4107
```

```
<210> SEQ ID NO 20
<211> LENGTH: 2011
<212> TYPE: DNA
<213> ORGANISM: Mus musculus
<220> FEATURE:
<221> NAME/KEY: modified_base
<222> LOCATION: (722)
<223> OTHER INFORMATION: a, c, g, t, unknown or other

<400> SEQUENCE: 20

tgagtccagg aggcgagcgg aatccgcaca gactcccagg gcaacctgcg ggagtggcgg     60

agccccgcgc tcccgcccta gctcaggggg agcgcagctg cagcagggtt tagggcccca    120

gccccgtgcc accgccaccc gcggtggagg gtgggctggg ggcggggcag tcggggttgc    180

tttcccgggc gccgccgagc cacctcccct gccgcccgct agtaagtttg gccgcttcga    240

gcccacagag ccgcggcttt ctgaagcatt ggtttcttgc tggcgttggt gcgccctgct    300

tggcgggggg cctccggagc gatgccgatg gatgtgattt tagttttgtg gttctgtgtg    360

tgcaccgcca ggacagtgct gggctttggg atggaccctg accttcagat ggacatcatc    420

actgaacttg accttgtgaa caccaccctg ggcgtcactc aggtggctgg actacacaat    480

gccagtaagg catttctgtt tcaagatgta cagagagaga tccactcagc ccctcatgtg    540

agtgagaagc tgatccagct attccggaat aagagtgagt ttaccttttt ggctacagtg    600

cagcagaagc cgtccacctc aggggtgata ctgtcgatcc gggagctgga acacagctat    660

tttgaactgg agagcagtgg cccaagagaa tagatacgct aacaaaacaa ccatggctgc    720

cngcccggta ttgaggccct tccctaccgc atggccgatg gacagtggca caaggtcgcg    780

ctgtctgtga gcgcctttca cctcctactc catgtcgact gcaataggat ttatgagcgt    840

gtgatagatc ctccggagac caaccttcct ccaggaagca atctatggct tgggcaacgt    900
```

```
aatcaaaagc atggcttttt caaaggaatc atccaagatg gcaagatcat cttcatgccg    960

aacggcttca tcacacagtg ccccaaccta aatcgcactt gcccaacatg cagtgatttc   1020

ctgagcctgg ttcaaggaat aatggatttg caagagcttt tggccaagat gactgcaaaa   1080

ctgaattatg cagagacgag acttggtcaa ctggaaaatt gccactgtga gaagacctgc   1140

caagtgagtg ggctgctcta cagggaccaa gactcctggg tagatggtga caactgcagg   1200

aactgcacat gcaaaagtgg tgctgtggag tgccgaagga tgtcctgtcc cccactcaac   1260

tgttccccag actcacttcc tgtgcatatt tctggccaat gttgtaaagt ttgcagacca   1320

aaatgtatct atggaggaaa agttcttgct gagggccagc ggattttaac caagacctgc   1380

cgggaatgtc gaggtggagt cttggtaaaa atcacagaag cttgccctcc tttgaactgc   1440

tcagagaagg atcatattct tccggagaac cagtgctgca gggtctgccg aggtcataac   1500

ttctgtgcag aagcacctaa gtgtggagaa aactcggaat gcaaaaattg gaatacaaaa   1560

gcgacttgtg agtgcaagaa tggatacatc tctgtccagg gcaactctgc atactgtgaa   1620

ggtaaggtca gccaggtctt gtggggaagt ggtagagaag tttatttcca gttactacag   1680

atatggattt ggctatgcaa gggcatcagt tctcatggtt tatccagcag cttcatgtga   1740

gaaactaagg gctgtgtgag atcataccgt ctccccactg tccacaccaa caccagggta   1800

accacaagca caacactttc attctaacga ttggagggga gaatcatctc caaggtcatc   1860

atgggatgtg gcaaatgagt tccctttaa aataagggat cagacattgg cttagaccca    1920

gatttcatct tcaattcctg aaggcagaat tattttttca gttgatttcc tcaaaggatg   1980

attcgtgagc tgtcactttc tggtcattat c                                  2011
```

<210> SEQ ID NO 21
<211> LENGTH: 294
<212> TYPE: DNA
<213> ORGANISM: Mus musculus

<400> SEQUENCE: 21

```
tcttcatcag aagcaggtgt ctgggacccc tacaccactt tgctcatcct tgccgacctc     60

gtcaagaatc ctcctgtacc gcgtatttcg ctcgatggtt gttgagtctc cgtgctctaa    120

atcacatttc ccttatcaga tcatttatag atacatttaa aggattccat gataaatgtt    180

taagtacctt tcgtttattt tgtgtaccca catcatagag acttggcacc atttatttat    240

ttttcttgat ttttggatca aattctaaaa ataaagttgc ctcttgtgac ttct          294
```

<210> SEQ ID NO 22
<211> LENGTH: 296
<212> TYPE: DNA
<213> ORGANISM: Mus musculus

<400> SEQUENCE: 22

```
atatttacta cttgtttccc tcaacctccc ttacccctcc tcaccactct cctcccctcc     60

taacccactc tagatgcctc cactccctca aattcgtcga tttcgttgat ctccgtcctt    120

aaatcacatt tccctttca gatcatttac agatacattt aaaggattcc atgatacatg     180

ttaaagtacc ttttgtttat tttgtgtacc aacataatag agacttggca ccatttattt    240

atttttcttg atttttggat caaattctaa aaataaagtt ccctgttgtg actccc        296
```

<210> SEQ ID NO 23
<211> LENGTH: 235
<212> TYPE: DNA
<213> ORGANISM: Mus musculus

<400> SEQUENCE: 23
ttgacccgta cactccccct atttcgctcg atgatttcag attctccctt ctttcattca 60
caattccctt ctcagttcat ttacagatac atttaaagga ttccatgata attgttaaag 120
taccttttgt ttattttctg taccaacata atagagactt gccaccattt atttattttt 180
cttgattttt ggatcatatt ctaaaaataa acttccctgt tgtgacttct atctc 235

<210> SEQ ID NO 24
<211> LENGTH: 287
<212> TYPE: DNA
<213> ORGANISM: Mus musculus

<400> SEQUENCE: 24
agtatttgga ttccctatac cactttcttc atccctactc acctcgtcca gatgcctcca 60
gtaccgcgta tttcggtcga tggttctcga ctctccctgc tgtaaatcac atttccctct 120
tcagatcatt tacagataca tttaaaggat tccatgataa atgttaaagt accttttgtt 180
tattttgtgt accaacatca tagagacttg gcaccattta tttatttttc ttgatttttg 240
gatcaaattc taaaaataaa gttccctgtt gtgacttcta tctcatc 287

<210> SEQ ID NO 25
<211> LENGTH: 295
<212> TYPE: DNA
<213> ORGANISM: Mus musculus

<400> SEQUENCE: 25
ccatcacagg acgccgtccg cgtacccttc accactttcc tcatccttgc tgacctcctc 60
tagatgcctg cagtaccgtg tatttcggtc catggttgtt gatctccgtg ctctgaatca 120
catttccctt gtcagatcat ttacagatac atttaaagga ttccatgata aatgttaaag 180
taccttttgt ttattttgtg taccaacatc atagagactt ggcaccattt atttttttctt 240 cttgattttt ggatcaaatt ctaaaaataa agttccctgt tgtgacttct atctc 295

<210> SEQ ID NO 26
<211> LENGTH: 282
<212> TYPE: DNA
<213> ORGANISM: Mus musculus

<400> SEQUENCE: 26
cctttgggtt ccctttacca ctttgctcat ccttcctgac ctagtctaga tccctccagt 60
accgtgtatt tcgatcgatg gttgttgatt ctccgtgctg taaatcacat ttccctttc 120 agatcattta cagatacatt taaaggattc catgataaat gttaaagtac cttttgttta 180
ttttgtgtac caacataata gagacttggc accatttatt tatttttctt gatttttgga 240
tcaaattcta aaaataaagt tccctgttgt gacttctatc tc 282

<210> SEQ ID NO 27
<211> LENGTH: 298
<212> TYPE: DNA
<213> ORGANISM: Mus musculus

<400> SEQUENCE: 27
attaccaaaa tctccatcag aggaagccgt ttgggttccc tttaccactt tgctcatcct 60
tgctgaccta atctagatcc ctccagtacc gtgtatttcc gtcgatggtt gttgagtctc 120
cgtgctgtaa atcacatttc ccttgtcaga tcatttacag atacatttaa aggattccat 180
gataaatgtt aaagtacctt ttgtttattt tgtgtaccaa cataatagag acttggcacc 240
atttatttat ttttcttgat ttttggatca aattctaaaa ataaagttcc ctgttgtg 298

<210> SEQ ID NO 28
<211> LENGTH: 295
<212> TYPE: DNA
<213> ORGANISM: Mus musculus

<400> SEQUENCE: 28
attctccatc agagggagcc ttatgcgttc cctttaccac tttactcatc cttcctgacc 60
taatctagat ccctgcagtc ccctgtattt cggtcgatgg tcgttgagtc tccctgctgt 120
agttcacatt tcccttgtca gatcatttac agacacattt aaaggattcc atgatagatg 180
ttaaagtacc ttttgtttat tttgtgtacc aacataatag agacttggca ccatttattt 240
atttttcttg atttttggat caaattctaa aaataaagtt ccctgttgtg acttc 295

<210> SEQ ID NO 29
<211> LENGTH: 302
<212> TYPE: DNA
<213> ORGANISM: Mus musculus

<400> SEQUENCE: 29
ccaatttcca tcagaggccc cgtctgggtc gcctttacca ccttgctctt ccttgctgac 60
ctagtctaga tgcctccagt accgtgcatt tcggtcgatg gttgttgact ctccctcctg 120
taattcacat ttcccttctc agatcattta cagatacatt taaaggattc catgataaat 180
gttaaagtac cttttgttta ttttgtgtac caacataata gagacttggc accatttatt 240
tatttttctt gatttttgga tcaaattcta aaaataaagt tccctgttgt gacttctatc 300
cc 302

<210> SEQ ID NO 30
<211> LENGTH: 274
<212> TYPE: DNA
<213> ORGANISM: Mus musculus
<220> FEATURE:
<221> NAME/KEY: modified_base
<222> LOCATION: (47)
<223> OTHER INFORMATION: a, c, g, t, unknown or other

<400> SEQUENCE: 30
aaggcctttg gcttcccttt accactttgc tcatccttgc tgacctngtc aagatgcctg 60
cagtaccgtg tatttcggtc gatggttgtt gagtttccgt gctgtaaatc acatttccct 120
tgtcagatca tttacagata catttaaagg attccatgat aaatgttaaa gtaccttttg 180
tttattttgt gtaccaacat aatagagact tggcaccatt tatttatttt tcttgatttt 240
tggatcaaat tctaaaaata aagttccctg ttcc 274

<210> SEQ ID NO 31
<211> LENGTH: 284
<212> TYPE: DNA
<213> ORGANISM: Mus musculus

<400> SEQUENCE: 31
gaaggcgttt gggtctcctt caccactttg ctcatccttg ctgacctagt ctagatccct 60
gcagtaccgt gtatttcggt cgatggttgt tgagtctccg tgctgtaaat cacatttccc 120
tagtcagatc atttacagat acatttaaag gattccatga taaatgttaa agtacctttt 180
gtttattttg tgtaccaaca taatagagac ttggcaccat ttatttattt ttcttgattt 240
ttggatcaaa ttctaaaaat aaagtcgcct gttgtgactt ctat 284

<210> SEQ ID NO 32
<211> LENGTH: 298
<212> TYPE: DNA
<213> ORGANISM: Mus musculus

<400> SEQUENCE: 32
attaccaaag tctccatcag aggaaggcgt ttgggttgcc tctaccactt tgctcatcct 60
tgctcacctc gtctagatgc ctgcagtacc gtgtatttcg gtcgatggtt gttgagtctc 120
cgtgctgtaa atcacatttc ccttgtcaca tcatttacag atacatttaa aggattccat 180
gataaatgtt taagtacctt ttgtttattt tgtgtaccaa cattatagag acttggcacc 240
atttatttat ttttcttgat ttttggatca aattctaaaa ataaagttcc ctgttgtg 298

<210> SEQ ID NO 33
<211> LENGTH: 284
<212> TYPE: DNA
<213> ORGANISM: Mus musculus
<220> FEATURE:
<221> NAME/KEY: modified_base
<222> LOCATION: (24)
<223> OTHER INFORMATION: a, c, g, t, unknown or other

<400> SEQUENCE: 33
attagaagaa ggccctctgc gttnccttca ccactttgct tttccttgct aacctagtct 60
agatgcctgc agcaccgtgt atttcgctcg atggttgttg agtttcccta ctgtttatca 120
catttccctc gtcagatcat ttacagatac atttaaagga ttccatgata aatgttaaag 180
taccttttgt ttattttgtg taccaacata atagagactt ggcaccattt atttattttt 240
cttgattttt ggatcaaatt ctaaaaataa agttgcctgt tgtg 284

<210> SEQ ID NO 34
<211> LENGTH: 288
<212> TYPE: DNA
<213> ORGANISM: Mus musculus

<400> SEQUENCE: 34
ggaaacgcct tcggaagcct tcactacttt cctaatcctt cctaacctgt tttagatgcc 60
tccagtaccg tgtatttcgg tggatggtta ttgagtctcc ctcctgtaaa tcacatttcc 120
cttttcagat aatttacaga tacatttaaa ggattccatg ataaatgtta aagtaccttt 180
tgtttatttt gtgtaccaac ataatagaga cttggcacca tttatttatt tttcttgatt 240
tttggatcaa attctaaaaa taaagttgcc tgttgtgact tctatttc 288

<210> SEQ ID NO 35
<211> LENGTH: 281
<212> TYPE: DNA
<213> ORGANISM: Mus musculus

<400> SEQUENCE: 35
tcagaggaag cttttgggtc ccctttacca atttcctaat ctattctgac ctcgtctaga 60
tgcctgcagt accgtgtatt tcggttgatg gttgttgact ctccgtcctg tatatcacat 120
ttccctagtc agatcattta cagatacatt taaaggattc catgataaat gttaaagtac 180
cttttgttta ttttgtgtac caacataata gagacttggc accattcatt tatttttctt 240
gatttttgga tcaaattcta aaaataaagt tgcctgttgt g 281

<210> SEQ ID NO 36
<211> LENGTH: 293
<212> TYPE: DNA
<213> ORGANISM: Mus musculus

<400> SEQUENCE: 36
atcagaggaa ggcgttcggt tcccttaacc actttgctca tccccgctga cctcgtctag 60
atccctgcag taccgtgtat ttcggtcgat ggttgttgag tctccctcct gtaaatcaca 120
tttccctcgt cagatcattc acagatacat ttaaaggatt ccctgataaa tgttaaagta 180
ccttttgttt attttgtgta ccaacatgat agagacttgg caccatttat ttatttttct 240
tgatttttgg atcaaattct aaaaataaag ttccctgttg tgacttctat ccc 293

<210> SEQ ID NO 37
<211> LENGTH: 297
<212> TYPE: DNA
<213> ORGANISM: Mus musculus

<400> SEQUENCE: 37
tccattagag gaaggcgttt gggttgcctt aaccactttg ctcatccttg ctgacctggt 60
ccagatgcct gcagtaccgt gtatttcggt cgatggttgt tgagtctccc tgctgtaaat 120
cacatttccc ttgtcagatc atttacagat acatttaaag gattccatga taaatgttaa 180
agtacctttt gtttattttg tgtaccaaca taatagagac ttggcaccat ttatttattt 240
ttcttgattt ttggatcaaa ttctaaaaat aaagttccct gttgtgactt ctatccc 297

<210> SEQ ID NO 38
<211> LENGTH: 294
<212> TYPE: DNA
<213> ORGANISM: Mus musculus

<400> SEQUENCE: 38
tccatcagac gtggcatacc tgtatccctt accacatatg tcatccttcc tgaccttttt 60
ttgatccctc ctgttcttaa tttcggtcca ttcttgttga ttctccttgc cgtaaatcac 120
atttcccttt cagatcattt acagttacat tttaaggatt ccatgattaa tgtttaagta 180
ccttttgttt attttgtgta ccaacatcat agagacttgg caccatttat ttgttttttt 240
tgatttttgg atcaaattct aaaaataaag ttccctttttg tgacttcttt cccc 294

<210> SEQ ID NO 39
<211> LENGTH: 283
<212> TYPE: DNA
<213> ORGANISM: Mus musculus

<400> SEQUENCE: 39
ggccaattgg tttcattaac cactttccta atctttctcc acttagtatt gattccccca 60
gctcctttat ttccttcgat gcttgttgac tctccgtgct gtaaatcaca tttcccttgt 120
cagatcattt acagatacat ttagaggatt ccatgataaa tgttaaagta ccttttgttt 180
attttgtcta ccaacataat agagacttgc caccatttat ttatttttct tgatttttgg 240
atcaaattct aaaaataaag ttccctgttg tgacttctat ccc 283

<210> SEQ ID NO 40
<211> LENGTH: 243
<212> TYPE: DNA
<213> ORGANISM: Mus musculus

<400> SEQUENCE: 40

```
tccttaccta ctctacatcc ctgcagtacc gatatttcgg tcgatggatg ttgagtctcc     60

gtgctgtaaa tcacatttcc cttatcagat cattcacaga tacatttaaa ggattccatg    120

ataaatgtta aagtaccttt tgtttatttt gtgtaccaac ataatagaga cttggcacca    180

tttatttatt tttcttgatt tttggatcaa attctaaaaa taaagttccc tgttgtgact    240

tct                                                                  243


<210> SEQ ID NO 41
<211> LENGTH: 293
<212> TYPE: DNA
<213> ORGANISM: Mus musculus

<400> SEQUENCE: 41

tcagacgaag gcctatgggt tccctttacc attttgctca tccttcctga cctattttag     60

atgcctgcag taccgtgtat ttcggtcgat ggttgttgag tctccgtgct gtaaatcaca    120

tttcccttgt cagatcattt acagatacat ttaaaggatt ccatgataaa tgttaaagta    180

ccttttgttt attttgtgta ccaacataat agagacttgg caccatttat ttatttttct    240

tgatttttgg atcaaattct aaaaataaag ttgcctgttg tgacttctat ccc          293


<210> SEQ ID NO 42
<211> LENGTH: 234
<212> TYPE: DNA
<213> ORGANISM: Mus musculus
<220> FEATURE:
<221> NAME/KEY: modified_base
<222> LOCATION: (33)
<223> OTHER INFORMATION: a, c, g, t, unknown or other

<400> SEQUENCE: 42

catccctcca gtaccctatt tttcggtcga tgnttgttga gtctccttgc tctagatcac     60

atttcccttg tcagatcatt tacagataca tttcaaggat tccatgataa atgttaaagt    120

accttttgtt tattttgtgt accaacataa tagagacttg gcaccattta tttatttttc    180

ttgatttttg gatcaaattc taaacataaa gttccctgtt gtgacttcta tccc          234


<210> SEQ ID NO 43
<211> LENGTH: 236
<212> TYPE: DNA
<213> ORGANISM: Mus musculus

<400> SEQUENCE: 43

agtctagatc cctccagtac cctgtatttc ggtcgatggt tgttgagtct ccgtcctgta     60

aatcacattt cccttgtcag atcatttaca gatacattta aaggattcca tgataaatgt    120

taaagtacct tttgtttatt ttgtgtacca acataataga gacttggcac catttattta    180

tttttcttga tttttggatc aaattctaaa aataaagttc cctgttgtga cttctg        236


<210> SEQ ID NO 44
<211> LENGTH: 318
<212> TYPE: DNA
<213> ORGANISM: Mus musculus

<400> SEQUENCE: 44

ttaacccctc tcaattacca tattctccct cagaggaagg cgtttgggtt cccttctcca     60

ctttgctctt ccttcctgac ctagtctaga tccctgcagt accgtgtatt tcggtcgatg    120

gttgttgagt ctccgtgctg taaatcacat ttcccttgtc agatcattta cagatacatt    180
```

-continued taaaggattc catgataaat gttaaagtac cttttgttta ttttgtgtac caacataata 240
gagacttggc accatttatt tatttttctt gatttttgga tcaaattcta taaataaagt 300
tccctgttgt gacttccc 318

<210> SEQ ID NO 45
<211> LENGTH: 247
<212> TYPE: DNA
<213> ORGANISM: Mus musculus

<400> SEQUENCE: 45
ctgacctagt atagatccct gcagcaccct gtacttcggt cgatcgtcgt tgagtctccc 60
tcctgtaaat cacatttccc ttctcagatc atttacagat acatttaaag gattccatga 120
taaatgttaa agtacctttt gtttattttg tgtaccaaca taatagagac ttggcaccat 180
ttatttattt ttcttgattt ttggatcaaa ttcttaaaat aaagttgcct gttgtgactt 240
ctatccc 247

<210> SEQ ID NO 46
<211> LENGTH: 310
<212> TYPE: DNA
<213> ORGANISM: Mus musculus

<400> SEQUENCE: 46
ttttttaacc acatcgctta ccaatttcca tcagaggaag gctttgcgtt ccctttacca 60
ctttgctcat ccttgctgac ctagtctaga tgcctccagt accctctatt tcggtcgatg 120
gttgttgatt ctccgtgctc taaatcacat ttcccttgtc agatcattta cagatacatt 180
taaaggattc catgataaat gttaaagtac cttttgttta ttttgtgtac caacataata 240
gagacttggc accatttatt tatttttctt gatttttgga tcaaattcta aaaataaagt 300
tccctgttcc 310

<210> SEQ ID NO 47
<211> LENGTH: 200
<212> TYPE: DNA
<213> ORGANISM: Mus musculus

<400> SEQUENCE: 47
tgttgaatct ccctgcttta aatcacattt cccttctcag atcatttaca gatacattta 60
aaggattcca tgataaatgt taaagtacct tttctttatt ttgtgtacca acataataga 120
gacttggcac catttattta tttttcttga tttttggttc aaattctata aataaagttc 180
cctgttgtga ctttttttccc 200

<210> SEQ ID NO 48
<211> LENGTH: 273
<212> TYPE: DNA
<213> ORGANISM: Mus musculus

<400> SEQUENCE: 48
ctgcttacct ttaccacttt gctcatcctt actgacctac tcttgatgcc tgcactaccg 60
tgtatttcgg tcgatggttg ttgagtttcc gtgctgtaaa tcacatttcc cttgtcagat 120
catttacaga tacatttaaa ggattccatg ataaatgtta aagtaccttt tgtttatttt 180
gtgtaccaac ataatagaga cttgccacca tttatttatt tttcttgatt tttggatcaa 240
attctaaaaa taaagttccc tgttgtgact tct 273

<210> SEQ ID NO 49
<211> LENGTH: 294
<212> TYPE: DNA
<213> ORGANISM: Mus musculus

<400> SEQUENCE: 49
atcagacgaa ggcctttggg ccccctccac cactttcctc atccttgctg acctagtcaa 60
gacgcctgca gtaccgtgta tttcggtcga tggttgttga gtctccgtgc tgtaaatcac 120
atttccctcg tcagatcatt tacagataca tttaaaggat tccatgataa atgttaaagt 180
accttttgtt tattttgtgt accaacataa tagagacttg gcaccattca tttatttttc 240 ttgattttttg gatcaaattc taaaaataaa gttccctgtt gtgacttcta tctc 294

<210> SEQ ID NO 50
<211> LENGTH: 214
<212> TYPE: DNA
<213> ORGANISM: Mus musculus

<400> SEQUENCE: 50
attccatcga ttctcgttca atctccatcc tgtaaatcac atttcccttt tcagatcatt 60
cacacataca ttttaaggat tccatgataa atgttaaagt accttttgtt tattttctgt 120
accaacataa tagagacttg gcaccattca tttatttttc ttgatttttg gatcaaattc 180
taaaaataaa gttccctgtt gtgacttcta tctc 214

<210> SEQ ID NO 51
<211> LENGTH: 323
<212> TYPE: DNA
<213> ORGANISM: Mus musculus

<400> SEQUENCE: 51
tctcaaccac agtctctaac ccaatctcca tcagacgaac acctgtaagt tccctaaacc 60
actctactca tccttgcaga cctcttccag aagccttcat taccgtgtat ttcgctcgat 120
ggttgttgag tttccctgct gtaaatcaca tttccctctt caaatcattt acagacacat 180
ttaaaggatt ccatgataaa tgttaaagta ccttttgttt attttgtgta ccaacataat 240
agagacttgg caccatttat ttatttttct tgatttttgg atcaaattct aaaaataaag 300
ttccctgttg tgacttctat ctc 323

<210> SEQ ID NO 52
<211> LENGTH: 302
<212> TYPE: DNA
<213> ORGANISM: Mus musculus

<400> SEQUENCE: 52
aagtttccat cagaggaagc cctttgggtt gcctttacca ctttgctcat ccttcctgac 60
ctagtctaga tccctgcagt accctgtatt tcggtcgatg gttgttgagt ctccctgctg 120
tagatcacat ttcccttgtc agatcattta cagatacatt taaaggattc catgataaat 180
gttaaagtac cttttgttta ttttgtgtac caacataata gagacttggc accatttatt 240
tatttttctt gatttttgga tcaaattcta aaaataaagt tgcctgttgt gacttctatc 300
tc 302

<210> SEQ ID NO 53
<211> LENGTH: 309
<212> TYPE: DNA
<213> ORGANISM: Mus musculus

<400> SEQUENCE: 53
aatcacccaa attttctatc agaggaaggt tgttctgcgt agcctctagc cactttgctc 60
atccttgttg acctactcta gatgcttcca gtaccgtgta tttcgctcga tggttgttga 120
ttctccgtgc tgtaaatcac atttcccttg tcagatcatt tacagataca tttaaaggat 180
tccatgataa atgttaaagt accttttgtt tattttgtgt accaacataa tagagacttg 240
gcaccattta tttattttc ttgatttttg gatcaaattc tacaaataaa gttgcctgtt 300
gtgacttct 309

<210> SEQ ID NO 54
<211> LENGTH: 287
<212> TYPE: DNA
<213> ORGANISM: Mus musculus

<400> SEQUENCE: 54
cagaggtagg cgtttgggtt cccttcacca ctttgctcat ccttgctgac ctcttctaga 60
tccctgcagt accgtgtatt tcggtcgatg gttgttgagt ctccctgctg taaatcacat 120
ttccctagtc agatcattta cagatacatt taaaggattc catgataaat gttaaagtac 180
cttttgttta ttttgtgtac caacataata gagacttggc accatttatt tatttttctt 240
gatttttgga tcaaattcta aaaataaagt tacctgttgt gacttct 287

<210> SEQ ID NO 55
<211> LENGTH: 299
<212> TYPE: DNA
<213> ORGANISM: Mus musculus

<400> SEQUENCE: 55
caaattctcc ttcagaggaa gccgtttggg ttcccttaac cactttgctc ttccttgctg 60
acctagtcta gatgcctgca gtaccgtgta tttcggtcga tggttgttga ttttccctgc 120
tgtaaatcac atttccctcg tcagatcatt tacagataca tttaaaggat tccatgataa 180
atgttaaagt accttttgtt tattttgtgt accaacataa tagagacttg gcaccattta 240 tttattttc ttgatttttg gatcaaattc taaaaataaa gttccctgtt gtgacttct 299

<210> SEQ ID NO 56
<211> LENGTH: 287
<212> TYPE: DNA
<213> ORGANISM: Mus musculus

<400> SEQUENCE: 56
gaaggcgtta ggtttgccta aaccactttg ctcatccttg ctgaccttgt ccagatccct 60
gcagtaccgt gtatttcggt cgatggttgt tgagtctccg tgctgtaaat cacatttccc 120
tcgtcagatc atttacagat acatttaaag gattccatga taaatgttaa agtacctttt 180
gtttattttg tgtaccaaca taatagagac ttggcaccat ttatttattt ttcttgattt 240
ttggatcaaa ttctaaaaat aaagttccct gttgtgactt ctatctc 287

<210> SEQ ID NO 57
<211> LENGTH: 288
<212> TYPE: DNA
<213> ORGANISM: Mus musculus

<400> SEQUENCE: 57
attcagcttt ccccagactc acttcctgtc catatttctg cccaaagttt taaagtttgc 60
agaccaaaat gtatgaatgg aggaaaactt cttcctgagg cccagcggat tttaaccaag 120

```
acctgccggg aatgtcgagg tggattcttg gtaaaaatca cagaagcttc ccctcctttg    180

aactgctcag agaaggatca tattcttccg gagaaccagt gctgcaggat ctgccgagtt    240

cataacttct gtgcagaagc acctaagtgt ggagaaaact cggaatgc                 288


<210> SEQ ID NO 58
<211> LENGTH: 233
<212> TYPE: DNA
<213> ORGANISM: Mus musculus

<400> SEQUENCE: 58

tgacatactt tagatccttg cagtaccgtt atttcggtcg atggttgttg actttccgtg     60

ctgtaaatca catttccctt ctcagatcat ttacagatac atttaaagga ttccatgata    120

aatgttaaag tacctttttgt ttattttgtg taccaacata atagagactt ggcaccattt    180

atttattttt tttgattttt ggatcaaatt ttaaaaataa agttgcctgt tgt           233


<210> SEQ ID NO 59
<211> LENGTH: 239
<212> TYPE: DNA
<213> ORGANISM: Mus musculus

<400> SEQUENCE: 59

atttagatcc ctccggtacc gtgtatttcg gtcgatggtt gttgagtttc cgtgctgtaa     60

atcacatttc ccttgtcaga tcattcacag atacatttaa aggattccat gataaatgtt    120

aaagtacctt ttgtttattt tgtgtaccaa cataatagag atttggcacc atttatttat    180

ttttttgat ttttggatca aattcttaaa ataaagttgc ctgttgtgac ttctatccc      239


<210> SEQ ID NO 60
<211> LENGTH: 281
<212> TYPE: DNA
<213> ORGANISM: Mus musculus

<400> SEQUENCE: 60

atttgggttc ccttaaccac tttcctcttc cttgctgacc tggtctagat ccctgcagta     60

ccctctattt cggtcgatgg ttgttgattc tccctgctgt aaatcacatt tcccttgtca    120

gatcatttac agatacattt aaaggattcc ctgataaatg ttaaagtacc ttttgtttat    180

tttgtgtacc aacttcatag agacttggca ccatttattt atttttcttg atttttggat    240

caaattctaa aaataaagtt gcctgttgtg acttctatct c                        281


<210> SEQ ID NO 61
<211> LENGTH: 278
<212> TYPE: DNA
<213> ORGANISM: Mus musculus

<400> SEQUENCE: 61

ccccagactc acttcctgtg catatttcag gccgatgttg tgaagtttgc agacccaaat     60

gtatctatgg aggaaaattt cttcctgagg cccagcggat tttaacccag accccccggg    120

aaagtcgagg tggattcttg gtaaaaatca cagaagcttc ccctcctttg aactgctcag    180

agaaggatca tattcttccg gagaaccagt gctccaggtt ctcccgaggt cataacttct    240

gtgcagaagc acctaagtgt ggagaaaact cggaatcc                            278


<210> SEQ ID NO 62
<211> LENGTH: 229
<212> TYPE: DNA
```

<213> ORGANISM: Mus musculus

<400> SEQUENCE: 62
atgcctgcag taccgtgtat ttcggtcgat ggttgttgag tttccgtgct gtaaatcaca 60
tttcccttct cagatcattt acagatacat ttaaaggatt ccatgataaa tgttaaagta 120
ccttttgttt attttgtgta ccaacataat agagacttgg caccatttat ttattttttt 180
tgatttttgg atcaaattct aaaaataaag ttgcctgttg tgacttctg 229

<210> SEQ ID NO 63
<211> LENGTH: 245
<212> TYPE: DNA
<213> ORGANISM: Mus musculus

<400> SEQUENCE: 63
catctccaga cgccacctct accccgtatt tccgtcgatc gttgtagact ttccgtcctc 60
ttaatcacat ttccctcttc agatcattta cagatacatt taaaggattc catgatgaat 120
gttacagtac cttttgttta ttttgtctac caacatcata gagacttggc tccatttatt 180
tatttttctt gatttttgca tcaaattcta aaaataaagt tccctgttgt gacttctatc 240
cccaa 245

<210> SEQ ID NO 64
<211> LENGTH: 289
<212> TYPE: DNA
<213> ORGANISM: Mus musculus

<400> SEQUENCE: 64
agtctccata agaggcaggc ttcgggtagc ctataccact ttgctcgtcc ttgccgacct 60
agtccagatg cccgcagtac cgtgtatttc ggtcgatggt tgttgagtat ccgtgctgta 120
aatcacattt ccctcgtcag atcatttaca gatacattta aaggattcca tgatcaatgt 180
taaagtacct tttgtttatt ttgtgtacca acataataga gacttggcac catttattta 240 tttttttga tttttggatc aaattctaaa aataaagttg cctgttgcg 289

<210> SEQ ID NO 65
<211> LENGTH: 294
<212> TYPE: DNA
<213> ORGANISM: Mus musculus

<400> SEQUENCE: 65
ccattagagg aaggcgttcg ggtactttca ccactttgtc atctctccca acctagtcca 60
gatacctgca ataccgtgta tttcggtcga tgcttgttga ttctccgtct tgtatatcac 120
atttccctcg tcagattatc tagagataca tttaaaggat tccatgataa atgttaaagt 180
accttttgtt tattttgtgt accaacataa tagagactcg gcaccattta tttatttttc 240
ttgatttttg gatcaaattc taaaaataaa gttgcctgtt gtgacttcta tctc 294

<210> SEQ ID NO 66
<211> LENGTH: 311
<212> TYPE: DNA
<213> ORGANISM: Mus musculus

<400> SEQUENCE: 66
caatcaccat aatatccata agaggaaggc gtttggctcc ccttaatcat tttgtttatc 60
cttcctgacc ttttctagat gcctgcagta ccgtgtattt cggtcgatgg ttgttgagtc 120
tccgtgctgt aaatcacatt tccctagtca gatcatttac agatacattt aaaggattcc 180
atgataaatg ttaaagtacc ttttgtttat tttgtgtacc aacataatag agacttggca 240
ccatttattt atttttcttg atttttggat caaattctaa aaataaagtt gcctgttgtg 300
acttctatca c 311

<210> SEQ ID NO 67
<211> LENGTH: 336
<212> TYPE: DNA
<213> ORGANISM: Mus musculus

<400> SEQUENCE: 67
tgacatcttt ttcttttcac ccacatcact aacctatctc cattagagga acccctcggc 60
taccctctac cactctgctc atccttcctg acgctgttct agatgcctgc cagtaccgtg 120
tatttcggtc gatggttgct gattctccgt cctttaaatc acatttccct cctcagatca 180
tttacagata catttcaagg attccatgat aaatgttaaa gtaccttttg tttattttgt 240
gtaccaacat aatagagact tggcaccatt tatttatttt tcttgatttt tggatcaaat 300
tctaaaaata aagttgcctg ttgtgacttc tatcac 336

<210> SEQ ID NO 68
<211> LENGTH: 328
<212> TYPE: DNA
<213> ORGANISM: Mus musculus

<400> SEQUENCE: 68
tcttcttttt tttaaccaca gtccgttacc acattctcct tcagaggaag gcctctgggt 60
cgcctttacc actttgctca tccttgctga ccttgtctag atccctgcag taccgtgtac 120
ttcggtcgat ggttgttgag tctccgtgct gtaaatcaca tttcccttgt cagatcattt 180
acagatacat ttaaaggatt ccatgataca tgttaaagta ccttttgttt attttgttta 240
cccacataat agagacttgg caccatttat ttatttttct tgatttttgg atcaaattct 300
taatataaag ttccctgttg tgacttcg 328

<210> SEQ ID NO 69
<211> LENGTH: 209
<212> TYPE: DNA
<213> ORGANISM: Mus musculus

<400> SEQUENCE: 69
ttttggttga tggttcctga atctccgtgc tgtagatcac atttcccttt tcagttcatt 60
tacagataca tttaaaggat tccatgataa atgttaaagt accttttgtt tattttgtgt 120
accaacataa tagagacttg gcaccattta tttatttttc ttgatttttg gatcaaattc 180
taaaaataaa gttgcctgtt gtgacttct 209

<210> SEQ ID NO 70
<211> LENGTH: 250
<212> TYPE: DNA
<213> ORGANISM: Mus musculus

<400> SEQUENCE: 70
tttatttatc tttaataaca tagtctagat ccctacagta ccgtgtattt cgcttgatgg 60
ttgttgagtc tccgtggtgt aaatcacatt tcccttgtca gatcatttac agaaacattt 120
ataggattcc atgataaatg ttaaagtacc ttttgtttat tttgtgtacc aacataatag 180
agacttggca ccatttattt atttttttg atttttggat caaattttaa aaataaaatt 240
gcctgttgtg 250

<210> SEQ ID NO 71
<211> LENGTH: 265
<212> TYPE: DNA
<213> ORGANISM: Mus musculus

<400> SEQUENCE: 71
accttgctca tccttccaga cttcttctag attcgtccaa ttccacgtat ttcggtcggt 60
ggttgttgac tttccgcgtt gtaaatcact tttccctcgt cagatcattc acagaaacat 120
ttaagggatt ccatgattaa tgttaaagta ccttttgttt attttttgta ccaacataat 180
agagacttgg caccatttat ttatttttct tgatttttgg atcaaattct aaaaataaag 240
ttgcctgttg tgaattcttt cccaa 265

<210> SEQ ID NO 72
<211> LENGTH: 2675
<212> TYPE: DNA
<213> ORGANISM: Mus musculus
<220> FEATURE:
<221> NAME/KEY: modified_base
<222> LOCATION: (684)
<223> OTHER INFORMATION: a, c, g, t, unknown or other

<400> SEQUENCE: 72
gattgtctcc gcctttccaa cagagggaga cgatggactg agacgatgca cgccatggaa 60
tcccgggtgt tactgagaac gttctgcgtg atcctcggcc ttggagcggt ttgggggctt 120
ggtgtggacc cctccctaca gattgacgtc ttaacagagt tagaacttgg ggagtctaca 180
gatggagtgc gccaagtccc gggactgcat aatgggacga aagccttcct cttccaagag 240
tcccccagaa gcataaaggc atccactgct acagctgagc ggtttctcca gaagctgaga 300
aataaacacg agttcacaat cttggtgacc ttaaaacaga tccacttaaa ttcgggagtt 360
atcctctcca tccaccactt ggatcacagg tacctggaac tggaaagcag tggccatcgg 420
aatgagatca gactccacta ccgctctggc actcaccgcc cccacacgga agtgtttcct 480
tatattttgg ctgatgccaa gtggcacaag ctctccttag ccttcagtgc ctctcactta 540
attttacaca tcgactgcaa taagatctat gaacgagtgg tggaaatgcc cttcacagac 600
ttggctctgg gcacaacatt ttggttggga cagagaaata atgcacatgg ctattttaag 660
ggaataatgc aggatgtgca cgtncttgtc atgcctcagg gcttcattgc tcagtgcccg 720
gaccttaatc gaacctgtcc aacatgcaac gacttccatg ggcttgtgca gaaaatcatg 780
gagctgcagg acattttatc aaagacgtca gccaagctgt cccgagctga acaaagaatg 840
aacaggctgg atcagtgcta ctgtgagcgg acatgcactg tgaagggaac cacctaccga 900
gagtctgagt cctggacaga cggctgtaag aactgcacat gcttgaacgg gaccatccag 960
tgcgagactc tggtctgccc tgctcctgac tgccctccta aatcggcccc tgcgtatgtg 1020
gatggcaagt gctgtaagga gtgcaaatca acctgccagt tccagggacg gagctacttt 1080
gagggagaaa ggaacacggc atactcatct tctggaatgt gtgtcttata tgaatgcaag 1140
gatcagacca tgaagcttgt tgagaacatt ggctgcccac ccttagattg tcccgagtct 1200
catcagattg ccttgtctca cagctgctgc aaggtttgta aaggttatga cttctgttct 1260
gagaagcata cctgcatgga gaactcggtc tgcaggaacc tgaacgacag ggttgtgtgc 1320
agctgcaggg atggttttcg ggctctccga gaggacaacg cctactgtga agacattgac 1380
gagtgtgcag aagggcgcca ttactgccgt gagaacacca tgtgtgtgaa tacacctggt 1440
tctttcatgt gtgtctgcaa aactgggtac atcaggatcg acgattactc atgtacagaa 1500
catgatgagt gtctcacaac ccagcacaat tgtgatgaaa acgctttgtg ctttaacact 1560
gttggaggac acaactgtgt ctgcaagcct ggctacaccg ggaatggaac cacgtgcaaa 1620
gctttctgca aagatggctg tagaaacgga ggagcgtgca ttgctgccaa tgtgtgtgcc 1680
tgcccacaag gcttcacggg acccagctgt gagacagaca ttgacgagtg ctctgagggc 1740
tttgttcagt gtgacagccg tgccaactgc atcaacctgc ctgggtggta tcactgtgag 1800
tgcagagacg gctaccatga caatgggatg tttgcgccag gcggagaatc ctgtgaagat 1860
attgacgaat gcgggactgg gaggcacagc tgcaccaacg acaccatttg cttcaacttg 1920
gacgggggat acgattgccg gtgtccccat gggaagaact gcactgggga ctgcgtgcac 1980
gaggggaaag tgaagcacac cggccagatc tgggtgctgg aaaacgacag gtgctccgtg 2040
tgttcctggc agactgggtt tgtcatgtgt cgacggatgg tctgcgactg cgaaaacccc 2100
acagatgacc tttcctgctg ccctgagtgt gacccaaggc tgagcagtca gtgcctgcat 2160
caaaacgggg aaaccgtgta caacagcggc gacacctggg tccaggattg ccgtcagtgc 2220
cgctgcttgc aaggagaagt tgactgttgg cccctggctt gcccagaggt agaatgtgaa 2280
tttagcgtcc ttcctgagaa cgagtgctgc ccacgctgtg tcaccgatcc ttgtcaggcc 2340
gacaccatcc gcaatgacat caccaaaacc tgcctggacg agatgaacgt ggttcgcttc 2400
accgggtctt cctggatcaa gcacggcacg gagtgtaccc tctgccagtg caagaatggc 2460
catttgtgct gctcagtgga tccacagtgc cttcaggagc tgtgaagtta actgcctcat 2520
gggagatatc tgttcaaaga tgttttctca tttcaaaaga ccaaataaat aaataaataa 2580
ataaaaagtg aggtgtggcc agccagatgc aactttgtta gcagctggat agactgatgt 2640
cgattatgga ttcgtggggc ctgaggaaca tctct 2675

<210> SEQ ID NO 73
<211> LENGTH: 3144
<212> TYPE: DNA
<213> ORGANISM: Mus musculus

<400> SEQUENCE: 73
tggactgaga cgatgcacgc catggaatcc cgggtgttac tgagaacgtt ctgcgtgatc 60
ctcgggcttg gagcggtttg ggggcttggt gtggacccct ccctacagat tgacgtctta 120
acagagttag aacttgggga gtctacagat ggagtgcgcc aagtcccggg actgcataat 180
gggacgaaag ccttcctctt ccaagagtcc cccagaagca taaaggcatc cactgctaca 240
gctgagcggt ttttccagaa gctgagaaat aaacacgagt tcacaatctt ggtgaccctg 300
aaacagatcc acttaaattc gggagttatc ctctccatcc accacttgga tcacaggtac 360
ctggaactgg aaagcagtgg ccatcggaat gagatcagac tccactaccg ctctggcact 420
caccgtcccc acacggaagt gtttccttat attttggctg atgccaagtg gcacaagctc 480
tccttagcct tcagtgcctc tcacttaatt ttacacatcg actgcaataa gatctatgaa 540
cgagtggtgg aaatgccttc aacagacttg cctctgggca ccacattttg gttgggacag 600
agaaataatg cacatggcta ttttaaggga ataatgcagg atgtgcacgt tcttgtcatg 660
cctcagggct tcattgctca gtgcccggac cttaatcgaa cctgtccaac atgcaacgac 720
ttccatgggc ttgtgcagaa aatcatggag ctgcaggaca ttttatcaaa gacgtcagcc 780
aagttgtcca gagctgaaca aagaatgaac aggctggatc agtgctactg tgagcggaca 840

-continued

```
tgcactgtga agggaaccac ctaccgagag tctgagtcct ggacagacgg ctgtaagaac    900
tgcacatgct tgaacgggac catccagtgc gagactctgg tctgccctgc tcctgactgc    960
cctcctaaat cggcccctgc gtatgtggat ggcaagtgct gtaaggagtg caaatcaacc   1020
tgccagttcc agggacggag ctactttgag ggagaaagga acacggtata ctcatcttct   1080
ggaatgtgtg tcttatatga atgcaaggat cagaccatga agcttgttga gaacattggc   1140
tgcccaccct tagattgtcc cgagtctcat cagattgcct tgtctcacag ctgctgcaag   1200
gtttgtaaag gttatgactt ctgttctgag aagcatacct gcatggagaa ctcggtctgc   1260
aggaacctga acgacagggc tgtgtgcagc tgcagggatg gttttcgggc tctccgagag   1320
gacaacgcct actgtgaaga cattgacgag tgtgcagaag ggcgccatta ctgccgtgag   1380
aacaccatgt gtgtgaatac acctggttct ttcatgtgta tctgcaaaac tgggtacatc   1440
aggatcgacg attactcatg tacagaacat gatgagtgtc tcacaaacca gcacaattgt   1500
gatgaaaacg ctttgtgctt taacactgtt ggaggacaca actgtgtctg caagcctggc   1560
tacaccggga atggaaccac gtgcaaagct ttctgcaaag atggctgtag aaacggagga   1620
gcgtgcattg ctgccaatgt gtgtgcctgc ccacaaggct tcacgggacc cagctgtgag   1680
acagacattg acgagtgctc tgagggcttt gttcagtgtg acagccgtgc caactgcatc   1740
aacctgcctg ggtggtatca ctgtgagtgc agagacggct accatgacaa tgggatgttt   1800
gcgccaggcg gagaatcctg tgaagatatt gacgaatgcg ggactgggag gcacagctgc   1860
accaacgaca ccatttgctt caacttggac gggggatacg attgccggtg tccccatggg   1920
aagaactgca ctggggactg cgtgcacgag ggaaagtga agcacaccgg ccagatctgg   1980
gtgctggaaa acgacaggtg ctccgtgtgt tcctgccaga ctgggtttgt catgtgtcga   2040
cggatggtct gcgactgcga aaaccccaca gttgaccttt cctgctgccc tgagtgtgac   2100
ccaaggctga gcagtcagtg cctgcatcaa aacggggaaa ccgtgtacaa cagcggcgac   2160
acctgggtcc aggattgccg tcagtgccgc tgcttgcaag gagaagttga ctgttggccc   2220
ctggcttgcc cagaggtaga atgtgaattt agcgtccttc ctgagaacga gtgctgccca   2280
cgctgtgtca ccgatccttg tcaggccgac accatccgca atgacatcac caaaacctgc   2340
ctggacgaga tgaacgtggt tcgcttcacc gggtcttcct ggatcaagca cggcacggag   2400
tgtaccctct gccagtgcaa gaatggccat ttgtgctgct cagtggatcc acagtgcctt   2460
caggagctgt gaagttaact gcctcatggg agatatctgt tcaaagaatg ttttctcatt   2520
tcaaaagacc aaataaataa ataaataaat aaaaagtgag gtgtggccag ccagatgcaa   2580
ctttgttagc agctggatag actgatgtcg attatggatt cgtggggcct gaggaacatc   2640
tctgaggaag cgagatgacc attctgcttt tactattcct gggatcacct tgcagaggaa   2700
tgggtgtgga gcccaggcca tgccatcctc gcccctggat aagaagcctg agccccatca   2760
gctctgggag agcctctcgc tctgtccgca gccaggcgca ggacacgtcc ttctatctca   2820
gactcttcct gagtcagcga ggctcctcac tgaggctgtc gaacgtgagg tgacagcggt   2880
gagcgagtta tattttcaga atccaagaag ctgatgcgtc tgtacagtgc actccgcaac   2940
ccgaaacaag ctattgtcat gataaataac gcacaggcat ggttacgtaa ccttttctaa   3000
cacgaaaagt cacccctccc cccccccccc agtttccttg tttactgccc ttaatattgt   3060
ttggttgaat ttgttcagta gacgcttgtt cttgtgcaaa ataaaataac tatttctctt   3120
accttaaaaa aaaaaaaaaa aaaa                                          3144
```

<210> SEQ ID NO 74
<211> LENGTH: 749
<212> TYPE: DNA
<213> ORGANISM: Mus musculus

<400> SEQUENCE: 74

```
agtttttctg ggtccaagcc cgggcacgga gttgtccctt tgcccaggca aagaaaggcc     60
atttgtgctg tcaagtggat ccacagtgcc ttcaggagct gtgaagttaa ctgcttcatg    120
gaagatatct gttcaaagaa tgttttctcc tttcaaaagc cccaataaat aaataaataa    180
ataaaaagtg aggtgtggcc agccagatgc aactttgtta gcagctggat agactgatgt    240
cgattatgga ttcgtggggc ctgaggaaca tctctgagga agcgagatgg ccattctgct    300
tttactattc ctgggatcac cttgcagagg aatgggtgtg gagcccaggc catgccatcc    360
tcgcccctgg ataagaagcc tgagccccat cagctctggg agagcctctc gctctgtccg    420
cagccaggcg caggacacgt ccttctatct cagactcttc ctgagtcagc gaggctcctc    480
actgaggctg tcgaacgtga ggtgacagcg gtgagcgagt tatattttca gaatccaaga    540
agctgatgcg tctgtacagt gcactccgca acccgaaaca agctattgtc atgataaata    600
acgcacaggc atggttacgt aacctttttct aacacgaaaa gtcacccctc cccccccca    660
gtttccttgt ttactgccct taatattgtt tggttgaatt tgttcagtag acgcttgttc    720
ttgtgcaaaa taaaataact atttctctc                                      749
```

<210> SEQ ID NO 75
<211> LENGTH: 2915
<212> TYPE: DNA
<213> ORGANISM: Rattus norvegicus

<400> SEQUENCE: 75

```
aagcactggt ttcttgttag cgttggtgcg ccctgcttgg cgggggttct ccggagcgat     60
gccgatggat gtgattttag ttttgtggtt ctgtgtatgc accgccagga cagtgttggg    120
ctttgggatg gaccctgacc ttcagctgga catcatctca gagctcgacc tggtgaacac    180
caccctggga gtcacgcagg tggctggact gcacaacgcc agtaaagcat ttctatttca    240
agatgtacag agagagatcc attcggcccc tcacgtgagt gagaagctga tccagctatt    300
ccggaataag agcgagttca cctttttggc tacagtgcag cagaaaccat ccacctcagg    360
ggtgatactg tccatccggg agctggagca cagctatttt gaactggaga gcagtggccc    420
aagagaagag atacgctacc attacataca tggtggaaag cccaggactg aggcccttcc    480
ctaccgcatg gcagacggac aatggcacaa ggtcgcgctg tcagtgagcg cctctcacct    540
cctgctccac atcgactgca ataggattta cgagcgtgtg atagaccctc cggagaccaa    600
ccttcctcca ggaagcaatc tgtggcttgg gcaacgtaac caaaagcatg gctttttcaa    660
aggaatcatc caagatggta agatcatctt catgccgaat ggtttcatca cacagtgtcc    720
caacctcaat cgcacttgcc caacatgcag tgacttcctg agcctggttc aaggaataat    780
ggatttgcaa gagcttttgg ccaagatgac tgcaaaactg aattatgcag agacgagact    840
tggtcaactg gaaaattgcc actgtgagaa gacctgccaa gtgagtgggc tgctctacag    900
ggaccaagac tcctgggtgg atggtgacaa ctgtgggaac tgcacgtgca aaagtggtgc    960
cgtggagtgc cgcaggatgt cctgtccccc gctcaactgt tccccggact cacttcctgt   1020
gcacatttcc ggccagtgtt gtaaagtttg cagaccaaaa tgtatctatg gaggaaaagt   1080
tcttgctgag ggccagcgga ttttaaccaa gacctgccgg gaatgtcgag gtggagtctt   1140
```

-continued

```
ggtaaaaatc acagaagctt gccctccttt gaactgctca gcaaaggatc atattcttcc   1200

agagaatcag tgctgcaggg tctgcccagg tcataacttc tgtgcagaag cacctaagtg   1260

cggagaaaac tcggaatgca aaaattggaa tacaaaagca acctgtgagt gcaagaatgg   1320

atacatctct gtccagggca actctgcata ctgtgaagat attgatgagt gtgcagctaa   1380

aatgcactat tgtcatgcca acaccgtgtg tgtcaacttg ccggggttgt atcgctgtga   1440

ctgcgtccca gggtacatcc gtgtggatga cttctcttgt acggagcatg atgattgtgg   1500

cagcggacaa cacaactgcg acaaaaatgc catctgtacc aacacagtcc agggacacag   1560

ctgcacctgc cagccgggtt acgtgggaaa tggcaccatc tgcaaagcat tctgtgaaga   1620

gggttgcaga tacggaggta cctgtgtggc tcctaacaag tgtgtctgtc cttctggatt   1680

cacgggaagc cactgtgaga aagatattga tgaatgcgca gagggattcg ttgaatgcca   1740

caactactcc cgctgtgtta acctgccagg gtggtaccac tgtgagtgca gaagcggttt   1800

ccatgacgat gggacctact cactgtccgg ggagtcctgc attgatatcg atgaatgtgc   1860

cttaagaact cacacttgtt ggaatgactc tgcctgcatc aacttagcag gaggatttga   1920

ctgcctgtgt ccctctgggc cctcctgctc tggtgactgt ccccacgaag gagggctgaa   1980

gcataatggg caggtgtgga ttctgagaga agacaggtgt tcagtctgtt cctgcaagga   2040

tgggaagata ttctgccggc ggacagcttg tgattgccag aatccaaatg ttgacctttt   2100

ttgctgccca gagtgcgata ccagggtcac cagccaatgt ttagatcaaa gtggacagaa   2160

gctctatcga agtggagaca actggaccca cagctgccag cagtgccgat gtctggaagg   2220

agaggcagac tgctggcctc tggcttgccc tagtttgggc tgtgaataca cagccatgtt   2280

tgaaggggag tgttgtcccc gatgtgtcag tgacccctgc ctggctggta atattgccta   2340

tgacatcaga aaaacttgcc tggacagctt tggtgtttcg aggctgagcg gagccgtgtg   2400

gacaatggct ggatctcctt gtacaacctg caaatgcaag aatgggagag tctgctgctc   2460

tgtggatctg gagtgtattg agaataactg aagattttaa atggactcgt cacgtgagaa   2520

aatgggcaaa atgatcatcc cacctgagga agaagagggg ctgatttctt tttcttttta   2580

accacagtca attaccaaag tctccatctg aggaaggcgt ttggattgcc tttgccactt   2640

tgctcatcct tgctgaccta gtctagatgc ctgcagtacc gtgcatttcg gtcgatggtt   2700

gttgagtctc agtgttgtaa atcgcatttc cctcgtcaga tcatttacag atacatttaa   2760

aggggttcca tgataaatgt taatgtaact tttgtttatt ttgtgtactg acataataga   2820

gacttggcac catttattta tttttcttga tttttggatc aaattctaaa aataaagttg   2880

cctgttgcga aaaaaaaaaa aaaaaaaaaa aaaaa                              2915
```

```
<210> SEQ ID NO 76
<211> LENGTH: 2915
<212> TYPE: DNA
<213> ORGANISM: Rattus norvegicus

<400> SEQUENCE: 76

aagcactggt ttcttgttag cgttggtgcg ccctgcttgg cgggggttct ccggagcgat     60

gccgatggat gtgattttag ttttgtggtt ctgtgtatgc accgccagga cagtgttggg    120

ctttgggatg gaccctgacc ttcagctgga catcatctca gagctcgacc tggtgaacac    180

caccctggga gtcacgcagg tggctggact gcacaacgcc agtaaagcat ttctatttca    240

agatgtacag agagagatcc attcggcccc tcacgtgagt gagaagctga tccagctatt    300

ccggaataag agcgagttca cctttttggc tacagtgcag cagaaaccat ccacctcagg    360
```

```
ggtgatactg tccatccggg agctggagca cagctatttt gaactggaga gcagtggccc    420
aagagaagag atacgctacc attacataca tggtggaaag cccaggactg aggcccttcc    480
ctaccgcatg gcagacggac aatggcacaa ggtcgcgctg tcagtgagcg cctctcacct    540
cctgctccac atcgactgca ataggattta cgagcgtgtg atagaccctc cggagaccaa    600
ccttcctcca ggaagcaatc tgtggcttgg gcaacgtaac caaaagcatg gctttttcaa    660
aggaatcatc caagatggta agatcatctt catgccgaat ggtttcatca cacagtgtcc    720
caacctcaat cgcacttgcc caacatgcag tgacttcctg agcctggttc aaggaataat    780
ggatttgcaa gagcttttgg ccaagatgac tgcaaaactg aattatgcag agacgagact    840
tggtcaactg gaaaattgcc actgtgagaa gacctgccaa gtgagtgggc tgctctacag    900
ggaccaagac tcctgggtgg atggtgacaa ctgtgggaac tgcacgtgca aaagtggtgc    960
cgtggagtgc cgcaggatgt cctgtccccc gctcaactgt tccccggact cacttcctgt   1020
gcacatttcc ggccagtgtt gtaaagtttg cagaccaaaa tgtatctatg gaggaaaagt   1080
tcttgctgag ggccagcgga ttttaaccaa gacctgccgg gaatgtcgag gtggagtctt   1140
ggtaaaaatc acagaagctt gccctccttt gaactgctca gcaaaggatc atattcttcc   1200
agagaatcag tgctgcaggg tctgcccagg tcataacttc tgtgcagaag cacctaagtg   1260
cggagaaaac tcggaatgca aaaattggaa tacaaaagca acctgtgagt gcaagaatgg   1320
atacatctct gtccagggca actctgcata ctgtgaagat attgatgagt gtgcagctaa   1380
aatgcactat tgtcatgcca acaccgtgtg tgtcaacttg ccggggttgt atcgctgtga   1440
ctgcgtccca gggtacatcc gtgtggatga cttctcttgt acggagcatg atgattgtgg   1500
cagcggacaa cacaactgcg acaaaaatgc catctgtacc aacacagtcc agggacacag   1560
ctgcacctgc cagccgggtt acgtgggaaa tggcaccatc tgcaaagcat tctgtgaaga   1620
gggttgcaga tacggaggta cctgtgtggc tcctaacaag tgtgtctgtc cttctggatt   1680
cacgggaagc cactgtgaga aagatattga tgaatgcgca gagggattcg ttgaatgcca   1740
caactactcc cgctgtgtta acctgccagg gtggtaccac tgtgagtgca gaagcggttt   1800
ccatgacgat gggacctact cactgtccgg ggagtcctgc attgatatcg atgaatgtgc   1860
cttaagaact cacacttgtt ggaatgactc tgcctgcatc aacttagcag gaggatttga   1920
ctgcctgtgt ccctctgggc cctcctgctc tggtgactgt ccccacgaag gagggctgaa   1980
gcataatggg caggtgtgga ttctgagaga agacaggtgt tcagtctgtt cctgcaagga   2040
tgggaagata ttctgccggc ggacagcttg tgattgccag aatccaaatg ttgacctttt   2100
ttgctgccca gagtgcgata ccagggtcac cagccaatgt ttagatcaaa gtggacagaa   2160
gctctatcga agtggagaca actggaccca cagctgccag cagtgccgat gtctggaagg   2220
agaggcagac tgctggcctc tggcttgccc tagtttgggc tgtgaataca cagccatgtt   2280
tgaaggggag tgttgtcccc gatgtgtcag tgacccctgc ctggctggta atattgccta   2340
tgacatcaga aaaacttgcc tggacagctt tggtgtttcg aggctgagcg gagccgtgtg   2400
gacaatggct ggatctcctt gtacaacctg caaatgcaag aatgggagag tctgctgctc   2460
tgtggatctg gagtgtattg agaataactg aagattttaa atggactcgt cacgtgagaa   2520
aatgggcaaa atgatcatcc cacctgagga agaagagggg ctgatttctt tttcttttta   2580
accacagtca attaccaaag tctccatctg aggaaggcgt ttggattgcc tttgccactt   2640
tgctcatcct tgctgaccta gtctagatgc ctgcagtacc gtgcatttcg gtcgatggtt   2700
```

-continued

```
gttgagtctc agtgttgtaa atcgcatttc cctcgtcaga tcatttacag atacatttaa   2760

aggggttcca tgataaatgt taatgtaact tttgtttatt ttgtgtactg acataataga   2820

gacttggcac catttattta tttttcttga tttttggatc aaattctaaa aataaagttg   2880

cctgttgcga aaaaaaaaaa aaaaaaaaaa aaaaa                              2915
```

<210> SEQ ID NO 77
<211> LENGTH: 3196
<212> TYPE: DNA
<213> ORGANISM: Rattus norvegicus

<400> SEQUENCE: 77

```
gtcctttctc tcgccgggtt tggagacacg ctcccgattt cgaggggagg gagacgatgg     60

actgagacga tgcacgccat ggaatcccgg gtattactga gaacgttctg cgtgatcctc    120

gggctcgaag cggtttgggg acttggtgtg gacccctccc tacagattga cgtcttatca    180

gagttagaac ttggggagtc cacagctgga gtgcgccaag tcccaggact gcataatggg    240

acgaaagcct tcctcttcca agattctccc agaagcataa aagcacccat tgctacagct    300

gagcggtttt tccagaagct gaggaataaa cacgagttca caattctggt gaccctgaaa    360

cagatccact taaattcggg agtcattctc tccatccacc acttggatca caggtacctg    420

gaactggaaa gcagcggcca ccggaatgag atcagactgc attaccgctc tggaactcac    480

cgcccgcaca cggaagtgtt tccttacatt ttggctgatg ccaagtggca caagctctcc    540

ttagccttca gtgcctccca cttaatttta cacatcgact gcaacaagat ctatgaacga    600

gtggtggaaa tgccttctac agacttgcct ctgggcacca cattttggtt gggacagaga    660

aataacgcac acgggtattt taagggaata atgcaagatg tgcaattact tgtcatgccc    720

caggggttca tcgctcagtg cccggatctt aatcgaacct gtccaacatg caacgacttc    780

catgggcttg tgcagaaaat catggagctg caggacattt tatcgaagac gtcagccaag    840

ttgtctagag ctgaacaacg aatgaacagg ctggatcagt gctactgtga gcggacgtgc    900

accatgaagg gaaccaccta ccgggagttc gagtcctgga cagacggctg caagaactgc    960

acatgcttga atgggaccat ccagtgcgag actctggtct gccctgctcc cgactgcccg   1020

gctaaatcgg ctccagcgta cgtggatggc aagtgctgta aggagtgcaa gtccacctgc   1080

cagttccagg ggcggagcta ctttgaggga gaaaggagca cagtcttctc agcttccgga   1140

atgtgcgtct tgtatgaatg caaggatcag accatgaagc ttgttgagaa cgccggctgc   1200

ccggctttag attgccccga gtctcatcag atcgccttgt ctcacagctg ctgcaaggtt   1260

tgcaaaggtt atgacttctg ttctgagaag catacatgca tggagaactc agtctgcagg   1320

aacctgaacg acagggcagt gtgcagctgc cgggatggtt tccgggccct ccgggaggac   1380

aatgcctact gtgaagacat tgacgagtgt gcagaggggc gccattactg ccgtgagaac   1440

accatgtgtg tgaacacacc gggctctttc ctgtgtatct gccaaacagg gtacatcaga   1500

atcgacgatt actcgtgtac ggaacatgac gagtgcctca caaaccagca caattgtgac   1560

gagaacgctt tgtgctttaa caccgttgga ggtcacaact gcgtctgcaa gcctggctac   1620

actgggaatg gaaccacgtg caaagctttc tgcaaagacg gctgcagaaa cggaggtgcc   1680

tgcattgctg ccaatgtctg tgcttgccca caaggcttca ccggacccag ctgtgagaca   1740

gacattgatg agtgctctga gggctttgtt cagtgtgaca gccgtgccaa ctgcattaac   1800

ctgcctgggt ggtaccactg tgagtgcaga gatggctacc atgacaatgg gatgtttgca   1860

ccaggtggag aatcctgtga agatattgat gaatgtggga ctgggaggca cagctgtgcc   1920
```

-continued

```
aatgacacca tttgcttcaa cttggacggt ggctacgatt gccggtgtcc ccatggaaag   1980

aactgcacag gggactgcgt gcacgacggg aaagtcaaac acaacggcca gatctgggtg   2040

ctggagaacg acaggtgctc tgtgtgttcc tgccagactg gatttgttat gtgtcgacgg   2100

atggtctgtg actgcgaaaa ccccacagtt gacctctcct gctgccctga gtgcgaccca   2160

aggctgagca gccagtgcct gcatcaaaac ggggaaaccg tgtacaacag cggtgacacc   2220

tgggtccagg attgccgtca gtgccgctgc ttgcaaggag aagttgactg ctggcccctg   2280

gcttgcccag aggtagagtg tgaatttagt gtccttcctg agaacgagtg ctgcccacgc   2340

tgtgtcaccg atccttgtca ggctgacacc atccgcaatg acatcaccaa aacctgcctg   2400

gacgagatga acgtggttcg cttcactggg tcttcctgga tcaagcacgg cacagagtgc   2460

accctctgcc agtgcaagaa cggccacgtg tgctgctcag tggacccaca gtgcctccag   2520

gagctgtgaa gttaactgcc tcatgggaga tacctgttca aagaatgatt tctcatttaa   2580

aaagaccaaa aaacaaaaaa gaaaaaaagt gatgtgcggc cagccaaatg caactgtgtc   2640

aatggctggg cagactgatg gcgattacgg ctctgtagag ctttgaggaa catcactgag   2700

gaaaccagat ggcagttccg cctttactgt tcctgggatc accttacgga gaaatggctg   2760

tgaatcacag gccttgacat ccccagccct ggagaagaag cctgagccca tcagctctgg   2820

ggaagtctct ccctctctcc ctccctccgc aggcacagga catgtcctag ctcagactct   2880

tcctgaacca gcgaggttcc tcactgaagc cgtggaatga aaggcagtga gtgagctata   2940

ttttcagaat ccaagaagct gacacatctg tacagtgcac tccgaaccct gaaacaagct   3000

attgtaatga taaaatactg cacaggcatg gttatgtaac attttctaac cggagaagtc   3060

accccacccc catttcctcg tttactgcac ttaatgttat ttggtttgaa tttgttcagt   3120

agaagctcgt tcttgtgcaa aataaaataa ctatttctct taccttaaaa aaaaaaaaaa   3180

aaaaaaaaaa aaaagg                                                   3196
```

```
<210> SEQ ID NO 78
<211> LENGTH: 2618
<212> TYPE: DNA
<213> ORGANISM: Rattus norvegicus

<400> SEQUENCE: 78
```

```
gtcctttctc tcgccgggtt tggagacacg ctcccgattt cgaggggagg gagacgatgg     60

actgagacga tgcacgccat ggaatcccgg gtattactga gaacgttctg cgtgatcctc    120

gggctcgaag cggtttgggg acttggtgtg gacccctccc tacagattga cgtcttatca    180

gagttagaac ttggggagtc cacagctgga gtgcgccaag tcccaggact gcataatggg    240

acgaaagcct tcctcttcca agattccccc agaagcataa aagcacccat tgctacagct    300

gagcggtttt tccagaagct gaggaataaa cacgagttca caattctggt gaccctgaaa    360

cagatccact taaattcggg agtcattctc tccatccacc acttggatca caggtacctg    420

gaactggaaa gcagcggcca ccggaatgag atcagactgc attaccgctc tggaactcac    480

cgcccgcaca cggaagtgtt tccttatatt ttggctgatg ccaagtggca caagctctcc    540

ttagccttca gtgcctccca cttaatttta cacatcgact gcaacaagat ctatgaacga    600

gtggtggaaa tgccttctac agacttgcct ctgggcacca cattttggtt gggacagaga    660

aataacgcac acgggtattt taagggaata atgcaagatg tgcaattact tgtcatgccc    720

caggggttca tcgctcagtg cccggatctt aatcgaacct gtccaacatg caacgacttc    780
```

catgggcttg tgcagaaaat catggagctg caggacattt tatcgaagac gtcagccaag 840
ttgtctagag ctgaacaacg aatgaacagg ctggatcagt gctactgtga gcggacgtgc 900
accatgaagg gagccaccta ccgggagttc gagtcctgga cagacggctg caagaactgc 960
acatgcttga atgggaccat ccagtgcgag actctggtct gccctgctcc cgactgcccg 1020
gctaaatcgg ctccagcgta cgtggatggc aagtgctgta aggagtgcaa gtccacctgc 1080
cagttccagg ggcggagcta ctttgaggga gaaaggagca cagtcttctc agcttccgga 1140
atgtgcgtct tgtatgaatg caaggatcag accatgaagc ttgttgagaa cgccggctgc 1200
ccggctttag attgccccga gtctcatcag atcgccttgt ctcacagctg ctgcaaggtt 1260
tgcaaaggtt atgacttctg ttctgagaag catacatgca tggagaactc agtctgcagg 1320
aacctgaacg acagggcagt gtgcagctgc cgggatggtt tccgggccct ccgggaggac 1380
aatgcctact gtgaagacat tgacgagtgt gcagaggggc gccattactg ccgtgagaac 1440
accatgtgtg tgaacacacc gggctctttc ctgtgtatct gccaaacagg gtacatcaga 1500
atcgacgatt actcgtgtac ggaacatgac gagtgcctca caaaccagca caactgtgac 1560
gagaacgctt tgtgctttaa caccgttgga ggtcacaact gcgtctgcaa gcctgggtac 1620
actgggaatg gaaccacgtg caaagctttc tgcaaagacg gctgcaaaaa cggaggtgcc 1680
tgcattgctg ccaatgtctg tgcttgccca caaggcttca ccggacccag ctgtgagaca 1740
gacattgatg agtgctctga gggctttgtt cagtgtgaca gccgtgccaa ctgcattaac 1800
ctgcctgggt ggtaccactg tgagtgcaga gatggctacc atgacaatgg gatgtttgcg 1860
ccaggtggag aatcctgtga agatattgat gaatgtggga ctgggaggca cagctgtgcc 1920
aatgacacca tttgcttcaa cttggacggt ggctacgatt gccggtgtcc ccatggaaag 1980
aactgcacag gggactgcgt gcacgacggg aaagtcaaac acaacggcca gatctgggtg 2040
ctggagaacg acaggtgctc tgtgtgttcc tgccagactg gatttgttat gtgccaacgg 2100
atggtctgtg actgcgaaaa ccccacagtt gacctctcct gctgccctga gtgcgaccca 2160
aggctgagca gccagtgcct gcatcaaaac ggggaaaccg tgtacaacag cggtgacacc 2220
tgggcccagg attgccgtca gtgccgctgc ttgcaagaag aagttgactg ctggcccctg 2280
gcttgcccag aggtagagtg tgaatttagt gtccttcctg agaacgagtg ctgcccacgc 2340
tgtgtcaccg atccttgtca ggctgacacc atccgcaatg acatcaccaa aacctgcctg 2400
gacgagatga acgtggttcg cttcactggg tcttcctgga tcaagcacgg cacggagtgc 2460
accctctgcc agtgcaagaa cggccacgtg tgctgctcag tggacccaca gtgcctccag 2520
gagctgtgaa gttaactgcc tcatgggaga tacctgttaa agaatgattt ctcatttaaa 2580
aaaaaaaaaa aaaaaaaaaa aaaaaaaaaa aaaaaaaa 2618

<210> SEQ ID NO 79
<211> LENGTH: 3140
<212> TYPE: DNA
<213> ORGANISM: Rattus norvegicus

<400> SEQUENCE: 79
atggactgag acgatgcacg ccatggaatc ccgggtatta ctgagaacgt tctgcgtgat 60
cctcgggctc gaagcggttt ggggacttgg tgtggacccc tccctacaga ttgacgtctt 120
atcagagtta gaacttgggg agtccacagc tggagtgcgc caagtcccag gactgcataa 180
tgggacgaaa gccttcctct tccaagattc tcccagaagc ataaaagcac ccattgctac 240
agctgagcgg tttttccaga agctgaggaa taaacacgag ttcacaattc tggtgaccct 300

-continued

```
gaaacagatc cacttaaatt cgggagtcat tctctccatc caccacttgg atcacaggta    360
cctggaactg gaaagcagcg gccaccggaa tgagatcaga ctgcattacc gctctggaac    420
tcaccgcccg cacacggaag tgtttcctta cattttggct gatgccaagt ggcacaagct    480
ctccttagcc ttcagtgcct cccacttaat tttacacatc gactgcaaca agatctatga    540
acgagtggtg gaaatgcctt ctacagactt gcctctgggc accacatttt ggttgggaca    600
gagaaataac gcacacgggt attttaaggg aataatgcaa gatgtgcaat tacttgtcat    660
gccccagggg ttcatcgctc agtgcccgga tcttaatcga acctgtccaa catgcaacga    720
cttccatggg cttgtgcaga aaatcatgga gctgcaggac attttatcga agacgtcagc    780
caagttgtct agagctgaac aacgaatgaa caggctggat cagtgctact gtgagcggac    840
gtgcaccatg aagggaacca cctaccggga gttcgagtcc tggacagacg gctgcaagaa    900
ctgcacatgc ttgaatggga ccatccagtg cgagactctg gtctgccctg ctcccgactg    960
cccggctaaa tcggctccag cgtacgtgga tggcaagtgc tgtaaggagt gcaagtccac   1020
ctgccagttc caggggcgga gctactttga gggagaaagg agcacagtct tctcagcttc   1080
cggaatgtgc gtcttgtatg aatgcaagga tcagaccatg aagcttgttg agaacgccgg   1140
ctgcccggct ttagattgcc ccgagtctca tcagatcgcc ttgtctcaca gctgctgcaa   1200
ggtttgcaaa ggttatgact tctgttctga gaagcataca tgcatggaga actcagtctg   1260
caggaacctg aacgacaggg cagtgtgcag ctgccgggat ggtttccggg ccctccggga   1320
ggacaatgcc tactgtgaag acattgacga gtgtgcagag ggcgccatt actgccgtga   1380
gaacaccatg tgtgtgaaca caccgggctc tttcctgtgt atctgccaaa cagggtacat   1440
cagaatcgac gattactcgt gtacggaaca tgacgagtgc ctcacaaacc agcacaattg   1500
tgacgagaac gctttgtgct ttaacaccgt tggaggtcac aactgcgtct gcaagcctgg   1560
ctacactggg aatggaacca cgtgcaaagc tttctgcaaa gacggctgca gaaacggagg   1620
tgcctgcatt gctgccaatg tctgtgcttg cccacaaggc ttcaccggac ccagctgtga   1680
gacagacatt gatgagtgct ctgagggctt tgttcagtgt gacagccgtg ccaactgcat   1740
taacctgcct gggtggtacc actgtgagtg cagagatggc taccatgaca atgggatgtt   1800
tgcaccaggt ggagaatcct gtgaagatat tgatgaatgt gggactggga ggcacagctg   1860
tgccaatgac accatttgct tcaacttgga cggtggctac gattgccggt gtccccatgg   1920
aaagaactgc acaggggact gcgtgcacga cgggaaagtc aaacacaacg gccagatctg   1980
ggtgctggag aacgacaggt gctctgtgtg ttcctgccag actggatttg ttatgtgtcg   2040
acggatggtc tgtgactgcg aaaaccccac agttgacctc tcctgctgcc ctgagtgcga   2100
cccaaggctg agcagccagt gcctgcatca aaacggggaa accgtgtaca acagcggtga   2160
cacctgggtc caggattgcc gtcagtgccg ctgcttgcaa ggagaagttg actgctggcc   2220
cctggcttgc ccagaggtag agtgtgaatt tagtgtcctt cctgagaacg agtgctgccc   2280
acgctgtgtc accgatcctt gtcaggctga caccatccgc aatgacatca ccaaaacctg   2340
cctggacgag atgaacgtgg ttcgcttcac tgggtcttcc tggatcaagc acggcacaga   2400
gtgcaccctc tgccagtgca agaacggcca cgtgtgctgc tcagtggacc cacagtgcct   2460
ccaggagctg tgaagttaac tgcctcatgg gagatacctg ttcaaagaat gatttctcat   2520
ttaaaaagac caaaaaacaa aaaagaaaaa aagtgatgtg cggccagcca aatgcaactg   2580
tgtcaatggc tgggcagact gatggcgatt acggctctgt agagctttga ggaacatcac   2640
```

tgaggaaacc agatggcagt tccgccttta ctgttcctgg gatcacctta cggagaaatg 2700
gctgtgaatc acaggccttg acatccccag ccctggagaa gaagcctgag cccatcagct 2760
ctggggaagt ctctccctct ctccctccct ccgcaggcac aggacatgtc ctagctcaga 2820
ctcttcctga accagcgagg ttcctcactg aagccgtgga atgaaaggca gtgagtgagc 2880
tatattttca gaatccaaga agctgacaca tctgtacagt gcactccgaa ccctgaaaca 2940
agctattgta atgataaaat actgcacagg catggttatg taacattttc taaccggaga 3000
agtcacccca cccccatttc ctcgtttact gcacttaatg ttatttggtt tgaatttgtt 3060
cagtagaagc tcgttcttgt gcaaaataaa ataactattt ctcttacctt aaaaaaaaaa 3120
aaaaaaaaaa aaaaaaaagg 3140

<210> SEQ ID NO 80
<211> LENGTH: 2583
<212> TYPE: DNA
<213> ORGANISM: Rattus norvegicus

<400> SEQUENCE: 80
gtcctttctc tcgccgggtt tggagacacg ctcccgattt cgaggggagg gagacgatgg 60
actgagacga tgcacgccat ggaatcccgg gtattactga gaacgttctg cgtgatcctc 120
gggctcgaag cggtttgggg acttggtgtg gacccctccc tacagattga cgtcttatca 180
gagttagaac ttggggagtc cacagctgga gtgcgccaag tcccaggact gcataatggg 240
acgaaagcct tcctcttcca agattctccc agaagcataa aagcacccat tgctacagct 300
gagcggtttt tccagaagct gaggaataaa cacgagttca caattctggt gaccctgaaa 360
cagatccact taaattcggg agtcattctc tccatccacc acttggatca caggtacctg 420
gaactggaaa gcagcggcca ccggaatgag atcagactgc attaccgctc tggaactcac 480
cgcccgcaca cggaagtgtt tccttacatt ttggctgatg ccaagtggca caagctctcc 540
ttagccttca gtgcctccca cttaatttta cacatcgact gcaacaagat ctatgaacga 600
gtggtggaaa tgccttctac agacttgcct ctgggcacca cattttggtt gggacagaga 660
aataacgcac acgggtattt taagggaata atgcaagatg tgcaattact tgtcatgccc 720
caggggttca tcgctcagtg cccggatctt aatcgaacct gtccaacatg caacgacttc 780
catgggcttg tgcagaaaat catggagctg caggacattt tatcgaagac gtcagccaag 840
ttgtctagag ctgaacaacg aatgaacagg ctggatcagt gctactgtga gcggacgtgc 900
accatgaagg gaaccaccta ccgggagttc gagtcctgga cagacggctg caagaactgc 960
acatgcttga atgggaccat ccagtgcgag actctggtct gccctgctcc cgactgcccg 1020
gctaaatcgg ctccagcgta cgtggatggc aagtgctgta aggagtgcaa gtccacctgc 1080
cagttccagg ggcggagcta ctttgaggga gaaaggagca cagtcttctc agcttccgga 1140
atgtgcgtct tgtatgaatg caaggatcag accatgaagc ttgttgagaa cgccggctgc 1200
ccggctttag attgccccga gtctcatcag atcgccttgt ctcacagctg ctgcaaggtt 1260
tgcaaaggtt atgacttctg ttctgagaag catacatgca tggagaactc agtctgcagg 1320
aacctgaacg acagggcagt gtgcagctgc cgggatggtt tccgggccct ccgggaggac 1380
aatgcctact gtgaagacat tgacgagtgt gcagaggggc gccattactg ccgtgagaac 1440
accatgtgtg tgaacacacc gggctctttc ctgtgtatct gccaaacagg gtacatcaga 1500
atcgacgatt actcgtgtac ggaacatgac gagtgcctca caaaccagca caattgtgac 1560
gagaacgctt tgtgctttaa caccgttgga ggtcacaact gcgtctgcaa gcctggctac 1620

```
actgggaatg gaaccacgtg caaagctttc tgcaaagacg gctgcagaaa cggaggtgcc   1680
tgcattgctg ccaatgtctg tgcttgccca caaggcttca ccggacccag ctgtgagaca   1740
gacattgatg agtgctctga gggctttgtt cagtgtgaca gccgtgccaa ctgcattaac   1800
ctgcctgggt ggtaccactg tgagtgcaga gatggctacc atgacaatgg gatgtttgca   1860
ccaggtggag aatcctgtga agatattgat gaatgtggga ctgggaggca cagctgtgcc   1920
aatgacacca tttgcttcaa cttggacggt ggctacgatt gccggtgtcc ccatggaaag   1980
aactgcacag gggactgcgt gcacgacggg aaagtcaaac acaacggcca gatctgggtg   2040
ctggagaacg acaggtgctc tgtgtgttcc tgccagactg gatttgttat gtgtcgacgg   2100
atggtctgtg actgcgaaaa ccccacagtt gacctctcct gctgccctga gtgcgaccca   2160
aggctgagca gccagtgcct gcatcaaaac ggggaaaccg tgtacaacag cggtgacacc   2220
tgggtccagg attgccgtca gtgccgctgc ttgcaaggag aagttgactg ctggcccctg   2280
gcttgcccag aggtagagtg tgaatttagt gtccttcctg agaacgagtg ctgcccacgc   2340
tgtgtcaccg atccttgtca ggctgacacc atccgcaatg acatcaccaa aacctgcctg   2400
gacgagatga acgtggttcg cttcactggg tcttcctgga tcaagcacgg cacagagtgc   2460
accctctgcc agtgcaagaa cggccacgtg tgctgctcag tggacccaca gtgcctccag   2520
gagctgtgaa gttaactgcc tcatgggaga tacctgttca aagaatgatt tctcatttaa   2580
aaa                                                                 2583
```

<210> SEQ ID NO 81
<211> LENGTH: 2618
<212> TYPE: DNA
<213> ORGANISM: Rattus norvegicus

<400> SEQUENCE: 81

```
gtcctttctc tcgccgggtt tggagacacg ctcccgattt cgaggggagg gagacgatgg     60
actgagacga tgcacgccat ggaatcccgg gtattactga gaacgttctg cgtgatcctc    120
gggctcgaag cggtttgggg acttggtgtg gacccctccc tacagattga cgtcttatca    180
gagttagaac ttggggagtc cacagctgga gtgcgccaag tcccaggact gcataatggg    240
acgaaagcct tcctcttcca agattccccc agaagcataa aagcacccat tgctacagct    300
gagcggtttt tccagaagct gaggaataaa cacgagttca caattctggt gaccctgaaa    360
cagatccact taaattcggg agtcattctc tccatccacc acttggatca caggtacctg    420
gaactggaaa gcagcggcca ccggaatgag atcagactgc attaccgctc tggaactcac    480
cgcccgcaca cggaagtgtt tccttatatt ttggctgatg ccaagtggca caagctctcc    540
ttagccttca gtgcctccca cttaatttta cacatcgact gcaacaagat ctatgaacga    600
gtggtggaaa tgccttctac agacttgcct ctgggcacca cattttggtt gggacagaga    660
aataacgcac acgggtattt taagggaata atgcaagatg tgcaattact tgtcatgccc    720
caggggttca tcgctcagtg cccggatctt aatcgaacct gtccaacatg caacgacttc    780
catgggcttg tgcagaaaat catggagctg caggacattt tatcgaagac gtcagccaag    840
ttgtctagag ctgaacaacg aatgaacagg ctggatcagt gctactgtga gcggacgtgc    900
accatgaagg gagccaccta ccgggagttc gagtcctgga cagacggctg caagaactgc    960
acatgcttga atgggaccat ccagtgcgag actctggtct gccctgctcc cgactgcccg   1020
gctaaatcgg ctccagcgta cgtggatggc aagtgctgta aggagtgcaa gtccacctgc   1080
```

```
cagttccagg ggcggagcta ctttgaggga gaaaggagca cagtcttctc agcttccgga   1140
atgtgcgtct tgtatgaatg caaggatcag accatgaagc ttgttgagaa cgccggctgc   1200
ccggctttag attgccccga gtctcatcag atcgccttgt ctcacagctg ctgcaaggtt   1260
tgcaaaggtt atgacttctg ttctgagaag catacatgca tggagaactc agtctgcagg   1320
aacctgaacg acagggcagt gtgcagctgc cgggatggtt tccgggccct ccgggaggac   1380
aatgcctact gtgaagacat tgacgagtgt gcagaggggc gccattactg ccgtgagaac   1440
accatgtgtg tgaacacacc gggctctttc ctgtgtatct gccaaacagg gtacatcaga   1500
atcgacgatt actcgtgtac ggaacatgac gagtgcctca caaaccagca caactgtgac   1560
gagaacgctt tgtgctttaa caccgttgga ggtcacaact gcgtctgcaa gcctggctac   1620
actgggaatg gaaccacgtg caaagctttc tgcaaagacg gctgcagaaa cggaggtgcc   1680
tgcattgctg ccaatgtctg tgcttgccca caaggcttca ccggacccag ctgtgagaca   1740
gacattgatg agtgctctga gggctttgtt cagtgtgaca gccgtgccaa ctgcattaac   1800
ctgcctgggt ggtaccactg tgagtgcaga gatggctacc atgacaatgg gatgtttgcg   1860
ccaggtggag aatcctgtga agatattgat gaatgtggga ctgggaggca cagctgtgcc   1920
aatgacacca tttgcttcaa cttggacggt ggctacgatt gccggtgtcc ccatggaaag   1980
aactgcacag gggactgcgt gcacgacggg aaagtcaaac acaacggcca gatctgggtg   2040
ctggagaacg acaggtgctc tgtgtgttcc tgccagactg gatttgttat gtgtcgacgg   2100
atggtctgtg actgcgaaaa ccccacagtt gacctctcct gctgccctga gtgcgaccca   2160
aggctgagca gccagtgcct gcatcaaaac ggggaaaccg tgtacaacag cggtgacacc   2220
tgggtccagg attgccgtca gtgccgctgc ttgcaaggag aagttgactg ctggcccctg   2280
gcttgcccag aggtagagtg tgaatttagt gtccttcctg agaacgagtg ctgcccacgc   2340
tgtgtcaccg atccttgtca ggctgacacc atccgcaatg acatcaccaa aacctgcctg   2400
gacgagatga acgtggttcg cttcactggg tcttcctgga tcaagcacgg cacggagtgc   2460
accctctgcc agtgcaagaa cggccacgtg tgctgctcag tggacccaca gtgcctccag   2520
gagctgtgaa gttaactgcc tcatgggaga tacctgttaa agaatgattt ctcatttaaa   2580
aaaaaaaaaa aaaaaaaaaa aaaaaaaaaa aaaaaaaa                           2618
```

<210> SEQ ID NO 82
<211> LENGTH: 2213
<212> TYPE: DNA
<213> ORGANISM: Homo sapiens

<400> SEQUENCE: 82

```
gctgcaaagc tatgacagaa catatgtctt gctttatttt ttaatggaac aagctaaaag     60
tcccatccca caggaccagc taattacaca gagactttaa agatagagag ctctgaagat    120
cttacccaga ccacctttc cccttgctgg ggtcactgta cttttaagga ttctgggctt    180
tctgaaatca ataaaagggc cttggaaaca acagtccaaa gcaactcaag gctgttcctg    240
ctgaggtgta cttaaagact gcagaggaga gacaggaaat ggctcttata atacaacatg    300
gtgtatggtg tccttgtcca caaggcccaa caagacttgg gaaatcctat tctcttcaag    360
atgtgtgatt ttaatgttag ctttaaatgc aacacgctcc gggtggaagg aaaaacacgt    420
ggactctgtt agtgaaaata cagagtcaag gcagacagat ttcctttggg tcttagccga    480
atctgagttg gagtcagctg acatcagttt acctcttaat cattcagctc agcttctgga    540
ttgtgcagta gacttcttga gctggaattt acctgcttgt tcactttctt tttcatctgc    600
```

-continued

```
caaaggacca caacataaag ggccaaatgg gacagtggct tgcacacaga aatatccaga    660

aaaatagggc agagaccaga agagcatgct agtaaagcct tctctcttaa taagctgcgc    720

tgatttggtg aacttcactg gggctcctgg ggtcaaagtt gtgtaggggt taaggatata    780

ggaagtgaaa gtgggtgcaa gtgagaaggg cacgttctta ttagtgaaga ggattctgaa    840

acgttggaat tggtttccag gaaacgaggg acggctgttc tgaggtttcc ttggactcct    900

ctgggatccc tgttgtgaat atcaaaggag tactgctggt gagggggagc gggggcttca    960

gagagagtgg gaagactgag caagctaagt ggagttcatt tggtataaat cagaggctgt   1020

catttcagat ttcatgactc tacatatcca gttataaata acattcctag gtgttagtag   1080

gacaaatagg aagtgggaca gaagtctcaa atttggggga tcttcatagg gaaggtcagg   1140

tcctgaaagg gtcgcagaga ggggagagga cccattctct tcttgccggc aagtagaaaa   1200

caaagcccag cccagctttt ctctccagag aatgttgtgg tgggagaggg aaaagaaggt   1260

ggaggtcccg gaggaattgc acatggggcc aaaatgtgac tatgaaagaa gagtgggctt   1320

ttgataatac cattaagaaa atcacgcaag aaagaaaaaa agatggttag gaattacccc   1380

tatgtggcag catctgccct gcagaatgag aaggtttgca aatagacttc ccaaacccca   1440

accacagctc gctccgcctc gaggacccct tttctgcacc cccacctcag cgccctcttc   1500

ctgcacccac aaagagagta ctcagtcata ggggttcaac aggagagagg agacagaagg   1560

tacaggcggt gagcaggaac tcagccatca tccccctcag gtccctcccc acccagttga   1620

cagagcgaat cccgagtaat tgttttccga gggggtccgt gcgcgctcgg tggcgccgcc   1680

tcggtctggg ttcccccgag gaaaaatacc cacccgcgag ggctcggcgg cttttcgact   1740

cggcggggat gaactgtggc aacttcggca gcccccaccg cggtgcggaa gtaaagaggg   1800

caacattggc gactgcggct cggaggggct ggagcgcgtg aagccgtggg ggcgccgtgc   1860

gcctcccgct ctctcgtttc ggccgcaggt cctgggactc cgacttcggt gctccgggtg   1920

atagcggctg cggcgcctgc agtccagatc ctcgcagttc tgcgggcgaa ggaggcgaac   1980

ggaatcggcc cccagtgggg agcgcaacaa gccacagtag ccaaaccccg cgctcctgcc   2040

cgggctccca gacgaacgca gccgcagcgg ggggccgggc cccgagcccc acgccgccgc   2100

cgccgcgcca gcggtggggg gcgggctggg ggcggggcgg ccggggctgc cttcccgggc   2160

gcatatgcga gcgcagcacc cggcgttgcc gagccacctc cccgccgcc cgc           2213
```

<210> SEQ ID NO 83
<211> LENGTH: 3060
<212> TYPE: DNA
<213> ORGANISM: Homo sapiens

<400> SEQUENCE: 83

```
ttcccaactc taagctttgg ttttagtgtc catggtgaca catactggct atatcaggca     60

acaacaccac tacagaaaca ctcaagtttt attttatttc tatttcttgg tagcatattt    120

tccgaagtgg tttccttttg catatccaac tctttagtaa ttatgaattg cactttcaaa    180

gccatggcac caaaataaca acaacaacaa caaaaatctg ggtgaggtag ggcaagaagc    240

tttagtccat tagatatgtt aaaccaaact ccattctctt ttgccttcat gtattcttca    300

ccatacatga atctagtctg tctgtacacg tttagctacc ttttagaagc tcttattacg    360

gcaactttcc acaaacaagc aatcctcaaa agctctaatc aaagttgaag gtttgctgca    420

ttggaatttg cttctgactg cacaacacat ttaaatataa tttgagatgt agacatttgt    480
```

-continued

```
gcccagccaa tatccattga cttcaaaaaa aagttgtaaa atcgtaagta cacaattaat    540
gataatatga gatacacttc tagattaaca tttacttgaa atctttccaa aatacttttg    600
agaccattat tccctttctc ttgttattgg tggatgaagg aagaatgagg gtctttcaaa    660
gataaatttt gcctcaaata tactgcgact gtgatatgca gtaagtaaaa atattcagag    720
gcattaattt ttccagaaag ctacccccat aaaacaattc ctccaagcag ggcaccatcg    780
tacctgaaac tttcagagat cagtgtctta actaagatta agctatcctt tttcctacct    840
aaatcaattt cacccaaacg aggcgtttgt gttataattc attgttcccc agattctaaa    900
atcaaccatc tgccatagga gtttctgctc agtaattaag ggactatcca ttagaactgg    960
caagagtaca aagtacgaag gagaagggtg aggcagggga gaaaaaacca cttaaaagag   1020
atagggatat gtgtctcaca ctggcccttc tacacctcag ctaaagtact gtcatccatg   1080
aggcaataca aagttaggac aagcggcaag agcaactcct gccggggtta tcggaactga   1140
aatcacagtg gggatgcagc acgccgggca taccttgaaa gagaaaggct ttcgtcccat   1200
tatgcagccc cgggacctga cgcactccgg tcgtggactc cccaagttct aactctgtta   1260
agacgtcaat ctgtagggaa gggtccacac caagccccca aactggtgag gggtatgagg   1320
tgggagagag aaaaaggaaa agctccatca aaatgcaagt ctcttcctcc agggcagcaa   1380
agaaccgcgt tttcgcgaca atattgggaa ctgaagatga gaggcgactg cctcctcctc   1440
cgccgagagc cttacctgag atcagcagcc aagctttaaa tagcggagca cccagtcccg   1500
tttccatgac ctcctttaaa cccttctctc tgcaaagttc cccctcagcc ctccgaccct   1560
ggactagggg cgtgatccgc ctcgcggtct ccaaggcaag cacagaaaaa aaaaaaatcc   1620
atatccaaac ccgccccctt actccaagct tcccactcca gacctacttt gggtccggga   1680
aaagcgaggc ttccccagcc agcccatgct gccccgaggc gggagccatc cctttcccca   1740
gccccagctc tgcggccact cacctgctcc gagaccgaag atcaaacaga atgttctcag   1800
taagacccga gactccatgg tgcggatcag ctcagtccat cgtctccctc tttaaaaata   1860
aaaataaaaa tcgaagaggt tcttggaatc aagcgggaaa ataacgtttg tctctcctgc   1920
tgctgcctcg gatttactga tcagtaggat taatacgctt tggttgccta agaaagaaaa   1980
gggaggcctc cccaggcgcg tgaagaactt agaccctcca atgcgcacat cattcccaca   2040
cgcagggccg aggcggcagc gcggcccgga gggggcccgg agggaggggt cggactcgcc   2100
ccggcgcggc tccgtcgggg aattagctcc cgagccgaat aaaagcagcc aaagactcgc   2160
acacccggta gaagggggc ggccccaaga aagcccgggc tggggcggcc ccgcaccccc   2220
ccgtcttccc cgccgcccga acctgttgta aaggcagaga caatggagaa agctccggga   2280
gacgcgcgga gagactgctc ctccggggag ggaggggcgg gccgggggag gcggggtaag   2340
gaggagggag gggccgccga gggcgaggcc ggcgctcagc gtcggtctcc cgcacggtct   2400
cctggatgcc aaacccggtc tagggagccc aggagccgtt gcagcctcag ctcttctccc   2460
tccctctctc gatgacccgg gcaatgccaa cctcctttcg ggattgaaag ctctaaatcc   2520
aaggtgctaa gttgatgggc ggtctttgct ctcacccctc gatttcgggc gcgtgtcttg   2580
aaagacagga gagaaaaaag accacccagc tgcaggaggc aaggctggag cgagtagcgc   2640
tcgcctgccc tttaagcaaa ggagggaagc ccatgtgcac tcgtgcactg ggctccggag   2700
cagccccggg gtgcagggca ctccccctcc agggcgtgcg gaggaaggcc accaaaacac   2760
gctgcactgc cgaggtggag ctgggcaaag taggtagaga ctggtgggga cggatggcga   2820
gcctgggaag ccccgggtgt cctggtggag aggttccctg ccgggggcgg ggcgctggag   2880
```

agcttccccg gcgcggagag cttcccgggc gcggagagcg cagagaactt ggccaggagg 2940
tgctggacag ctccggaacc cgcgcgcccc ctgccaaata aagcgtggag acccggactc 3000
gggctctctg ggaccagcat acagcagaag gcaaggggaa ctgagccagg gcgtctgttc 3060

<210> SEQ ID NO 84
<211> LENGTH: 12653
<212> TYPE: DNA
<213> ORGANISM: Mus musculus

<400> SEQUENCE: 84
aataccaacc tctcaatgtc tccaattttg agtatttatc ttctcaaact tggatcttcc 60
cctggctgtg gactgacttt gaatcctggc caatgacttc tccttacttc tcctcactct 120
gagagccact gtctgaaagg aagtcagctt ggagtatccc tagaggccaa caggacaagg 180
cagtttgctt gtgtccttga tgactgtcta tcagaaaaac caggtgttcc ctagaaacta 240
tgttgcttca tttattcaat aagcaattat caaacctcta aatgttccag gcactactct 300
ggtgaaacga aattgagatg aacgagagag acaaacctcc tactcatggg gcactggtat 360
tatggttggg gagatagtga acacacaagt aaatgtgtaa ataatattac ttacggtaat 420
cagacacatg ggaagaaaat gaagctgaga gccctggggg ttgacaagag ggattctgct 480
ctaggcagcc tctgcccagg gagctgactt ttcagcaggg atccaagact catgttcaaa 540
gccaagtaca cagggtacat cctagcacga tgaaatctta acctgcaggc aggacaaaaa 600
cctgcctcca gcttgatttc ttcgtgccct gcaaccaaag catgtggtat cttcacaata 660
ccaatagaat ttctttatag tttatgaagt agactgtgac ctttatggta tgactgactt 720
gtaagggcaa gcatggaggc agtgaggaca cccagaaaga gataggaatg agttggaggg 780
ttgggagccc cggggctgct gagaaaacca cctttcctca cagattctgg cagggtttta 840
tgatttacct gtaggcatag ggtagttgtg ggttatttga ttgggccatg tggtgaaggc 900
cagtgcgttc tcttagaagt tgtcaggaaa caagtttggg caaccagaaa ccaaaaatcc 960
ttacttggtc atcattacag ccatcactaa ggaattttcc aaaatatata attcacgtac 1020
tccatgattt accaaagtac acaattcaat gttttatata tatagtgata tctctgagag 1080
ccatataccc atcaactttt taccatcatg attttatggt tcccctaaag taaaccctac 1140
gttctttagc catcattctc cagatcctcc tcctactcac tcctcatcca gaggcagcca 1200
ctcatcagct tcctgtttct atgcatttgt tttttttctg gagacgtcac agaaatggac 1260
tatatgccaa cagaaatcca ctgggcctat tctctgctgg accaacaggt ctaccgcccg 1320
ccccttcccc acgtccccac tcaggaaagc gtgtacttac ctgagtggac tgaggtcctt 1380
agttatctag ggaagattta tgagcttgtt gagattaact cttgttactg ctaatggctg 1440
cgaagctgca gagctacgac agaacatatg tctcacttaa ttttttaaat ggaacacgct 1500
gaaaccctca tcccacagga ccagctacac agtcttgacg attagggttc aaaagataca 1560
agtcccctgc tgggaccact gtgcctctta gggcttctgg gatttctgag atcaagaaaa 1620
ggggactagg aaaagcactt cagagcccct aaaggccata gaagtgcatt tatactgagg 1680
gagagttgag ggtgggacat ggttctcaca atatatagct tggcatccgg agtccttact 1740
taggaggccc agtgaaacat gggaaatcta gttttctgca aggggtgtgt gtgtgtgtgt 1800
gtgtgtgtgt gtgtgtgtgt gtgattttaa tgttggcatc acgtgcagca tgctccagga 1860
ggaagagaaa gcctcgactc tgtaatgaag acacaggagg aagggtctgc tctggggcca 1920

-continued

```
agttgaattt tgagaatttt ggagagtaaa gggctatgga gacagattag ttggtagact   1980
gcttgcccag gatgcacaag gaagcaggtc ccatccccag cactacataa actaggtggc   2040
ccagacatat aaccctagca tttaggagat gaagggacag gaggttcaag gttcaaggct   2100
agctccagat acataacaaa gaaaatattt gggagctgaa ataaagttca gttgacacaa   2160
ggatccagga cacatgtcac aatagattgt aatttcagca gcagtgcatc caacattgtc   2220
ttctatcttc caggggcaca cacacacaca cacacacaca cacacacaca cactcttaaa   2280
agctggagag ttaagccttg acatccactc tgtaatggcc cagttcagct gcattgcagt   2340
gggtacttct caggctgatt tatctttcat gatttctttc ttcacctgcc ggggaaggta   2400
cgaacgggga gcaaatgggc aagggggtgt atacagaatg tcctgaaaaa taggatcaag   2460
gtcagaggac catgtaggtt aagacctttc ctcttcataa actgtgcaac taaattggtg   2520
accccccact ggactcctgg ggtcaaaggt atgtgaagta aaggccctgg gagcacagag   2580
gatgggcaaa tgccagagag aaaccctgga aagaaagcag agctcttttg ttgaactctt   2640
tccccccccc cccctctggg atctgggagg ttgttatgag tttaagtatc tcagagtagt   2700
attggatgtt gggggaagct ggagccatag atggagccac aggacaagct ggggtgcggg   2760
aggcttcgag tcacatggca tgaacatgta agctggaggt actgaccttt caggttctgt   2820
gactgcatca tctctagata gactgaagca cacagtacag ggaccctagc ggggcggccc   2880
cagtagcaga gggtacacta gacaggagag actcctctgc ttgtccactg gtcgccagca   2940
aagcccagct tttctctcta cagaatggtg ttccagtagg ggtttccaaa gaaaggagag   3000
agagagagag agagagagag agagagagag agagagagag agagagagag accgagacct   3060
aaacagcggg ttttggagaa aaccatccag aaagtcacac aacagccaaa aaaaaaaaaa   3120
aaaaaaaaaa aaaaaggttt agaaggttta gaacttcccc tatgtggcag catttggcct   3180
gtagaacgaa gctagcaaac acttcttaaa ttcgagccat agattgctct aagctcaggg   3240
actcccacct caacaccctc aaccagcact cttaaaagct agtatccagt cacaagagcc   3300
tttggctggg actagacagc aagtacaggt ggcggttggg gactcaggca tcatccgtcc   3360
cctgcccccct cctccgcccc cacctgctcc tccccaccca cttgctggag cgaatcggta   3420
gtagttattt cccaaggagg tgctgggagc acttctcgac accgcctagg tctggttccc   3480
ctagggaaca aaacccacgc acgcaggctg ggcggcttcg gacccggcct ggatgaactg   3540
ttgcaacttg ggcagcccgc agcgcggcgc agtggcagag gcgggggcgt gaagccgtga   3600
ggcgcgggta gccgggatcc ttgcatctcc ggagtccagg aggcgagcgg aatccgcaca   3660
gactcccagg gcaacctgcg ggagtggcgg agccccgcgc tcccgcccta gctcaggggg   3720
agcgcagctg cagcagggtt tagggcccca gccccgtgcc accgccaccc gcggtggagg   3780
gtgggctggg ggcggggcag tcggggttgc tttcccgggc gccgccgagc cacctcccct   3840
gccgcccgct agtaagtttg gccgcttcga gcccacagag ccgcggcttt ctgtatcagt   3900
caacactgtg acataagcaa aataagaagg caaagcagac tgcattagag aaaacacact   3960
gaaagttaaa accatggcga aacaaaccca tgtcactcct tgtttctcaa gacttatatg   4020
cagttacctg acttgagaaa tgaaggcata aatttctact tcatgaatca ttatattaac   4080
atgtaatata ggtaaatgat tgatataatt ttctagaaga tagctaataa agatgttgaa   4140
gatcatgctc aatagtcaaa gattgaagga ggtagccaac taagtttctt tgtagtgaaa   4200
aattacaaat aatgggaaca gattgaggag tcagaaatgt ttttcccaga aggagtaatt   4260
tggtgaacac ttacaaatta gcttctaaga aatgttataa aagaatacaa gggctatggt   4320
```

-continued

```
ttcaaagaat agtaactaaa atcagcaaag agataacaag actaagacac acagacatgt   4380
gccccgaata gcttcatggt gtgagctccc aagaatggat agcctcaagt atagtctttg   4440
taacttttag ccttagctgt tacagtatgg gtagacttta tgtcctttag attatcttct   4500
acccctaagg tttaatttta aaaatactca aaaacataac tgtagggaga taatgggagc   4560
taggtcagtt attcttctaa aggactcaag ctcagtttct agcaccaaca taaggtagtt   4620
taccaccacc tgaggcttcc actccagagg atccagtgac cactgtgatc tctataggaa   4680
cacacacaca cacacacaca cacacacaca cacacacaca cacacaatta ttctttaaga   4740
aaggtaaatc tttaacaaaa ataactgtat ccataaatgt agccaaagtc cttacacttt   4800
agcttcccca tcaacagaaa tatgacactg gtttgataaa tagataatag acatgctata   4860
agcactcagt cttaatgtcc agtgatattg acctccagtg ccttataact gagtttccaa   4920
gactaatact cctgaaattg gaatgtgtct atcatttgat gaactgtttc atggaggaag   4980
gtgacaactg gtcataagct ctgcaaataa gcaacgtaaa gacttgtgga agcaaaatct   5040
tttgaaactc tcaggctcaa ttataggctt agagatgatg ctgtactgtg tgatctctat   5100
aaagcactta atgtctctgg acctcattta attcttccca tatcccttat gaatgggaca   5160
tgtatgaaag taggcagtgc atttcagtgt gtttgccggt attcttgtat attaggacaa   5220
tgtacttaca tggtttccac tgaaatgggg ttattgtctt attgattgtc atagcacaca   5280
atacaatgtt ttcattacat tttcacacac acacacacac acacacacac acacacgcac   5340
acaccactgc agttttctct tatttcccct catttcccag gtttttttcca ctttccactt   5400
cttgtctgtt tccccaccac tctggaatga attcttaatc atattcattt taactgctta   5460
tattagctct aatcctgaaa cagaaacatg tcttttctat taattaattt atttattcac   5520
tttacatccc aatcacagcc actcctacca gttccctttt atattgcctc tcaccagtat   5580
cacccctatt ctcctcagag gaaggggagg cctgtcctgg gtaccaacct accctggaag   5640
atcaagtcac tgcagtgcta ggtgcatcct ctctcactga ggccagacaa ggcagcacag   5700
ttaggggaac agaagtcaca cactggcaac cgagtcaggg atagcccctg cttcacagaa   5760
acatattttt aaatattcaa agaacatact gatgtttatc ccttgggtac acttagcaat   5820
gtttccattt tgacttggct ggctccagga aagaaaggct gtgcctgctt tgaacaagat   5880
gggaagtaga caatatagat tcagagctaa gaagtttatt ctgtgagctc tatggtgcat   5940
ttgcaaggct tgatttttgg agtacatctg tgcatatgtt ttcctaatca caaaaccttc   6000
ttgaccttac ttcgcaacag gatgggaaga tattctgccg gcggacagct tgtgattgcc   6060
agaatccaaa tgttgacctt ttctgctgcc cagagtgtga caccagggtc actagccaat   6120
gtttagatca aagcggacag aagctctatc gaagtggaga caactggacc cacagctgcc   6180
agcagtgccg atgtctggta tgtcctgtcc ctaaggatcc tggtgccttt actgtagaaa   6240
acgttataaa cttgagagct tttgggcagg agttccaaga tgttcccagt attatacaga   6300
gtatcatggg ttatgcttaa ccagtggcca tgtgttatgc ctggagatat ttacattgca   6360
tttaaaatgt tgcaaaagta aaaataatga atttatagaa cagatttaac ctgagcagtt   6420
tgtatatacc tatatacttt agcaaagaaa attaaatggt ttgagaggta gtgattgtcc   6480
agacagagcc aagtgtgttt ttgtttttga cataatcctt aatattgcca atagaaaaaa   6540
aacataatag aagtgatgga gtttgggtga gcaatagtga gaatccaatt ccataattgt   6600
ctcctaggtc agcttgatgt agacactttg gatatatcaa agcatttcag tggttagtct   6660
```

-continued

```
tttccataaa agtaccagtt caaagattct tgagaagtta agagaatgtg tgtgaaagat   6720
aagtaccata ttcattgtac agcaagcact tggctgagtg tcacggaaga tctccttaat   6780
gtggcaacta gtactgatgc tctgatatcc cttgaagatg ctgctcaaac agaacaaata   6840
acattatttt aaatattaat atacaggtat taatactgtg cctggatttg gggaagttca   6900
aagaaaacac acaatttcca tatctggttc aatgtgtttt aaactactgt acagacaacg   6960
atttctaaga cttgagggca cggtacattg agaactgcgg tgctccatct gctccatctc   7020
ggagcattct tcctgagtca gcttataagg aaagctttta gattggtgct taatatttat   7080
tgaaatgaat ttttctcttt ctgtgtatta tataaaatct agcacccaga gaacttgttc   7140
tctaagtttc cataaatccc caagttaacg tgcaagcggt catcacatgg agcctttaca   7200
atccatctta atactaagac tgcaacatag ataaattctg ttcatgtgca actttacaga   7260
ttcccttcca aggacaaaca cattcaggat aactgtagac ctgtttccag tgtcattctg   7320
gaaaaccatt tttcttcctt gagaagccag tcatcagata gctgggatta ctggcattta   7380
tcttctacgt gacattttca ttcaaagagt ttcaaaaagg acatcttgaa tgtccagtct   7440
ttgggatgta catttatttt tcaactcaca gaagctattg agcattaact taaaattcct   7500
ttagaataat atcggtctca tttatgaaat acttcatcaa gaattgcctg tgccagactc   7560
ctagtgatat acaagcaagg cagacacagt cacagcatga ataagcctag aatatggaga   7620
cattgactga ataattaagt aaatgagaat cactgcagtt gacagggcca tgataacagt   7680
gaacctgtgt ggagaaacct cgttgccata ggcagctcag tggtgcctgc ggtcagaaga   7740
ggactcaggt agaggctcca tttaagctgt gatttggaga ccttagagtg atgggatggt   7800
ttgtccagag aacaaccagc ttcagctctg aacttgaatc ctgcatccca gctgatgcag   7860
ctgttgaaat attccatgtc tccaggtctc cctttggacc tgaaaagaag tggttatctc   7920
tttatacact accctcacgc gactatctga ttgcttgttt gttctattag tatctgttaa   7980
acaaatctct gaacatcatc agggaagaaa acaaacaata caatccaaaa gttcaagtta   8040
atgttgaact caacacttac caattatgca gcataacctg aaaaaacaaa cagtacactt   8100
tgatgaaaat aactatattc cgtgcttaga acacaaacaa gctaattaaa gactgtctgt   8160
gaactgtggg ttaggtagtc agcaaaacca tcccgaggaa gtgatatctc cttaaaaggt   8220
atgtgtgtaa aaggtatatc ttcacagagg aggatggatc atacacatta gggttccggc   8280
tggaagcatt cagtaagaaa ataatgagat ttgtaacact ttccttcccc caagggatac   8340
tgggaatata aaactgtgta aggatgagga caacttattt catctttctc tccacaggaa   8400
ggagaggcag actgctggcc tctagcttgc cctagtttga gctgtgaata cacagccatc   8460
tttgaaggag agtgttgtcc ccgctgtgtc agtgacccct gcctggctga taatattgcc   8520
tatgacatca gaaaaacttg cctggacagc tctggtattt cgaggctgag cggcgcagtg   8580
tggacaatgg ctggatctcc ctgtacaacc tgtcaatgca aggtaaccat cagccctggg   8640
ggttgtgagc cacagagagt ttccttttga aatctctgga ttcagattcc atggagtgta   8700
tgttctcaca ggaggacatt aagtgtagac agataagagc tggtcctcgt ataaaggcag   8760
tttccaaatg gacgtggagt aatacaaatt tgccttaaca ttactgaatt ttaaccactg   8820
actaatctta atcccagaga atgaaagtta ttttaatctg caatatagaa aaataatggg   8880
agagaacaga gggaagggga gggaagagag agcaagccta gaaattctta actttattct   8940
agaaaattac agaaaccatc agtagtgtca gaagacagag atctatatag gagcttattc   9000
tgttttattt tgccttgcca accatattcc tgaatctctt gtaatttttg actgctatta   9060
```

-continued

```
tgtgtctgat tttttttgg aagatttccc ataaaatatc cccctgtgtc tttcagactt   9120
gaaaggtggg cctccctctc ttcagtgttc atagagttat gaccacaggc agcttacagt   9180
gatgcttcat caagcacagt caaaatctca ggcagagcat tgtgttgaga ttctcatgat   9240
taagatcatt aaaaatgata gtgcacttgg tcccatcaaa gcctaccccc acctcagcca   9300
tcaatggagc ctttctagct tgtcattttt tagatttatt agtatagaca cttttctgtt   9360
tcctagaatg tagtatatta agattaattc ccaatagaaa aataatgtca ggccttctat   9420
agccaaagag ccacgatccc catctggaaa ttcaccaacc acaatcaatg tggccaagag   9480
acataggcac ctgagttgtt caatttcatt tcccccattt tcttttattg aaaatggatt   9540
tttttcatac aatatatcct gattatagtt ttccctccct ctattactcc aagtttctct   9600
ctacctactc tcacttcaag gtccacctcc ttcctgtctc tcctttgaaa acaaacagga   9660
atctaaagga taagaatttt taaaatcaaa tagaataaga ttatataaat acattggaat   9720
aggacaaagc aaatagaagg aaaagagccc cagaaaatgc acaagaaaaa agtagatgca   9780
gagatctatt tgtacactca ggactccagt aaccagaggc cataatattt acacaaaggc   9840
tgtgtagggt aacatattaa agtaaaaata aaaactaaac taaactttaa acaaagagac   9900
aaaaagctct gctatgacat tatgagtcaa ggtaacagca gagatgccat tgcattgatt   9960
atctattgat tatctattgg ctgtctactg ctgggcatgg agcctaccct taagattatt  10020
tgtttccctc atgagactcc cttagagcaa aagaaatttc catttgtatg tggtaggtgt  10080
gtgtgtgttc acttctttca gctctgtgta gtccccgtgc ttgctacctc aatctcagtg  10140
agttcatatg ttcattggta atattgtttt gaaggccttg tttggggtcc tttatctcct  10200
ctagctctta ccttctttct gtctcatttt ctgtgaggtt ctttgttcct gaggaggaat  10260
ttgatgcaca tgttccactg aaggctaagt gttctgcgat ctctcagtct ctggatactg  10320
tttggctttg ggtctctgta ttttctcatc tgcttcagga ggaagcttcc atgatgctgg  10380
ctgaacaaat cattgagcta tgagtatggc agaatgtcat tcagagtcac tttatttcta  10440
cttctttttc tttagatcag catagacacc atctcaattc tctataatta ataaggtgta  10500
tatgtgtttt cgctatcaat ttatggagag caacctacat agctttggta atagcttagg  10560
tagtttggga attcccatgg actcctttgg ccagcaactc aattagatat aattcatcca  10620
ttcccagcac tggaagtacc atttagtgat aagatatgtc cagttggaat ttagatatcc  10680
tttatatatg tttatatcat aggagcttct actagatagg ttacaatatg acccctcaaa  10740
ttgccccagt aaagatgtcc ttccctgtat ttccttcttc atctatcccc cttctcattt  10800
gatcctcctg ttcttgtcca tccctaaaca gctcttccat ccataactat atattctatt  10860
tctccttccc agggagattt atccatgcca tctagtccct tactctttat ctaacctcta  10920
tggttctatg gatagtagct tggtccttac tcattgatca aacagctact atacatatac  10980
gtgattacat acacacacac acacacacac acacacacac acacacacac acacacacat  11040
atatatatat accatactta tccttatggg tctggactat gtaactcaag atgattattt  11100
tctaactctt tctgtttgcc tgcaaatttc aggatgtcag tagaactaga tcttgaggta  11160
gatcgtttcc catctatctg aggaaccatc atattgattt tcatagtagc tgtacaattt  11220
gcactccaac tagctagcaa tggaggagtg ttccctttag tccacatctg taccagtctg  11280
aactgtcacc tacattattg gcccgacagg tataagatgt tatctcaaaa aaagttttaa  11340
tttgcatttc catgattgct aaaggttttg aacatttccc agtcatttga atttcctcta  11400
```

-continued

```
ataagaattt gtttagatct gtatccaatt tttaaaatta gattgtatgg tttcattttc  11460
atatctagtt tcttgaattc tttatgtatt ttgaagatat tgtagtttaa ccaatttaag  11520
cttatcccca cctagcatat atataataaa tgagattatg ttcattttat ttggctttca  11580
cagttactgg ggggtagcct caaatctact gttctaactg ctgacttggc tgcctcccca  11640
gtggtgtatc tcagacactt gctgttcctc tctcctcatg gcagcttcct ccctctctca  11700
gttcttcctc cttcttcact ttgtctctcc tctctgcttt ctcttttcca tgccccagcc  11760
aggtcaaatc ccacctacct ctaatccctc cagtatttgg ctgtagccaa ttttattaaa  11820
ccaatagttt taaatcaagg aacaaggttt gcacagcaaa agcttgtaaa tgtggaaatt  11880
cactttccag gccttgtcct tcctttcagg tacagaattt agcattacaa cgcacagcaa  11940
cagaccaaat ctcaacagaa tagtagatgt ggagttagaa aacaaaaaaa caaaaaacaa  12000
aaaacaaaac cttttcccat tccatagaca gctgctatta gttcaaggtt attccccagt  12060
ttctcatcta tcaggttcag tgtatataga tttgctttga agcatttgat tatttggaat  12120
tgagttttgt gcagggtgat aagtattgat ccatttgtat tgttttagat gctgccaatc  12180
agtttgtcca gtatcatctg gccctggact tttgggggga taagagatat ttaattactg  12240
cttctatttt atgaggaatt atatatctgt ttagattgct tatctgatct tgattcagct  12300
ttagtaggtt gtatatattg agaatattat ccatttattt cagatttttc caatttggtg  12360
gaatacagtt attaaagtac gttcttatga ctctctggat ttctttggta tctgttggta  12420
tgaaccacat tgcaattgaa attttattat tttgaatcgc gctatctttt agttaatttg  12480
gctctatctt ttagtcaatc ttattgatat ttctcttata accaactttg ctttattgat  12540
ttttttgtac agttttttat tactatttta ttttttgttc agccctgagt ttgattattt  12600
cttgtcctct actcttttcg gttgtgattt tatctttttc ttcttattat ttt         12653
```

<210> SEQ ID NO 85
<211> LENGTH: 3000
<212> TYPE: DNA
<213> ORGANISM: Mus musculus

<400> SEQUENCE: 85

```
tcctgtgtga gattagactt ggctctttag aggaagacct gctccgttgt tccccatggt     60
gggtaccaat gagaagaggc agttcatggt gttaaggcat ttattgtaga aaggcagaga    120
gaggtagaga gtagagaaat agaggccggc catggccacg tggagagaag gggaagggaa    180
tgcagagaga gggggagcaa gagggcaaga gagaggcaac agttagagag taagagaggg    240
aaggaggagc aagcagcccc ttttttatag tgggccaggc ctacctggct gttgccaggt    300
aacggtgggg cagagcatac ctggctgttg ccaggtaact gtgagggtgg agtccaggca    360
gaatacctgt tactgatggc catacacctc tgggtgggtg agggtggggg ggtcggggag    420
ggtaaggtgg ggatggtgtg ggagggcctg tgggaggctg tagctgaggc aggagccagg    480
gtttcaaggg gcgtggccaa acacctgcca tttcttgtag acagtcacct gcttgatctg    540
agcttgacca gggaccaagc tgcatatcac agctcactgc cccacacttg tgtggggaag    600
ggaatatttt agttggcttt agaaaatgag tcttcccccct atgttccacc agagaggagc    660
aaaatgaaga tgtaaattgt ggttatgaaa gattatttta ctatcttgaa aacaataatt    720
atgtagtaat ttcattttat gagttaaata agagagggtg acataaaaga aaagtcagat    780
ggaaggaaga ggttatttgg gaaatgcaaa ttttttgctt ttgattctaa atgataagca    840
ccaaatgcat atttttatat tgtcctgaag aaatctttcc cattgtttcc ccaaaatgat    900
```

```
cctccaatgt agatcagaat tctaaagtga agaaacccaa atagttttgc ttacatgtgc    960
aaactttaca atttaatttc caattggttc attcttattc cattacattt ttgtttttat   1020
ttttattatt ttttcactgc ccatatttat agggtatgct gtgggttttt aatacatgga   1080
tccatcatga caagatctaa ttaggataat tagcatatgt ctccttaagt gtttatcttt   1140
tgtgtgtgtg tgtggtgaga ctattcaaaa tatgctgttc ttttgctttt aaaacctgca   1200
gtgcattgta ataagctata gcaggcccac tgtgtgatag ccccactgtg tgatgggaca   1260
cttagcttca ttcctttctc cgttactcag caaaggagtt cctccctcac cttctagtct   1320
cctcactgtc cccagctttt cataactaat tcttttctct aattttatga gatcataatg   1380
ggatatctat tgccatttaa aataatgaat cctgccctga cttggttttg tttctgtttt   1440
gttacagtgt tcttaggggt gacagatctc caagccaatc aggttgaaat gacaagcttg   1500
tgtgctcggt ggcaaataca tcgccatgcc acagcctaca ggatagttct agaatccctt   1560
cagggtaagt acaattttgt gaagtactcg catgcctgcg tctgtgcaga tcatcttgga   1620
aagtcatatt tacatgctca gaagatgcat gtagaagctt atccatcaat gctttgcatc   1680
cacaagctcc taaacaatgc aatctgctgt tggtctcagg agccaaataa ccagaactag   1740
catacattca aattgcacgg tgctagcacc gtgttaccca ctccatggcg accagcttca   1800
aatggcatgc ttttctgagt gtttctttgc cttggtggta acttgtgaac acattcttat   1860
acaggaggag gcatcatgtg tccatatctg ttgaggtttg gtctgacata taggagttca   1920
aaatagaatg aacagtgaag acgagaaaaa cattaaaaaa gatatacatt ctatggttgt   1980
gtgaaatgtg agttatggat gtttgagaca aaggagatga aagatatgcc tactatgagt   2040
ggaggaacaa ctacagaatt tgagttttat ttcatatctc tctatgatca tacttaatat   2100
agaagggtta atatttactg tcatttttag gcttaaagat actaagctta atatcacact   2160
cccagacggt cccgcaacaa tttgatccgc atgttttaag aatctatgaa ggaagtataa   2220
gttactctag tttggaaaaa tatttaaccc tttgggttga cagtaatatg tatgaaaatc   2280
agtgcaatca atggaactac tactatttag aggtattttt attcaagatt tttagcgcaa   2340
tatctttgca gagaagcact gagactcttt accagaagat atgattagtg tgtataactg   2400
ttgatctgta gtcccaaacc acagagagtt ctttcctaac ccaagaccct ttggtggcta   2460
cataatgaat caaagtgtgt aagtaagtct ttcacacgcc ctcagaatga ctttcaggct   2520
gcaagaagcc tttcaagcag catcgctgtc atgttgaaag gaatggacag aagtgttgtt   2580
tcatttactc cccatcatcg tttgtagctg aggaactcgg acgttggatt agctctgttg   2640
tctctcaccc aatggtgttt atcagcaaca gattctaatc tacagctgct ggaaaaagaa   2700
tttggtcagg gagatgtggg agtagctgtg gggaaagcat ttcttttttt ttttttaat    2760
taggtatttt cctcgtttac attttcaatg ctatcccaaa agtcccccat gcccaccccc   2820
ccccaatccc ctacccaccc actcccccat tttggccctg gggttcccct gtactggggc   2880
atataaagtt tgcaagtcca atgggcctct ctttccagtg atggccgact aggccatctt   2940
ttgatacata tgcagctaga aacaagagct ccggggtact ggttagttca tattgttgtt   3000
```

<210> SEQ ID NO 86
<211> LENGTH: 8622
<212> TYPE: DNA
<213> ORGANISM: Rattus norvegicus

<400> SEQUENCE: 86

-continued

```
ggaagaaaac caagagcaca gagaagaaca gcaagaaagc ccacctacac tgagtagagg      60
cgcctgggca gagagagcta ggaagctgag atacaagggg ggcttgaaag ataattggat     120
tgatataaaa cagtgaccac agcaggattt ggggacaagg gaatacggtt tgataattgc     180
cttttaaaaa tggtgggtta ccccttcagc agtcatgcca gtattgcacc aacgcacaca     240
cctcgtgtct gaccgacaag tcgtgtaaca tgcaggattc acagctgtgt aagatcgctg     300
atgacaatgc tctcccagtg gcctgcagag ttcatcccag cacgatgaaa tcttcgccag     360
caggcaggac aaaaactggc cctattccga cttggtttgt ttgtgtcctg cggccaaagt     420
gtgtggtgtc tccacagtac caatagaatt tcgtacagtt cgggaagcag actgtgacct     480
ttatgaggtg actggcttgt aaagggcagg caagcttgga ggcagtgagg acagccagaa     540
aagagatatg aatgggttgg agggttgagg gcactggggc tgctgagaaa accacctttc     600
ctaacagatt ctggcagagt ttacggttta catgtaggca tagggtagtt gagggtagcc     660
aggcgttatt tgattgggtc atgtagtgaa ggctagtgct ttctcttaga acttggcagg     720
aaacaagttt gggcaaaggg agaaaccaga aatcaaaaat tctacttggt catcattata     780
gacactatta aggaattttc caaaatacat attccagata taactcacat gccacatgat     840
ttaccaaagt acacaatgta atggtttttt agtacattgt gacgtctacg aaggccacgc     900
acccatcaac tttagaacat tttatgacct ccaaaggaaa ccctacgttc tctagccatc     960
attctcctcc tcactcctca tctggaggca aagtctcatc aactttctgt ttctataaat    1020
ttgatttttt ctggagaaat ggaatagatg ccatgctgtt catcgacttt gctgaggaga    1080
ggtgaaagaa acatttattt accccaaacg aggagggtgt atgcagaccc aaggaagatg    1140
ctaagtctaa actgtgaaat aagtgaaatt cttgctatta cttatgaagc catgggggat    1200
tcacaggaag ttttatcact ggaaagttcc cgtctccagc caccgaacac ctactttttt    1260
tgtggcattt tatctctagg gaatttaagg taggcctggt tgggttcggg gtacaagcct    1320
tgttactgtg aggaacacca ttgtgtggta agcacaacag aaattcactg ggcctattct    1380
ctgatggacc aacaggtcca ccccttcccc catccccact caagagtgta cctacgtgag    1440
gaaatcgagg tacttagtta tctagggaag atttatgtgc ttgttaagat taacttgtta    1500
ccgctaatgg atgcgaggcc gcagagctat gacaggacat atgtctcact taattttttt    1560
aatggaacac gcggaaaccc tcatcccaca ggaccagcta cacagttagt cttaaagatt    1620
aaggttcaaa agatacaagt cccctgctgg gaccactgtg ccttttaggc cttctgggat    1680
ttctgagatt aagaaaaggg gctagggggg ttgggtattt agctcagtgg tagagcgttt    1740
gcctagcaag cacaaggccc tgggttcggt ccccagctcc ggggggggaaa aaaaagaaag    1800
aaagaaagaa agaaggaaag aaagaaagga agaaaggaag aagaggggct agggaaaagc    1860
actctgaagt gctaaggaag tgcatttttt gagggagagt tgggggtggg tgggacgtgg    1920
tcctcacagc acagcttggc atccggtagc cttacttagg aggcccagtg aaactgggga    1980
atctaacttt tttgcaaagt gtgtgtgatt ttagtgttgt cattgagtgt tgcatgcttc    2040
tggaggaatg gaaagccccg actctgtatg ggagacacag gagtaagggt ctgctctggg    2100
gccaagttga attttgagag tgttggagga tagactatag acacagttta gttggtagag    2160
tgcttggccg ggatgcataa gtctgtgggt tccatcccca acactatgta aactaggtgt    2220
ggtggcccag acctatgacc ctagcactta ggaggtgaag ggacaagagg atcaaggttc    2280
aaggttatct tcagatacat aacaaatggt cctggacaca tgtcacaata gcctgtactt    2340
ccagcagtgg gacatccaac atcctcttct gttctccaag ggcacacaca cacacacaca    2400
```

-continued

```
cacacacaca cacacacacg cacacacaca cacacttaaa agctggtgag taagttgggc   2460
cttgacctcc acttggtaat agctcagttc aattgcactg cagtgggcac ttcttgaaat   2520
gatttaactt ccatagttcc tttcttcacc tgcccaggaa ggtcatacat gaagtaaatg   2580
gacaagggca tgtatacaga atgccctgaa aaataggaca aagttcagag gaccatgtag   2640
gtaagacctt tcatcttcaa acgttgcaca gctaaattgg tgacccccca ctggtctcct   2700
ggggtcaaag gtatataaag ttaagcttct gggaacacag aggatatgca aatgccagag   2760
agaaaccctg gaaagaaagc agggctcttt tggagaattc cttttccttt tggatccctg   2820
aggatatatg ggtttaggca tcttaaatag tattggatgt tgcggggagc cggggggggc   2880
atagatggag gtacagggca agctggggct ccggagaccc agaggctccg acctacaggt   2940
tctgtgactg catcatctct agatagactg aggcacacag ggactcttgc aggtcggttc   3000
caggttccaa taacagagga tactctagac gggagagact cctctgcttg tccactggtc   3060
gccagcaaag cccagctttt ctatctacag agtggcgtta cagtaggggt ctccaaggaa   3120
agcaggggag agcggcccag agagccagtt ttgaagaaaa ccatccagaa agtcacaaat   3180
ggtttagaac ttcccctatg tggcagcatt tggcctgtag aacgaaattt gcaaacactt   3240
cttaaattcc agccatagat tgctccaagc tcagggactt ccacctcagc accctccacc   3300
agcactccta aaagccagaa tccagtcaca agagcctttg gctgggaata gatagcaagt   3360
acaggtggcc gttggggact caggcaccac tcatcccccc ccccccccac ctgctcctcc   3420
ccacccactt gctggagcga atccgtagta gttgttcccc aaagagggtc tgggagcact   3480
cggtgacacc gcctaggtct ggtttcccta ggaaacaacc cacgcaccag ggttgggctg   3540
cttcggacac ggcccggatg aactgttgca acttgggcag cccgcagcgc ggcgcagtgg   3600
cagaggcggg ggcgtgaagc cgggaggcgc gtgtaaccag gatcctcgaa gctccggaga   3660
cccggaggcg aaaggatccg cacaggaacc cagggcaacc tgcgcgagtg gcggagcccc   3720
gcgctcccgc cctagctcaa ggggagcgca gtcgtagcgg ggttcagagc cccagccccg   3780
tgccaccgcc acccgcggtg gggggtgggc tgggggcggg gcagctgggg ttgccttccc   3840
gggcgcgatc cccgagcgcg gcacccggcg ccgccgagcc acctcccctg ccgcccgcca   3900
gcaagtttgg cggcttcgag cccagagagc cacggctttc tgcctcgtgt ctgaccgaca   3960
agtcgtgtaa catgcaggat tcacagctgt gtaagatcgc tgatgacaat gctctcccag   4020
tggcctgcag agttcatccc agcacgatga aatcttcgcc agcaggcagg acaaaaactg   4080
gccctattcc gacttggttt gtttgtgtcc tgcggccaaa gtgtgtggtg tctccacagt   4140
accaatagaa tttcgtacag ttcgggaagc agactgtgac ctttatgagg tgactggctt   4200
gtaaagggca ggcaagcttg gaggcagtga ggacagccag aaaagagata tgaatgggtt   4260
ggagggttga gggcactggg gctgctgaga aaaccacctt tcctaacaga ttctggcaga   4320
gtttacggtt tacatgtagg catagggtag ttgagggtag ccaggcgtta tttgattggg   4380
tcatgtagtg aaggctagtg ctttctctta gaacttggca ggaaacaagt ttgggcaaag   4440
ggagaaacca gaaatcaaaa attctacttg gtcatcatta tagacactat taaggaattt   4500
tccaaaatac atattccaga tataactcac atgccacatg atttaccaaa gtacacaatg   4560
taatggtttt ttagtacatt gtgacgtcta cgaaggccac gcacccatca actttagaac   4620
attttatgac ctccaaagga aaccctacgt tctctagcca tcattctcct cctcactcct   4680
catctggagg caaagtctca tcaactttct gtttctataa atttgatttt ttctggagaa   4740
```

-continued

```
atggaataga tgccatgctg ttcatcgact ttgctgagga gaggtgaaag aaacatttat   4800
ttaccccaaa cgaggagggt gtatgcagac ccaaggaaga tgctaagtct aaactgtgaa   4860
ataagtgaaa ttcttgctat tacttatgaa gccatggggg attcacagga agttttatca   4920
ctggaaagtt cccgtctcca gccaccgaac acctactttt tttgtggcat tttatctcta   4980
gggaatttaa ggtaggcctg gttgggttcg gggtacaagc cttgttactg tgaggaacac   5040
cattgtgtgg taagcacaac agaaattcac tgggcctatt ctctgatgga ccaacaggtc   5100
cacccccttcc cccatcccca ctcaagagtg tacctacgtg aggaaatcga ggtacttagt   5160
tatctaggga agatttatgt gcttgttaag attaacttgt taccgctaat ggatgcgagg   5220
ccgcagagct atgacaggac atatgtctca cttaattttt ttaatggaac acgcggaaac   5280
cctcatccca caggaccagc tacacagtta gtcttaaaga ttaaggttca aaagatacaa   5340
gtcccctgct gggaccactg tgccttttag gccttctggg atttctgaga ttaagaaaag   5400
gggctagggg ggttgggtat ttagctcagt ggtagagcgt ttgcctagca agcacaaggc   5460
cctgggttcg gtccccagct ccgggggggga aaaaaaagaa agaaagaaag aaagaaggaa   5520
agaaagaaag gaagaaagga agaagagggg ctagggaaaa gcactctgaa gtgctaagga   5580
agtgcatttt ttgagggaga gttgggggtg ggtgggacgt ggtcctcaca gcacagcttg   5640
gcatccggta gccttactta ggaggcccag tgaaactggg gaatctaact tttttgcaaa   5700
gtgtgtgtga ttttagtgtt gtcattgagt gttgcatgct tctggaggaa tggaaagccc   5760
cgactctgta tgggagacac aggagtaagg gtctgctctg gggccaagtt gaattttgag   5820
agtgttggag gatagactat agacacagtt tagttggtag agtgcttggc cgggatgcat   5880
aagtctgtgg gttccatccc caacactatg taaactaggt gtggtggccc agacctatga   5940
ccctagcact taggaggtga agggacaaga ggatcaaggt tcaaggttat cttcagatac   6000
ataacaaatg gtcctggaca catgtcacaa tagcctgtac ttccagcagt gggacatcca   6060
acatcctctt ctgttctcca agggcacaca cacacacaca cacacacaca cacacacaca   6120
cgcacacaca cacacactta aaagctggtg agtaagttgg gccttgacct ccacttggta   6180
atagctcagt tcaattgcac tgcagtgggc acttcttgaa atgatttaac ttccatagtt   6240
cctttcttca cctgcccagg aaggtcatac atgaagtaaa tggacaaggg catgtataca   6300
gaatgccctg aaaaatagga caaagttcag aggaccatgt aggtaagacc tttcatcttc   6360
aaacgttgca cagctaaatt ggtgaccccc cactggtctc ctggggtcaa aggtatataa   6420
agttaagctt ctgggaacac agaggatatg caaatgccag agagaaaccc tggaaagaaa   6480
gcagggctct tttggagaat tccttttcct tttggatccc tgaggatata tgggtttagg   6540
catcttaaat agtattggat gttgcgggga gccggggggg gcatagatgg aggtacaggg   6600
caagctgggg ctccggagac ccagaggctc cgacctacag gttctgtgac tgcatcatct   6660
ctagatagac tgaggcacac agggactctt gcaggtcggt tccaggttcc aataacagag   6720
gatactctag acgggagaga ctcctctgct tgtccactgg tcgccagcaa agcccagctt   6780
ttctatctac agagtggcgt tacagtaggg gtctccaagg aaagcagggg agagcggccc   6840
agagagccag ttttgaagaa aaccatccag aaagtcacaa atggtttaga acttccccta   6900
tgtggcagca tttggcctgt agaacgaaat ttgcaaacac ttcttaaatt ccagccatag   6960
attgctccaa gctcagggac ttccacctca gcaccctcca ccagcactcc taaaagccag   7020
aatccagtca caagagcctt tggctgggaa tagatagcaa gtacaggtgg ccgttgggga   7080
ctcaggcacc actcatcccc cccccccccc acctgctcct ccccacccac ttgctggagc   7140
```

gaatccgtag tagttgttcc ccaaagaggg tctgggagca ctcggtgaca ccgcctaggt 7200
ctggtttccc taggaaacaa cccacgcacc agggttgggc tgcttcggac acggcccgga 7260
tgaactgttg caacttgggc agcccgcagc gcggcgcagt ggcagaggcg ggggcgtgaa 7320
gccgggaggc gcgtgtaacc aggatcctcg aagctccgga gacccggagg cgaaaggatc 7380
cgcacaggaa cccagggcaa cctgcgcgag tggcggagcc ccgcgctccc gccctagctc 7440
aaggggagcg cagtcgtagc ggggttcaga gccccagccc cgtgccaccg ccacccgcgg 7500
tggggggtgg gctgggggcg gggcagctgg ggttgccttc ccgggcgcga tccccgagcg 7560
cggcacccgg cgccgccgag ccacctcccc tgccgcccgc cagcaagttt ggcggcttcg 7620
agcccagaga gccacggctt tctgaagcac tggtttcttg ttagcgttgg tgcgccctgc 7680
ttggcggggg ttctccggag cgatgccgat ggatgtgatt ttagttttgt ggttctgtgt 7740
atgcaccgcc aggacaggta agcaaggctg ggcgttaagg gggatatggg gggaggtggt 7800
ggtgatgatc atgctgttcc tggttgctgt aacccgggat tactctggct gtgagagacg 7860
cggaaactag ctctgacggg ctagagaaag aaggacagca gcatgcttgg gtctctgatc 7920
gcccagcaca gctcggggta aaagcgctag aaaagatgtt ctggcgagcg tcctcttccc 7980
cagggacgca gctgcgggca ttcagtgtgc agggtgcggc cgggtggtcg cacccttgtg 8040
tggctagcta gtagcttccc ggttctgggg agtcagaacc cgctgcagcg ctgccagcga 8100
tccctacatc cttgaacttg cagggtgcgg tggacgaggg tgtcactgag ccgcgggagt 8160
tccacccgca gagggagcgc gtgtagcaag caggtacggc cagggctggg gggagccaga 8220
cgcctcacag gagagggctg cgaggaaagc ggggacctgc gagctcttct gtggctccca 8280
catggttccc ggaggggaac tctaggattg ttctcctttt atgggctccg cgcctaaaca 8340
actgggcgaa caattattag gagggaattt ggagcagtgg agacaactgg aagattttct 8400
cacccgctaa accgtgtttc taatgctatc atcaaagatt gcagggcggg accaggggcc 8460
aaggaaattg gcctaatggc caagtcccta agagaagctg cctgctggag gtggccttat 8520
gatgaccctg aggagcactc ccctctttct tcttccacag ggttccctg actccaggtc 8580 cctggggttc aagaatgtag cctacttcac tggaggcagg ag 8622

<210> SEQ ID NO 87
<211> LENGTH: 3060
<212> TYPE: DNA
<213> ORGANISM: Rattus norvegicus

<400> SEQUENCE: 87
tggcatctgc tggagaagca acaagtggtt ctgaaatcac ctctgctcgt ttagaataga 60
tttgatagca caggaaactt gtacatgaag tttgtatgaa atctgggagc ggagcacctc 120
accgtttttc ttttttgttg ttgatgtttc tattcttgct atgacatttt acacactata 180
taaaatactg gcagcattct caatttacta taaatggaac ctcagaacgc ttggtggtat 240
gactgctctt gtctctctaa gccccgtggg atcccgggaa acagcacaat gcaggactga 300
gtccttatca aacctgctgc tcgcctgctg tctgaggaga ggccttacca aggcgatgca 360
caaccaccca tcagtcacct gtcatcgact tcaaaattca aatcttataa taagagttta 420
ctaaagtaca gtccatatat caggaacgca ggccttgcaa ggccatggca gacggtagag 480
agtggctaat acacaaagat actcaatgag gctggaagtg taattccaca tctttgagtg 540
aaaactagat ttgtgaagcc tttgctcttt ctaatattga gcttggtatt atctaggaaa 600

-continued

```
caaaagaagt tcaccagtgg gagccggcat ccgccaactg agcacaatta aaagaaaaca    660
cagcacgggc catgcttttt aaacacaaca catactttaa agaagctgac tatttatata    720
gaaataacta ttgttttaaa ttaactagaa gaggaaactt gataccctga gactattgcc    780
tagaaactgt caaactgttt gatatgtaat tgtccaattg tctcacaaaa aactgtacat    840
ttctggtttc tgcttgtgat agatgtacat tctgtatagg aagccagtac ccttaggaag    900
gctagagggg gcctgtgcgg ttatcataag aatacagaca attattagaa actcgttttg    960
taaagcttcc tatttactca aactgtcaag tcctaaaata gtaaggccct gttctaagag   1020
actgaaaatg agaaacagaa acaacacgca gcataagcct aacgcctata cctaattaca   1080
tctctagcca actggaattt tgctgacaat tgggctctat ttccgtgatt acattaggct   1140
attgtcttca gtatcccagc cccaccctcc ccaaagcatc tgaaagtgaa gaaaatatca   1200
taaacacttg tcacaataga aacaccaatt aaggacttta actgaaatcc ttgcttaaag   1260
agcttacatt ttaatttatg atgaacacaa actcctctta aatgcaacac atgtcagttt   1320
ttcccctctc cctacagaga gcttatgagc tgctgtccat ggtggcaccc gctggctgta   1380
tgcagcaaca gcgccaccac agaaacatcc aagttgcatc ctatgtctgc ttcttaaggc   1440
agatgtgctg ggttggttgc attttgcatt gccaacgtct ccgtaattct aagttgcacg   1500
acttcatttg aagccatagc tcccaaaagc ataagaacct cccataccca tgtgtagtgg   1560
gagaggacgc cttgattttc gagatccggg accttcctct gtgcttctct atgaattcct   1620
tggacacttt agccccctta tagaccctca agctaagcac catcctgcaa gccaggaagt   1680
cttcaaaagc tttgctcaat caatttgctg cccgctttct ttaattgaag tttccttaag   1740
actgaacagt atattgaaat ataatttgaa atatgggcag taatgaataa ccaatgtcca   1800
ctgacttcaa aaagaaaaaa aagttttaaa attctacaat tacggtgata tgaggctgtg   1860
cttctgtgaa catccccttg aaacgatttc aaaataattg taacagtatc gtgcccttcc   1920
cctggccact gatgggaagg gaagaatggg tagcgctcca tggtactctg cttcaagtac   1980
agagatgtgc agtagaaata ccgtaaggga attcctctgg gcaggcacca cagcgccgaa   2040
actttgggag gtcagtatct taaccaagat tgagctatct tgtttccttc ccaaatccat   2100
tccacccaaa tgaggcgttt gtgttacaat ttattgttcc ctagacgccc aaatcaccca   2160
tctgcctctg gagtttctag tcggtaatta aggcactatc cattacaacc gccaagtgca   2220
ccaagtgagg aggaggaggg cgcaggaaat gaagggggag aacccacttt aaaagagcca   2280
ggccctgagc gcacagagcc cttcacccca gctgggaccc tccgcctgcc caccccagtg   2340
cagcgcgaag ccaagttagc aagagccgca gggccagctc cccacgacac acagggggct   2400
tctcactggg ccataccttg gaagaggaag gctttcgtcc cattatgcag tcctgggact   2460
tggcgcactc cagctgtgga ctccccaagt tctaactctg ataagacgtc aatctgtagg   2520
gaggggtcca caccaagtcc ccaaactggt gggagtggag aggggtagga aagaaaggaa   2580
gagagaaaga aagggggcca ttaaaacgca agcttccaca gcagcaaaga aagcacgcgt   2640
cttggcgaca atatttggaa gtgctgacaa gaggcaacac gctcctccac agggagagcc   2700
ttacctggac gcgctgtcaa gcttaaaata gcagagcgct gggtcccatc tcctgaccta   2760
ctttaagccc ctctctgtac aaagttcccc cacagccaca gaccctaagg gtgtgacccg   2820
ccttgctgtc gccaggacaa gcacagaaag gactcaaatg caaaccctcc agaggtcccc   2880
aatccagagg gaaaccgggc ggcgacccca tggcggggag catcccggcc cagctcggcg   2940
gccactcacc cgcttcgagc ccgaggatca cgcagaacgt tctcagtaat acccgggatt   3000
```

ccatggcgtg catcgtctca gtccatcgtc tccctcttta aaaaataaag ataaaaacca 3060

<210> SEQ ID NO 88
<211> LENGTH: 72
<212> TYPE: DNA
<213> ORGANISM: Homo sapiens

<400> SEQUENCE: 88
atggagtctc gggtcttact gagaacattc tgtttgatct tcggtctcgg agcagtttgg 60
gggcttggtg tg 72

<210> SEQ ID NO 89
<211> LENGTH: 24
<212> TYPE: PRT
<213> ORGANISM: Homo sapiens

<400> SEQUENCE: 89

Met Glu Ser Arg Val Leu Leu Arg Thr Phe Cys Leu Ile Phe Gly Leu
1 5 10 15

Gly Ala Val Trp Gly Leu Gly Val
20

<210> SEQ ID NO 90
<211> LENGTH: 72
<212> TYPE: DNA
<213> ORGANISM: Rattus norvegicus

<400> SEQUENCE: 90
atggaatccc gggtattact gagaacgttc tgcgtgatcc tcgggctcga agcggtttgg 60
ggacttggtg tg 72

<210> SEQ ID NO 91
<211> LENGTH: 24
<212> TYPE: PRT
<213> ORGANISM: Rattus norvegicus

<400> SEQUENCE: 91

Met Glu Ser Arg Val Leu Leu Arg Thr Phe Cys Val Ile Leu Gly Leu
1 5 10 15

Glu Ala Val Trp Gly Leu Gly Val
20

<210> SEQ ID NO 92
<211> LENGTH: 72
<212> TYPE: DNA
<213> ORGANISM: Mus musculus

<400> SEQUENCE: 92
atggaatccc gggtgttact gagaacgttc tgcgtgatcc tcggccttgg agcggtttgg 60
gggcttggtg tg 72

<210> SEQ ID NO 93
<211> LENGTH: 24
<212> TYPE: PRT
<213> ORGANISM: Mus musculus

<400> SEQUENCE: 93

Met Glu Ser Arg Val Leu Leu Arg Thr Phe Cys Val Ile Leu Gly Leu
1 5 10 15

Gly Ala Val Trp Gly Leu Gly Val

-continued

```
            20


<210> SEQ ID NO 94
<211> LENGTH: 72
<212> TYPE: DNA
<213> ORGANISM: Canis familiaris

<400> SEQUENCE: 94

atggagcctc gggtcttgct gagaaccttc tgtttgatct tcggtctcgg agcagtctgg     60

gggctcggtg tg                                                          72


<210> SEQ ID NO 95
<211> LENGTH: 24
<212> TYPE: PRT
<213> ORGANISM: Canis familiaris

<400> SEQUENCE: 95

Met Glu Pro Arg Val Leu Leu Arg Thr Phe Cys Leu Ile Phe Gly Leu
  1               5                  10                  15

Gly Ala Val Trp Gly Leu Gly Val
            20
```

PHARMACEUTICAL COMPOSITIONS FOR TREATING OR PREVENTING BONE CONDITIONS

RELATED APPLICATIONS

This application is a divisional application of U.S. application Ser. No. 11/884,525, which was filed on Aug. 15, 2007 and issued as U.S. Pat. No. 7,833,968, which in turn is a national phase application of PCT/US2006/005473 filed on Feb. 16, 2006, which in turn claims benefit of U.S. provisional application No. 60/653,722 filed on Feb. 16, 2005, all are entitled "PHARMACEUTICAL COMPOSITIONS FOR TREATING OR PREVENTING BONE CONDITIONS" and each of which is hereby incorporated by reference herein in its entirety.

BACKGROUND OF THE INVENTION

The present invention is generally related to pharmaceutical compositions for treating or preventing bone condition. These pharmaceutical compositions may be used to induce bone and/or cartilage formation in wound healing and tissue repair.

The costs of treatment for orthopedic and craniofacial bone conditions represent a significant biomedical burden. According to the 2002 US Health Cost & Utilization Project, hospital costs for cranial surgery (craniotomies and craniectomies) and facial trauma reconstruction alone were estimated to be approximately $549 million and $400 million, respectively (Steiner, C., A. Elixhauser, and J. Schnaier, Eff Clin Pract, 2002. 5(3): p. 143-51). The hospital costs for orthopedic surgeries (both trauma and nontrauma) are likely even higher as the figure for orthopedic industry sales alone was estimated to be $13 billion in 2002 (Medical Technology Fundamentals, Merrill Lynch, 2003. p. 11).

Overall, the major problem encountered in the treatment of orthopedic and craniofacial bone conditions concerns the modulation of bone and/or cartilage formation. Preferably, bone formation can be increased under conditions in which it would be desirable to have more or accelerated bone formation as part of the treatment of certain conditions (e.g., orthopedic or craniofacial fracture repair, spinal fusion surgery, joint fusion surgery, injured osteoporotic bone) or as part of the prevention of certain conditions (e.g., fracture prevention in osteoporotic bone). For long bone fracture, it would be desirable to have accelerated endochondral bone formation by accelerating the cartilage to hypertrophy and replaced by bone. Even more preferably, bone formation can also be decreased under conditions in which it would be desirable to have decreased or inhibited bone formation as part of the treatment or prevention of certain conditions (e.g., craniosynostosis, a condition of premature calvarial overgrowth across sutures leading to premature suture fusion; heterotopic ossification, a condition of abnormal bone formation in ectopic locations). Similarly, it would be preferred to increase cartilage formation under conditions in which it would be desirable to have more or accelerated cartilage formation (e.g., joint resurfacing, temporomandibular joint reconstruction, articular disc repair, intervertebral disc repair and regeneration).

Many compositions have been described for the treatment of bone conditions (Table 1). Most, if not all, describe compositions that promote bone formation through osteoconductive and/or osteoinductive properties. It is well established in the art that compositions with osteoinductive properties are generally more efficacious at forming bone than those with osteoconductive properties; however, both are necessary for optimal bone formation (Table 1). The current "gold standard" composition for treatment of many bone conditions is autologous bone graft, which has both osteoinductive and osteoconductive properties. However, autograft harvest can be associated with significant donor site morbidity including pain, gait disturbance, thigh paresthesia for iliac crest donor sites (Laurie, S. W., et al. Plast Reconstr Surg, 1984. 73(6): p. 933-8). Thus, there is a critical need for better autograft alternatives. Of compounds with osteoinductive ability, the bone morphogenetic proteins (BMPs) have been extensively described. When coupled with an osteoconductive carrier, BMPs offer the greatest promise of equaling or even surpassing autograft for treatment of many bone conditions (Valentin-Opran, A., et al. Clin Orthop, 2002(395): p. 110-20).

However, the known functional heterogeneity of the BMPs (Ducy, P. and G. Karsenty, Kidney Int, 2000. 57(6): p. 2207-14; Wang, S., et al., Kidney Int, 2003. 63(6): p. 2037-49) and the high dose of BMPs required for osteoinduction may limit their use due to cost considerations and to unpredictable side effects such as maxillary sinus cyst formation (van den Bergh, J. P., et al., J Clin Periodontol, 2000. 27(9): p. 627-36). Consequently, there is an ongoing clinical and commercial need for alternative or complementary osteoinductive molecules to the BMPs to promote bone and/or cartilage formation. In addition, there is an ongoing clinical and commercial need for inhibiting bone and/or cartilage formation under specific conditions that is not addressed by the osteoinductive BMPs.

The embodiments described below address the above-identified problems and needs.

SUMMARY OF THE INVENTION

In one aspect of the present invention, provided herein is a pharmaceutical composition containing one or more agents such as one or more NELL peptides or NELL RNA. In one embodiment, the pharmaceutical composition contains an effective amount of one or more NELL peptides for treating bone conditions through promoting bone generation after injury, e.g., long bone fracture healing, spinal fusion, and craniofacial bone repair. In another embodiment, the pharmaceutical composition contains an effective amount of one or more NELL peptides for treating or preventing bone conditions through promoting bone generation without necessarily evidence of overt bone injury (e.g., osteoporosis, hip necrosis, and alveolar ridge bone resorption).

In some embodiments, the composition described herein is effective and can be used to treat, prevent, ameliorate, mitigate or reduce the symptoms of diseases/conditions that involve multiple symptoms where bone metabolism is a secondary effect. Examples of such diseases or conditions include, but are not limited to, chronic kidney diseases which can cause many systemic effects including renal osteodystrophy and vascular calcification. Nell can increase bone formation without stimulating undesirable bone formation, and thus it can stimulate the formation of bone only in bone compartments without stimulating proliferation of non-bone cells in the body (e.g. pre-cancerous cells), and as a result the targeted bone formation alleviates bone loss due to kidney damage. The NELL-induced mineralization also consumes the calcium and phosphate ions that otherwise form pathological calcification in normally non-calcifying tissues such as blood vessels. Other forms of pathological calcifications have multi-factorial origin (bacterial, paracrine, autocrine, etc.). The ability of Nell to favor the balance between bone deposition and bone resorption makes the composition described herein an effective composition to maintain the essential ions in the bone compartment and decrease their bioavailability in non-bone tissues, thereby reducing the risk for ectopic soft tissue calcification, gall stone, kidney stones, pineal gland calcification, cataracts, salivary stones, cardiac valves, and/or prostate stones.

In another aspect of the present invention, the present invention provides a pharmaceutical composition that contains an effective amount of an inhibitor of NELL peptides for inhibiting bone generation (e.g., craniosynostosis or heterotopic ossification, osteopetrosis). In yet another aspect of the present invention, the invention provides a pharmaceutical composition that contains a sufficiently high enough dose of NELL peptides for inhibiting bone generation. In still a further aspect of the present invention, the present invention provides for a pharmaceutical composition that contains an effective amount of a modulator of the receptor of NELL1 or NELL2 peptides for promoting bone generation, e.g., craniofacial or long bone generation. The modulator can be an agonist of receptor of NELL1 or NELL2 peptides. In another embodiment, the pharmaceutical composition contains an effective amount of a modulator of the receptor of NELL1 or NELL2 peptides for promoting bone generation for treating or preventing a bone condition that decreases bone mass such as osteoporosis and alveolar ridge bone resorption. The modulator can be an agonist of receptor of NELL1 or NELL2 peptides.

In yet a further aspect of the present invention, the present invention provides a pharmaceutical composition that contains an effective amount of a modulator of the receptor of NELL1 or NELL2 peptides for inhibiting bone generation, e.g., craniofacial or long bone generation. The modulator can be an antagonist of receptor of NELL1 or NELL2 peptides. In one embodiment, the pharmaceutical composition contains an effective amount of a modulator of the receptor of NELL1 or NELL2 peptides for inhibiting bone generation for treating or preventing a bone condition that increases bone mass such as osteopetrosis. The modulator can be an antagonist of receptor of NELL1 or NELL2 peptides.

In a further aspect of the present invention, the present invention provides a pharmaceutical composition for bone generation that includes one or more enhancers for a NELL peptide.

In a further aspect of the present invention, the present invention provides a pharmaceutical composition that contains an effective amount of at least one agent for either directly or indirectly promoting the generation of cartilage for treating or preventing a cartilage related bone condition (e.g., joint resurfacing, temporomandibular joint reconstruction, arthritis repair, or intervertebral disc repair). One of the agents for direct promotion of cartilage generation can be NELL peptides applied to chondrogenic cells such as, but not limited to, chondroblasts, chondrocytes, or chondroprogenitor cells, stem cells, bone marrow cells, a bone marrow stromal cells, a fibroblast, or adipose derived cells. The agent for indirect promotion of cartilage generation (e.g., through inducing chondroblast/chondrocyte differentiation) can be, e.g., one of NELL peptide, or agonists of NELL peptide receptors.

Under certain specific condition when inhibition of endochondral bone formation is desired to prevent further cartilage replacement by bone, the pharmaceutical composition can include, e.g., one or more inhibitors or antagonists of NELL peptide receptors, high dose NELL peptides, or combinations thereof. Such a composition is effective for inhibition of osteoblastic differentiation by inhibiting potential or committed osteogenic cells such as, but not limited to, osteoblasts, osteoprogenitor cells, stem cells, bone marrow cells, fibroblastic cells, dural cells, periosteal cells, pericytes, and/or muscle cells.

In a further aspect of the present invention, bone formation can be induced through small molecules regulating NELL promoter.

The above described pharmaceutical composition can optionally include a pharmaceutically acceptable carrier for a suitable mode of delivery for systemic or local delivery. For example, the pharmaceutically acceptable carrier can be a carrier for oral delivery, pulmonary delivery, parenteral delivery or implantation.

In a further aspect of the present invention, the present invention provides a method of treating or preventing bone conditions. The method generally includes administering to a mammal a pharmaceutical composition described herein.

The pharmaceutical composition can be formulated into various formulations for a suitable mode of delivery.

BRIEF DESCRIPTION OF THE DRAWINGS

FIG. 2A also shows the typical borders of mineralization (dotted light blue line) as well as the location of the anterior (red asterisk) and posterior (blue asterisk) fontanelles. A faint outline of the right coronal suture (green arrows) can be seen. The coronal sutures are usually less visible because they are overlap rather than butt sutures. On the middle picture, note also the normal size of the clavicles (black arrows). The micro-CT reveals the typical craniofacial bone morphology. The coronal sutures (green arrows) and the anterior fontanelle (red asterisk) are highlighted.

FIG. 3A shows Von Kossa's staining of adenoviral NELL1 (AdNELL1) transduced bone marrow stromal cell (BMSCs) derived from long bones. Cells were cultured to 80% confluency and then infected with 50 plaque forming units (pfu)/cell AdNELL1 (right). Controls were infected with 50 pfu/cell Adβ-Gal (left). At day 11, von Kossa's stained bone nodules were counted and bone nodule numbers are presented at the mean±SEM. Each experiment was performed in triplicate. Representative samples of stained bone nodules are indicated (green arrows). AdNELL1 transduced BMSCs had significantly more mineralization and bone formation. (A) After 2 weeks of infection with Nell-1 or LacZ, a significant increase was also seen in the formation of calcium nodules in the AdNell-1 BMSCs compared to AdLacZ (n=3; p=0.0018). FIGS. 3B, and 3C show transduced BMSCs injected into muscle of nude mice. (B) AdNell-1 transduced BMSCs demonstrate more bone formation radiographically. (C) Nell-1 transduced BMSCs show histology of relatively more mature bone with lamellar pattern than the control. Collectively, FIGS. 3A-3C demonstrate increased bone mineralization and bone formation in as a result of NELL1 overexpression in cells derived from non-calvarial sources. In this case, NELL1 induced stem cells to form bone.

FIG. 5A represents a 4 week calvarial section treated with NELL 1-loaded membrane (outline of original defect in green), and BMP2-loaded PLGA membrane (outline of original defect in red) (endocranial view). FIG. 5B represents the same specimen as FIG. 5A (exocranial view). FIG. 5C represents a 4 week calvarial section treated with NELL1-loaded PLGA membrane (outline of original defect in green) (endocranial view). Collectively, FIGS. 5A-C demonstrates similarly increased bone mineralization and bone formation from NELL1 and BMP2 treatment.

FIG. 7A shows that NELL1 is expressed throughout the tibia including both articular cartilage region (Upper panel) and also the endochondral long bone formation region (lower panel). Upper panel demonstrate that NELL1 can modulate and increase cartilage differentiation in the articular cartilage region. Accordingly, these data show that increased NELL peptide activity directly (e.g., through addition of NELL peptides or increased NELL peptide expression) or indirectly (e.g., through addition of NELL peptide enhancers and/or NELL peptide receptor agonists and/or activators) promotes cartilage formation. In the lower panel, in the long bone shaft region where endochondral bone formation originated, increased NELL1 causes cartilage formation and then hypertrophy and increased endochondral bone formation, while absence of NELL1 allows maintenance of less differentiated articular chondroblast/chondrocyte phenotype without endochondral bone formation in the Cbfa1 knock out model. Accordingly, these data show that increased NELL peptide activity directly (e.g., through addition of NELL peptides or increased NELL peptide expression) or indirectly (e.g., through addition of NELL peptide enhancers and/or NELL peptide receptor agonists and/or activators) promotes cartilage formation, cartilage hypertrophy and endochondral ossification. It is useful in endochondral bone formation such as bone fracture. The absence of exogenously NELL1 associates with controlled articular chondroblast/chondrocyte phenotype and suppression of hypertrophy which is important to prevent articular cartilage replaced by bone. Accordingly, the inhibition of NELL peptide activity directly (through decreased NELL peptide expression or use of NELL peptide inhibitors) or indirectly (through NELL peptide receptor antagonists and/or inhibitors) can prevent cartilage hypertrophy and endochondral ossification and promote maintenance of articular cartilage phenotype. Overall, these data not intended to be limiting, but rather to show that NELL_has broad effects on osteochondroprogenitor cell types and that the exact phenotype induced by NELL depends on a complex interplay between the amount and timing of NELL application, the exact cell type, cell differentiation state, and the microenvironment.

FIG. 7B shows that, in a palatal distraction model, NELL1 protein induce cartilage to from (blue staining) FIG. 7C shows that NELL1 increases chondroblast proliferation indicated by increase Sox 9 staining Sox 9 is the marker for chondrogenic cell proliferation. FIG. 7D shows NELL1 induces the cartilage to further differentiate as indicated by increased type X collagen staining Again, FIG. 7D demonstrates that NELL1 can accelerate cartilage differentiation/formation and also cartilage based endochondral bone formation. Collectively, FIGS. 7A-D demonstrate that NELL1 can modulate cartilage differentiation and hypertrophy. Increased NELL1 causes cartilage formation and hypertrophy and increased endochondral bone formation under different microenvironment, while absent NELL1 allows maintenance of less articular chondroblast/chondrocyte phenotype.

FIG. 11A shows putative OSE2 binding sites, A, B and C are shown along with sequence and position relative to the transcription start site. Cryptic OSE2 site is depicted by striped box. FIG. 11B is a comparative schematic of the human, mouse and rat Nell1 promoters (not drawn to scale). Two of the OSE2 sites in the mouse and rat promoter (sites m1 and 2, and sites r1 and 3, respectively) are located in a region that is 81% homologous. Cryptic sites are indicated by striped boxes. This data shows the sequence of the promoter of Nell can be used for drug screening to induce Nell expression.

DETAILED DESCRIPTION

Figure 1:
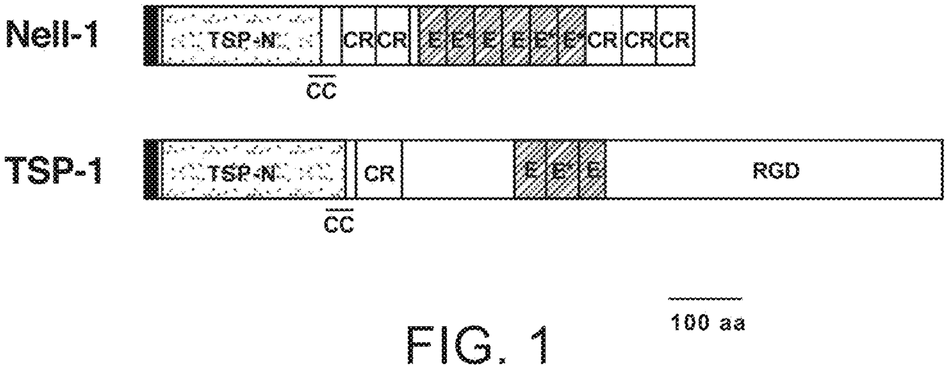
FIG. 1 shows schematic structures of rat NELL1 protein and mouse thrombospondin (TSP)-1. Signal peptide region (solid black box), TSP-N modules (TSP-N, shaded box), cysteine-rich (CR) domains (CR, solid white boxes), epidermal growth factor (EGF)-like domains (E, hatched boxes), coiled-coil regions (CC, bars), Ca2+-binding type EGF-like domains (*), and RGD peptide domains (RGD, solid white box) are indicated.

In one aspect of the present invention, provided herein is a pharmaceutical composition containing one or more agents such as one or more NELL peptides to treat or prevent bone conditions. In one embodiment, the pharmaceutical composition contains an effective amount of one or more NELL peptides for modulating (e.g., promoting bone generation, e.g., craniofacial bone generation, dental implant integration, periodontal bone generation, dental or orthopedic implant integration, long bone fracture healing, spinal fusion or combinations thereof. In another embodiment, the pharmaceutical composition contains an effective amount of one or more NELL peptides for treating or preventing a bone condition such as osteoporosis.

In another aspect of the present invention, the present invention provides a pharmaceutical composition that contains an effective amount of an inhibitor of NELL1 or NELL2 peptides for treating or preventing bony overgrowth across cranial sutures.

In still a further aspect of the present invention, the present invention provides for a pharmaceutical composition that contains an effective amount of a modulator of the receptor of NELL1 or NELL2 peptides for promoting bone generation, e.g., craniofacial bone generation. The modulator can be an agonist or antagonist of receptor of NELL1 or NELL2 peptides. The modulator can activate or inhibit the receptors by itself. In another embodiment, the pharmaceutical composition contains an effective amount of a modulator of the receptor of NELL1 or NELL2 peptides for treating or preventing a bone condition such as osteoporosis.

In a further aspect of the present invention, the present invention provides a pharmaceutical composition that contains an effective amount of at least agent for promoting the generation of cartilage for treating or preventing a cartilage related bone condition. The agent can be one of NELL peptide inhibitors, antagonists of NELL peptide receptors, and combinations thereof.

The above described pharmaceutical composition can optionally include a pharmaceutically acceptable carrier for a suitable mode of delivery for systemic or local delivery. For example, the pharmaceutically acceptable carrier can be a carrier for oral delivery, parenteral delivery or implantation.

In a further aspect of the present invention, the present invention provides a method of treating or preventing a bone condition. The method generally includes administering to a mammal a pharmaceutical composition described herein.

In a further aspect of the present invention, the composition described herein can be used to induce bone formation in conjuncture with a bone matrix. The bone matrix can be a demineralized bone matrix or mineralized bone matrix.

In a further aspect of the present invention, a pharmaceutical composition provided herein can be used to induce a stem cell to differentiate into osteoblast by contact the stem cell with the composition. The stem cell can be an embryonic stem cell or an adult stem cell. Further, the pharmaceutical composition can be used to induce bone marrow stromal cell to form bone by contacting the bone marrow stromal cell with the composition described herein.

In a further aspect of the present invention, the composition described herein is effective and can be used to treat, prevent, ameliorate, mitigate, or reduce the symptoms of conditions related to, for example, bone loss due to microgravity, disuse atrophy, prolonged bed-rest, etc.

In some embodiments, the composition described herein is effective and can be used to treat, prevent, ameliorate, mitigate or reduce the symptoms of diseases/conditions that involve multiple symptoms where bone metabolism is a secondary effect. Examples of such diseases or conditions include, but are not limited to, chronic kidney diseases which can cause many systemic effects including renal osteodystrophy and vascular calcification. Nell can increase bone formation without stimulating undesirable bone formation, and thus it can stimulate the formation of bone only in bone compartments without stimulating proliferation of non-bone cells in the body (e.g. pre-cancerous cells), and as a result the targeted bone formation alleviates bone loss due to kidney damage. The NELL-induced mineralization also consumes the calcium and phosphate ions that otherwise form pathological calcification in normally non-calcifying tissues such as blood vessels. Other forms of pathological calcifications have multi-factorial origin (bacterial, paracrine, autocrine, etc.). The ability of Nell to favor the balance between bone deposition and bone resorption makes the composition described herein an effective composition to maintain the essential ions in the bone compartment and decrease their bioavailability in non-bone tissues, thereby reducing the risk for ectopic soft tissue calcification, gall stone, kidney stones, pineal gland calcification, cataracts, salivary stones, cardiac valves, and/or prostate stones.

In some embodiments, the present inventions provide a pharmaceutical composition for promoting bone formation in a mammalian cell. Examples of such a mammalian cell includes, but is not related to, a stem cell, a bone marrow stromal cell, a fibroblast, or an adipose derived cell.

As used herein, the term "NELL (Nel-like molecule-1; Nel (a protein strongly expressed in neural tissue encoding epidermal growth factor like domain)) peptides" can be NELL1 or NELL2 polypeptide, or a fragment thereof; a NELL1 or NELL2 related polypeptide, or a fragment thereof; any polypeptide with significant homology to "NELL peptides" or a fragment thereof. Significant homology can be construed to mean>50% homology to "NELL peptides", e.g., >60% homology to "NELL peptides", >70% homology to "NELL peptides," or >80% homology to "NELL peptides." The NELL peptides can be natural and/or recombinant NELL peptides with a non-mutated wild-type sequence or recombinant NELL peptides with a mutated wild-type sequence that still contains significant homology to NELL peptides. In addition, NELL peptides can be derived from, but not limited to, an organism such as human cells, bacteria, yeast, or insect or plant cells. In some embodiments, the term "NELL peptide" includes structural, functional or conformational equivalents of NELL peptide. As used herein, a structural equivalent of a NELL peptide refers to a protein or peptide including a structure equivalent or substantially similar to that of a NELL peptide or of a functional domain of a NELL peptide. A functional equivalent of a NELL peptide refers to a protein or peptide having a function equivalent or substantially similar to that of a NELL peptide or of a functional domain of a NELL peptide. A conformational equivalent of a NELL peptide refers to a protein or peptide having a conformation equivalent or substantially similar to that of a NELL peptide or of a functional domain of a NELL peptide.

In some embodiments, the NELL peptide described herein can be a derivative of the NELL peptide. The term "derivative" as used herein, refers to any chemical or biological compounds or materials derived from a NELL peptide, structural equivalents thereof, or conformational equivalents thereof. For example, such a derivative can include any pro-drug form, PEGylated form, or any other form of a NELL peptide that renders the NELL peptide more stable or to have a better osteo philicity or lipophilicity. In some embodiments, the derivative can be a NELL peptide attached to poly(ethylene glycol), a poly(amino acid), a hydrocarbyl short chain having C1-C20 carbons, or a biocompatible polymer. In some embodiments, the term "derivative" can include a NELL peptide mimetics. Synthesis of mimetics of a peptide is well document in the art. The following describes an example of the basic procedure for the synthesis of a peptide, including a peptide mimetics:

Before the peptide synthesis starts, the amine terminus of the amino acid (starting material) can protected with FMOC (9-fluoromethyl carbamate) or other protective groups, and a solid support such as a Merrifield resin (free amines) is used as an initiator. Then, step (1) through step (3) reactions are performed and repeated until the desired peptide is obtained: (1) a free-amine is reacted with carboxyl terminus using carbodiimide chemistry, (2) the amino acid sequence is purified, and (3) the protecting group, e.g., the FMOC protecting group, is removed under mildly acidic conditions to yield a free amine. The peptide can then be cleaved from the resin to yield a free standing peptide or peptide mimetics.

In some embodiments, the peptide derivative described herein includes a physically or chemically modified NELL peptide. Physically modified peptide can be modification by, for example, modification by ionic force such as forming an ionic pair with a counterion, modification by hydrogen bonding, modification by modulation of pH, modulation by solvent selection, or modification by using different protein folding/unfolding procedures, which can involve selection of folding/unfolding temperature, pH, solvent, and duration at different stage of folding/unfolding.

In some embodiments, the peptide derivative can include a chemically modified NELL peptide. For example, a short hydrocarbon group(s) (e.g. methyl or ethyl) can be selectively attached to one or multiple sites on the NELL peptide molecule to modify the chemical and/or physical properties of the peptide. In some embodiments, a mono-, oligo- or poly(ethylene glycol) (PEG) group(s) can be selectively attached to one or multiple sites on the NELL peptide molecule to modify the chemical and/or physical properties of the peptide by commonly known protein PEGylation procedures (see, e.g., Mok, H., et al., Mol. Ther., 11(1):66-79 (2005)).

The term "inhibitor of NELL peptides" refers to a chemical or biological compound capable of inhibiting the activity of NELL peptides. The term also includes a chemical or biological compound capable of suppressing the expression of NELL peptides. Inhibitors of NELL peptides can interact directly or indirectly with NELL peptide transcripts or translational products. As examples, methods of interactions can include but are not limited to decreased transcription or translation of NELL peptides, decreased stability of NELL peptide transcripts or protein products, decreased activity of NELL peptide transcripts or protein products, and increased degradation of NELL peptide transcript or protein products. The term "enhancer of NELL peptides" refers to a chemical or biological compound capable of enhancing the activity of NELL peptides. The term also includes a chemical or biological compound capable of enhancing the expression of NELL peptides. As examples, methods of interactions can include but are not limited to increased transcription or translation of NELL peptides, increased stability of NELL peptide transcripts or protein products, increased activity of NELL peptide transcripts or protein products, and decreased degradation of NELL peptide transcript or protein products.

The term "modulator of NELL peptide receptors" refers to a chemical or biological compound capable of facilitating or inhibiting the binding of NELL peptide receptors to or by NELL peptides or to a chemical or biological compound capable of modulating NELL peptide receptor activity irrespective of the presence or the absence of NELL peptide. The modulator that facilitates the binding and/or activation of NELL peptide receptors to or by NELL peptides is referred to as an "agonist" of the receptor, and the modulator that inhibits the binding and/or activation of NELL peptide receptors to or by NELL peptides is referred to as an "antagonist" of the receptor. The modulator that facilitates the activation of NELL peptide receptors irrespective of NELL peptides is referred to as an "activator" of the receptor, and the modulator that inhibits activation of NELL peptide receptors irrespective of NELL peptides is referred to as an "inhibitor" of the receptor.

The term "NELL peptide", "inhibitor of NELL peptide" or "modulator of NELL peptide receptor(s)" is also referred to as an "agent" throughout the specification.

Figures 2A, 2B, 2C:
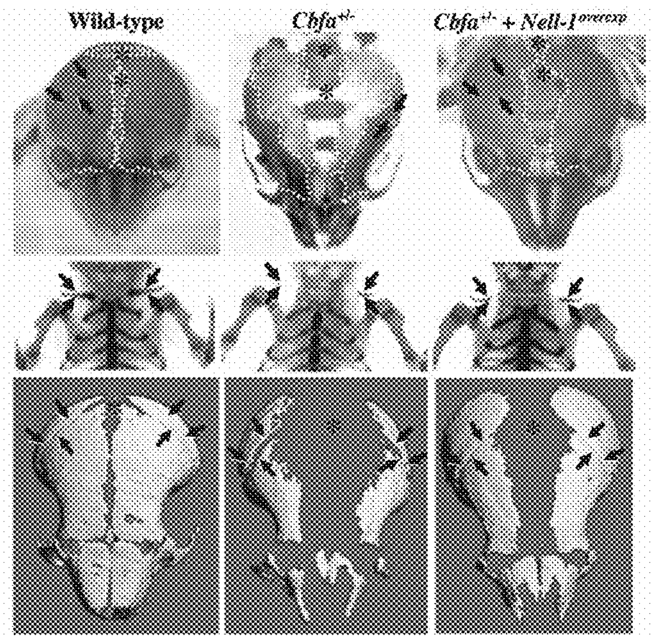
FIG. 2A shows the skeletal pattern of a wild-type mouse demonstrating normal skeletal pattern on skeletal staining (top, middle) and micro-computed tomography (CT) (bottom).
FIG. 2B shows the skeletal pattern of a heterozygous core-binding factor 1 knockout animal ($Cbfa1^{+/-}$). Cbfa1 deficient animals have bone forming defects. These mice demonstrate widely patent midline sutures and fontanelles. Defective mineralization and bone formation is present in the poorly stained tissue (between yellow and light blue dotted lines) lateral to the midline calvarial defect. Lucency can also be seen in the area of the coronal suture (green arrows, top and bottom pictures). On the middle picture, note the significant degree of clavicular hypoplasia (black arrows).
FIG. 2C shows the skeletal pattern of progeny from $Cbfa^{+/-}$ animals mated with NELL1 overexpressing animals ($NELL1^{overexp}$). The $Cbfa^{+/-}$+$NELL1^{overexp}$ animal demonstrated significantly increased calvarial bone formation relative to the $Cbfa1^{+/-}$ haploid deficient animal on skeletal staining and micro-CT. On the middle picture, there is a lesser degree of clavicular hypoplasia (black arrows). The figure also shows the restoration of bony overlap at the coronal sutures (green arrows, top and bottom pictures).
Figure 2D:
FIG. 2D shows calvarial bone overgrowth and ectopic bone formation in ex vivo calvarial bone organ culture when NELL1 is over-expressed or when the NELL1 protein was added.
Figure 2E:
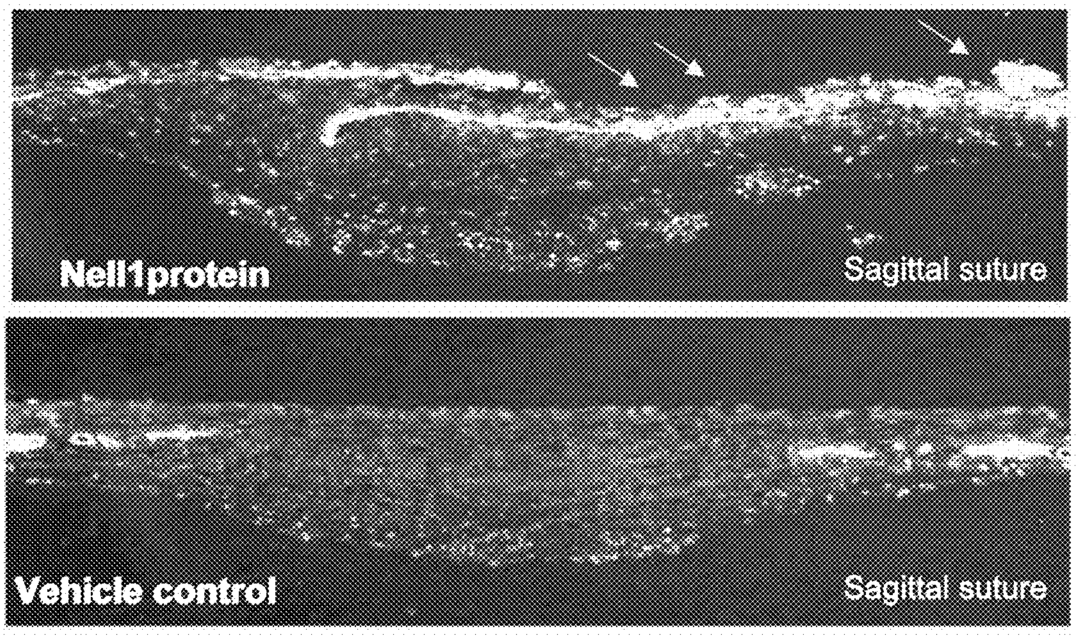
FIG. 2E shows normal mouse calvarial explant with Nell1 protein added. Green fluorescent represents new bone growth. Nell1 protein induce bone over-growth (red arrows), and orthotopic bone formation (yellow arrow). Collectively, FIG. 2 demonstrates increased bone growth in as a result of NELL1 overexpression in both craniofacial areas (e.g., calvaria) and axial skeletal areas (e.g., clavical).
Figure 6:
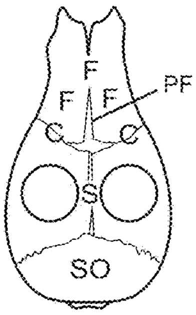
FIG. 6 shows show histology sections of treated calvaria at 4 weeks. Sections were stained using Masson's trichome.
Figure 7A:
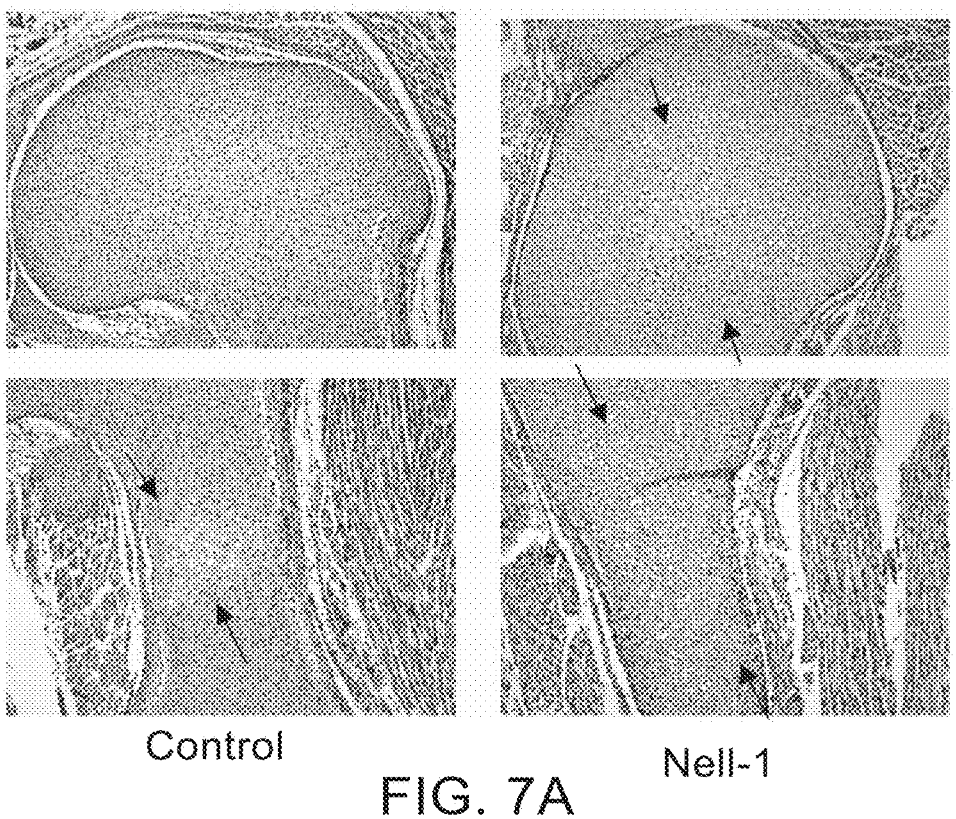
FIGS. 7A-D show NELL1 induce cartilage formation and endochondral bone formation under different microenviromment conditions.
Figure 7B:
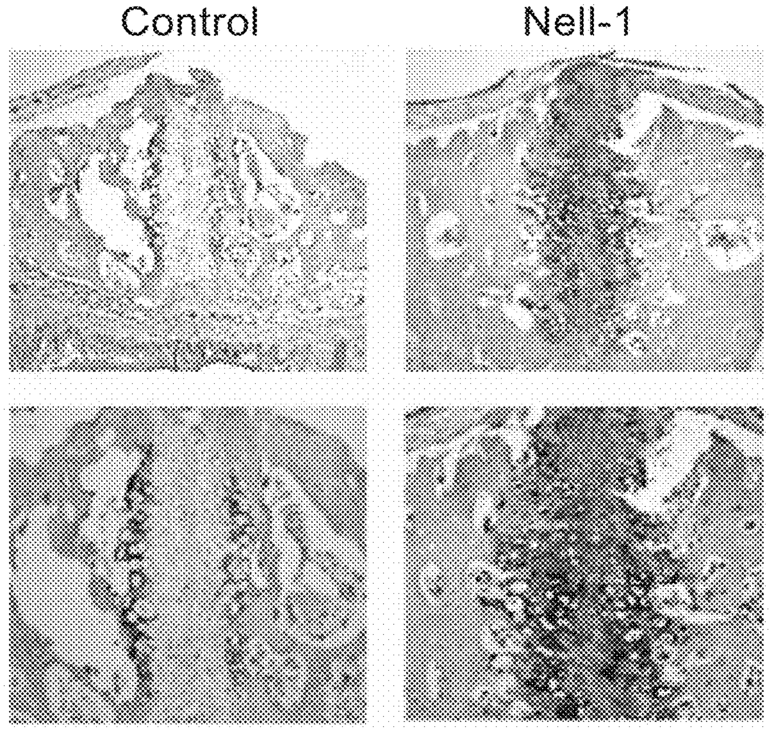
Figure 7C:
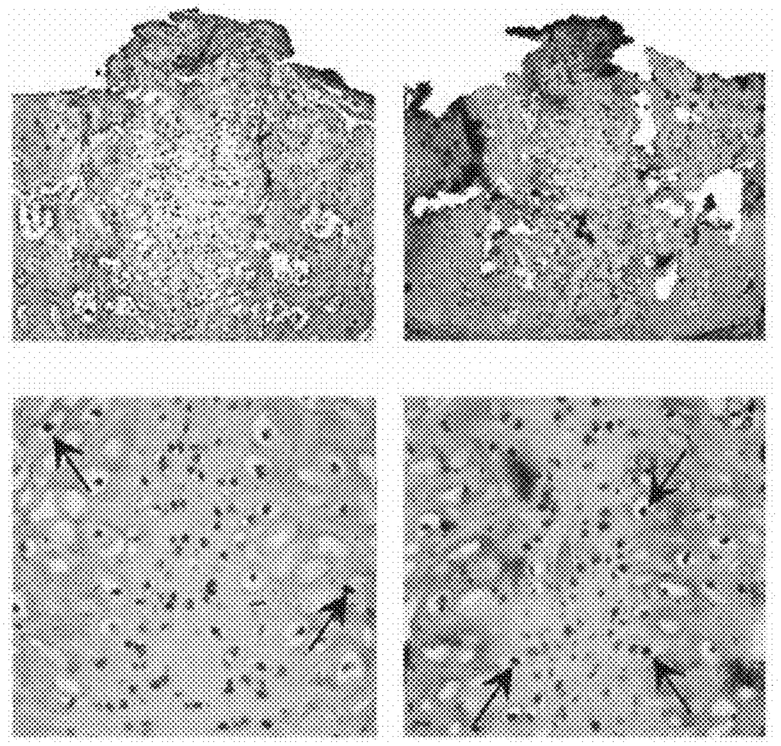
Figure 7D:
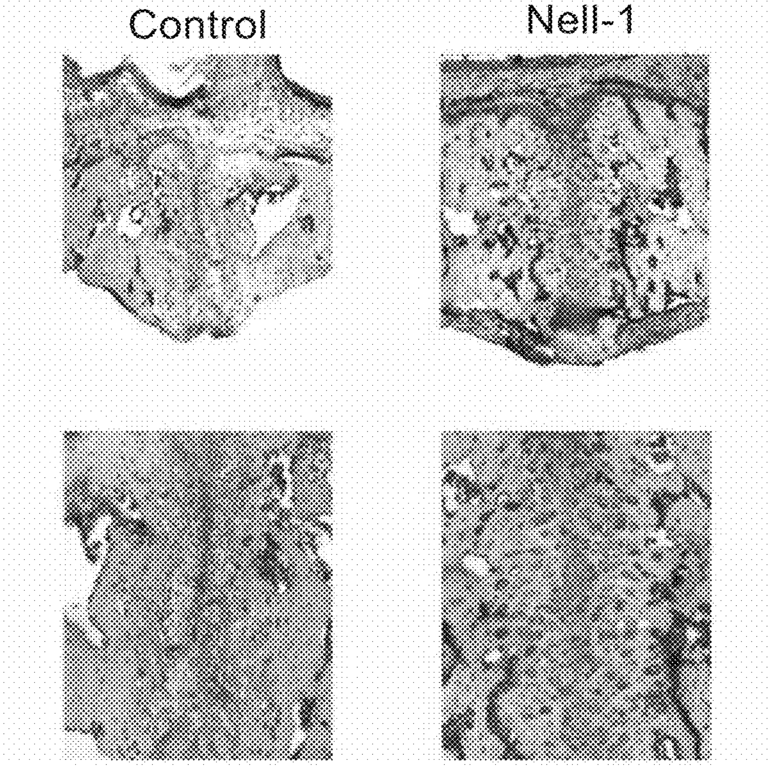
Figures 9A, 9B, 9C:
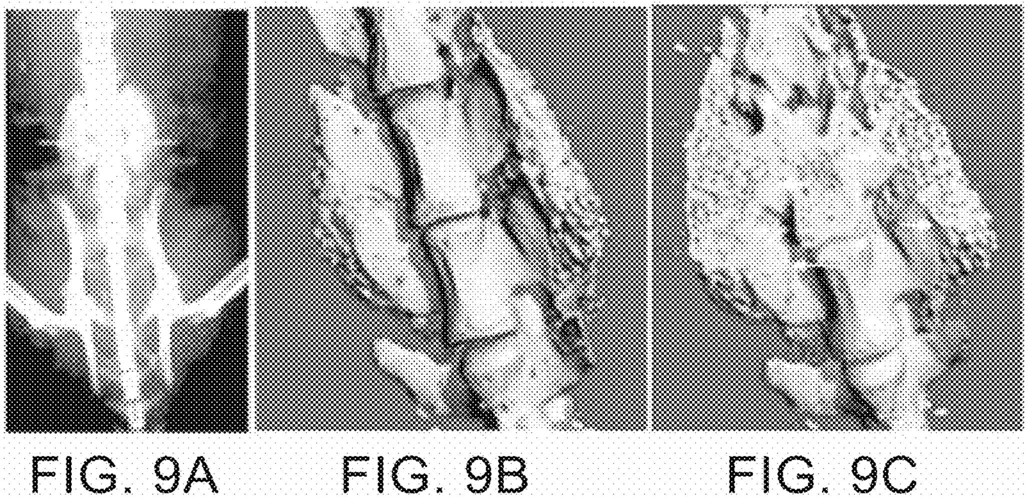
FIG. 9 shows spinal fusion of Nell1 with demineralized bone matrix as carrier. Radiographic and MicroCT three dimensional reconstruction images on 6-week samples of Nell1 treated spine with fusion (A, B and C) and control samples with nonunion (D, E and F). (A) The red arrows identify the radio-opaque tissue masses on both side of spine at L4 and L5 segments. The medial edge (green arrows) of each mass displayed the highest density similar to cortical bone; (B) This microCT 3D image displayed a well defined tissue mass (red arrows) with density similar to bone was packed on the dorsal surface of two transverse processes and the spaces between them (green arrows); (C) The bridging bones (green arrows) clearly connected with both transverse processes (yellow arrows) as shown in this coronal cutting plane image of 3D microCT; (D) Smaller tissue mass (red arrows) with lower radio-opaque seen in this radiograph; (E) Tissue mass (red arrows) over the L4 and L5 region without close contact with transverse processes; (F) In coronal cutting plane of 3D microCT, clefts (pink arrows) were identified. This data demonstrate that Nell1 can induce spinal fusion through one bridge formation.
Figures 9D, 9E, 9F:
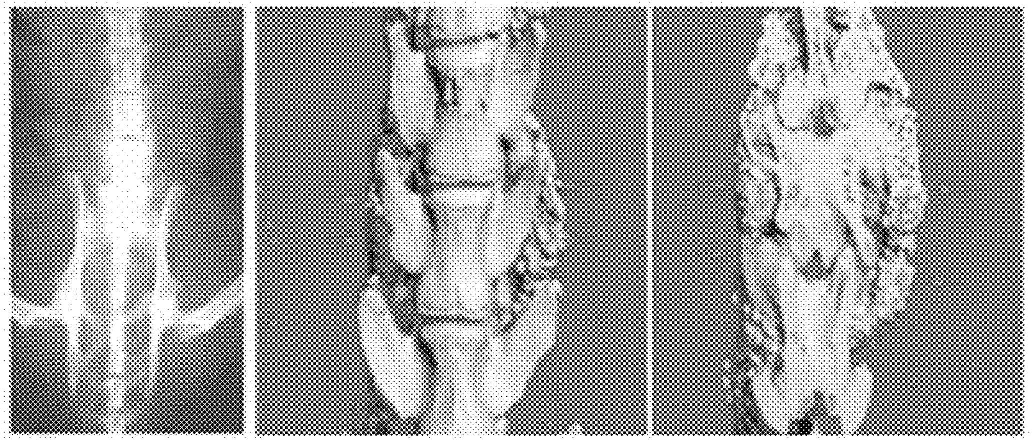
Figures 10, 10A, 10B, 10C, 10D, 10E, 10F, 10G, 10H, 10I:
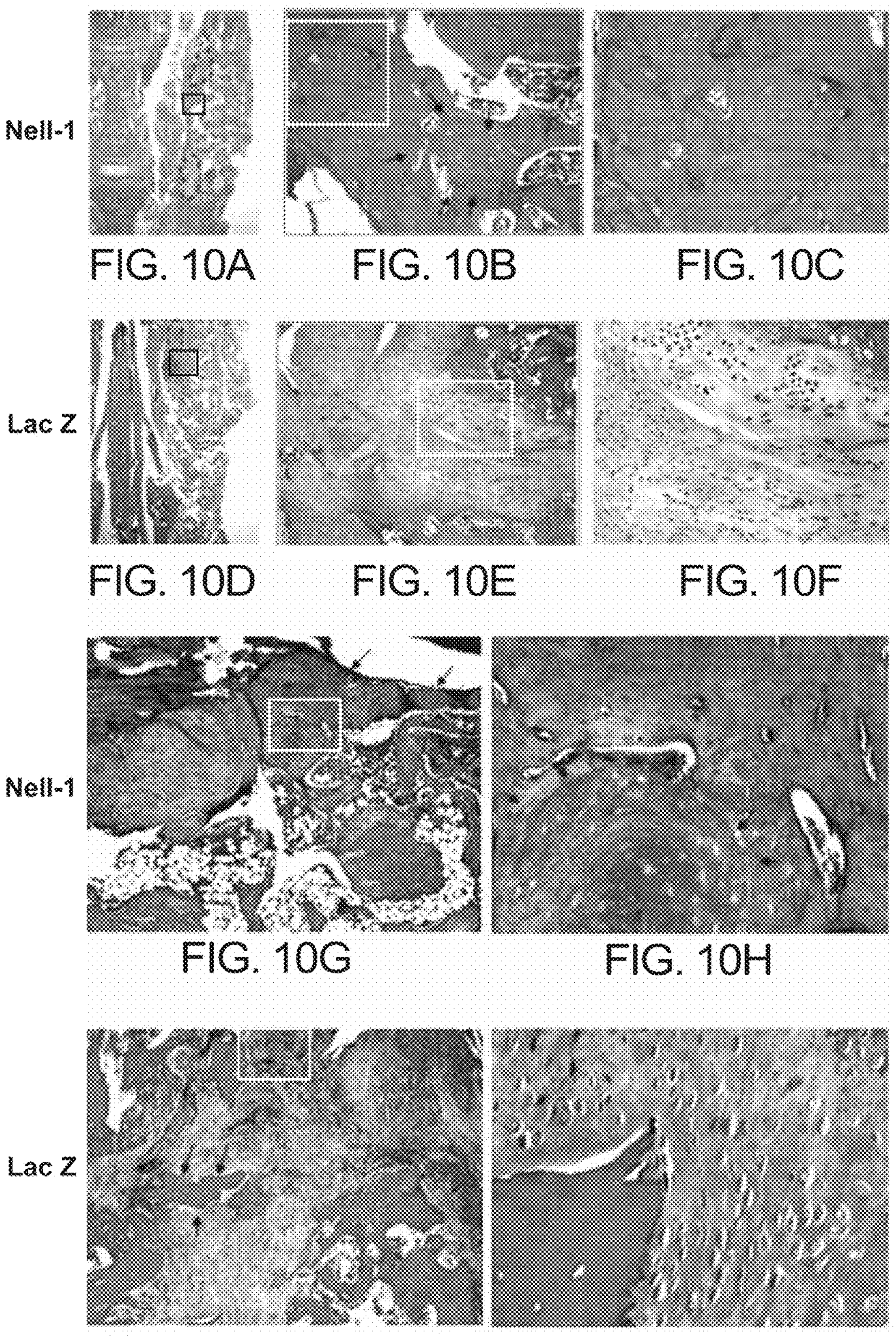
FIG. 10 show histology of 6-week samples of fusion by Nell1 (A, B, C, G and H) and nonunion with control (D, E, F, I and J). (A) Green arrows indicate cortical bone like bridging bone connecting two transverse processes denoted with dotted lines on H&E stained sections. (B and C) High power views of lamellar bones in defined area of the bridging bone from A. (D) H&E staining showed smaller bone mass close to a transverse process denoted with dotted line; (E and F) High power views of premature bones in defined area from D. (G and H) New bone growth as indicated with ostetocytes forming cement lines on Masson trichrome staining section. (I an J) More cartilaginous tissues emerging from remodeling DBMDBM particles (arrows). Original magnification for A and D: 9.8×; B, E, G and I: 100×; C, F, H and J: 200×. This data demonstrate that Nell1 can induce spinal fusion through bone bridge formation.

The term "bone conditions" can involve, but are not limited to: 1) modulation of bone healing and regeneration by increasing or decreasing bone formation such as after accidental or iatrogenic orthopedic injury [e.g., from trauma (e.g., long bone fractures) (see FIGS. 7B-D), or surgery (e.g., spinal fusion)], see FIGS. 2, 9 and 10) modulation of bone mass by increasing or decreasing bone formation without evidence of overt orthopedic injury [e.g., hip osteonecrosis, osteoporosis (decreased bone mass), osteopetrosis (increased bone mass)]; 3) modulation of bone healing and regeneration by increasing or decreasing bone formation such after accidental or iatrogenic craniofacial bone and/or periodontal injury [e.g., from trauma (e.g., craniofacial fractures), surgery (e.g., cleft lip/palate repair, cranial defect repairs) (see FIGS. 4, 5, and 6) or dental procedures (e.g., tooth extraction, dental implant placement)]; 4) modulation of bone mass by increasing or decreasing bone formation without evidence of overt craniofacial bone and/or periodontal injury (e.g., restoration and/or preservation of maxillary and mandibular alveolar dental ridges; inhibition of premature calvarial overgrowth across sutures); 5) modulation of bone healing and regeneration by increasing bone formation at sites of hardware implantation to facilitate osseous integration (e.g., total knee implants, dental implants, spinal implants) 6) modulation of cartilage healing and regeneration by modulating hypertrophic cartilage formation (e.g., prevent cartilage hypertrophy in bone conditions where non-hypertrophied cartilage is desirable such as intraarticular fractures causing severe joint injury, severe osteoarthritis or rheumatoid arthritis with progressive joint surface loss; promote cartilage hypertrophy in bone conditions where hypertrophied cartilage is desirable such as acceleration of endochondral ossification; prevent cartilage hypertrophy in bone conditions where hypertrophied cartilage is not desirable such as intramembranous ossification).

The term "stem cells" can involve, but are not limited to adult stem cells, fetal stem cells, embryonic stem cells, mesenchymal stem cells, and bone marrow stem cells.

Osteoblast Formation and Function

Osteoblast formation and function encompass two important aspects of bone biology (Aubin, J. E., Rev Endocr Metab Disord, 2001. 2(1): p. 81-94; Ducy, P., et al., Genes Dev, 1999. 13(8): p. 1025-36). Both concepts are central to osteoinduction and bone regeneration. According to Aubin (Aubin, 2001), osteoblast formation involves several differentiation stages consisting of initial mesenchymal stem cell (MSC) commitment to an osteoprogenitor lineage with eventual differentiation into osteoblasts and finally osteocytes and apoptotic cells. Osteoblast function, on the other hand, involves the activity of already differentiated osteoblasts in matrix deposition and bone formation. Bone formation, which requires both osteoblast formation and function, can occur during embryonic development, growth, remodeling, fracture repair, and experimentally by implanting decalcified bone matrix or adding purified BMP (Id.). Thus, osteoblast differentiation and function are two, but not necessarily distinct processes in so far as proper osteoblast function can only occur within the context of proper osteoblast differentiation.

Commitment of undifferentiated mesenchymal stem cells (MSCs) to an osteochondroprogenitor lineage is first marked by Cbfa1 expression (Nakashima, K. and B. de Crombrugghe, Trends Genet, 2003. 19(8): p. 458-66; Yamaguchi, A., T. Komori, and T. Suda, Endocr Rev, 2000. 21(4): p. 393-411). Cbfa1 is essential for both osteoblast formation and function. Cbfa1 null (Cbfa1$^{-/-}$) mice exhibit a complete lack of osteoblasts and osteogenesis and die in the perinatal stage from respiratory insufficiency secondary to the absence of a rigid rib cage to sustain respiration (Komori, T., et al., Cell, 1997. 89(5): p. 755-64; Otto, F., et al., Cell, 1997. 89(5): p. 765-71; Ducy, P., et al., Cell, 1997. 89(5): p. 747-54). Meanwhile, heterozygous Cbfa1 loss-of-function (Cbfa1$^{-/-}$) mice manifest clavicular hypoplasia, delayed development of membranous bones, and delayed ossification of cranial bones, causing open anterior and posterior fontanelles, smaller parietal and interparietal cranial bones, and multiple Wormian bones (small bones in the sutures), a phenotype similar to cleidocranial dysplasia (CCD) in humans (Otto, F., et al., Cell, 1997. 89(5): p. 765-71; Mundlos, S., et al., Cell, 1997. 89(5): p. 773-9). The phenotype of Cbfa1$^{+/-}$ mice suggests that intramembranous ossification may be particularly susceptible to Cbfa1 haplotype insufficiency.

According to published studies, most described osteoinductive factors appear to function upstream of Cbfa1 (Table 1). For instance, BMP2, BMP7, insulin-like growth factor-I (IGF-I), and transforming growth factor-β1 (TGF-β1) are known upregulate Cbfa1 transcription (Nakashima, K. and B. de Crombrugghe, Trends Genet, 2003. 19(8): p. 458-66; Tou, L., N. Quibria, and J. M. Alexander, Mol Cell Endocrinol, 2003. 205(1-2): p. 121-9; Pei, Y., et al., Acta Pharmacol Sin, 2003. 24(10): p. 975-84; Lee, M. H., et al., J Cell Biochem, 1999. 73(1): p. 114-25). Table 1 shows some documented osteoinductive factors: fibroblast growth factor 2 (FGF2), parathyroid hormone (PTH) (Franceschi, R. T. and G. Xiao, J Cell Biochem, 2003. 88(3): p. 446-54; Kim, H. J., et al., J Biol Chem, 2003. 278(1): p. 319-26), FGF receptor1 (FGFR1) (Zhou, Y. X., et al., Hum Mol Genet, 2000. 9(13): p. 2001-8), vascular endothelial growth factor (VEGF), which is an angiogenic factor (Zelzer, E., et al., Mech Dev, 2001. 106(1-2): p. 97-106) and platelet derived growth factor (PDGF), a multifunctional growth factors that may function cooperatively with Cbfa1 in growth plate vascularization (Himeno, M., et al., J Bone Miner Res, 2002. 17(7): p. 1297-305).

TABLE 1

Bone Graft Classification System

| Graft Type | Description | Disadvantages |
|---|---|---|
| Autograft | Bone graft taken from the patient | 1. Second surgical site<br>2. Prolonged anesthesia time<br>3. Short and long term donor site morbidity<br>4. Limited supply |
| Allograft based | Cadaveric bone graft. Can be deproteinized or demineralized. | 1. Risk for infection, disease transmission<br>2. Limited osteoinductive ability (in demineralized grafts only)<br>3. Limited supply |

TABLE 1-continued

| Bone Graft Classification System | | |
|---|---|---|
| Graft Type | Description | Disadvantages |
| Xenograft based | Deproteinized (but not demineralized) bone graft from non-human species (i.e., BioOss-a bovine graft) | 1. No osteoinductive ability<br>2. Somewhat limited supply<br>3. Risk for infection, disease transmission |
| Cell based | Seed patient's own cells into porous scaffolds | 1. Second surgical site<br>2. May require additional culture time and manipulation |
| Ceramic based | Examples include calcium phosphate, calcium sulfate, and bioglass | Only minor osteoinductive ability |
| Polymer based | Both degradable and nondegradable polymers | No osteoinductive ability |
| Growth Factor based | BMPs, non-BMPs (e.g., FGF, TGF-β, IGF, VEGF, PDGF, PTH/PTHrp)*, and gene therapy | 1. Need appropriate delivery or osteoconductive vehicle<br>2. Pleiotropic effects on multiple cells types<br>3. Unpredictable in vivo osteoinductive effects (i.e., for many, specificity depends on carrier) |

*Abbreviations: FGF (fibroblast growth factors), TGF-β (transforming growth factor-β), IGF (insulin-like growth factor), VEGF (vascular endothelial growth_factor), PDGF (platelet-derived growth factor), PTH (parathyroid hormone)/PTHrp (PTH-regulated protein)
Adapted in part from Laurencin, C. and Y. Khan, *Bone Graft Substitute Materials.* emedicine, 2004: p. www<dot>emedicine<dot>com</>orthoped</>topic611<dot>htm The osteoinductive properties of Cbfa1 have also been studied. Bone marrow stromal cells (BMSCs) transduced with an adenoviral Cbfa1 (Ad Cbfa1) demonstrated increased mineralization in vitro and increased bone formation in mouse critical-size calvarial defects (Zheng, H., et al., Calcif Tissue Int, 2004. 74(2): p. 194-203). Furthermore, AdCbfa1 and AdBMP2 co-transduction into C3H10T1/2 cells, a murine pluripotent mesenchymal cell line, synergistically stimulated osteoblast differentiation in vitro and markedly increased bone formation in vivo when the transduced C3H10T1/2 cells were subcutaneously implanted into immunodeficient mice (Franceschi, R. T., et al., Cells Tissues Organs, 2004. 176(1-3): p. 95-108; Yang, S., et al., J Bone Miner Res, 2003. 18(4): p. 705-15). These results show that the responsiveness of osteoprogenitor cell populations to BMPs can be enhanced in vitro and in vivo by Cbfa1, a major regulator of the osteoprogenitor lineage (Franceschi, R. T., et al., Cells Tissues Organs, 2004. 176 (1-3): p. 95-108).

NELL Peptides as Downstream Targets of Cbfa1

Figure 11A:
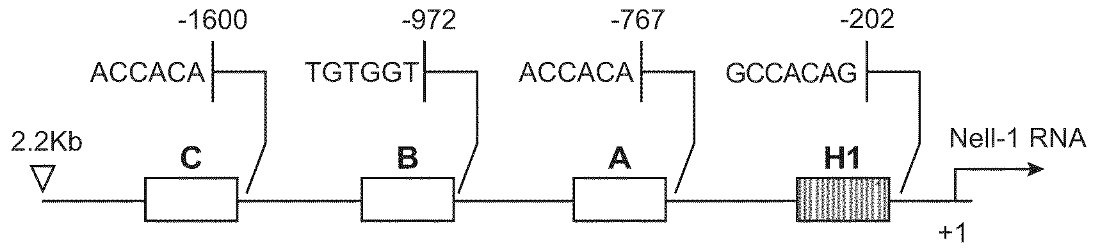
FIGS. 11A and 11B show the human, mouse and rat Nell1 promoters contain multiple OSE2 consensus motifs.
Figure 11B:
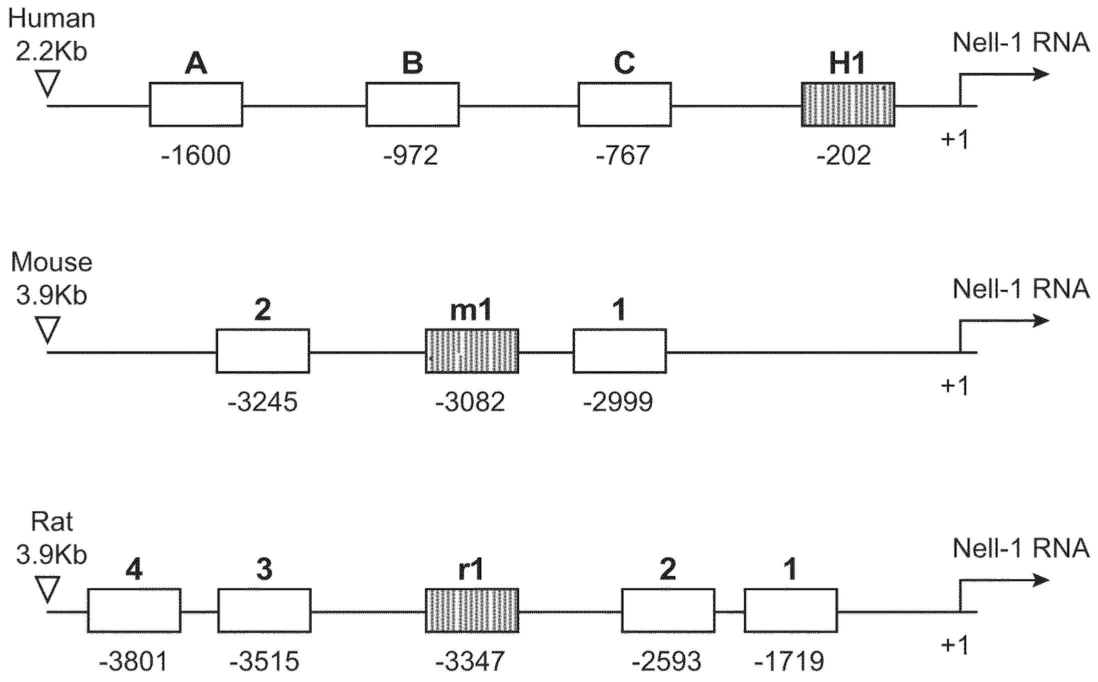

NELL peptides can be downstream targets of Cbfa1 (Kuroda, S., et al., Biochem. Biophys Res Commun, 1999. 265:79-86; Ting, K., et al., J Bone Miner Res, 1999. 14:80-89). Cbfa1 is known to promote transcription of many downstream osteoblastic genes such as α1 type I collagen (Col1-α1), Bone sialoprotein (Bsp), Osteopontin (Op), and Oc by binding to the osteoblast-specific cis-acting element 2 (OSE2) response elements in their promoter regions (Ducy, P., et al., Genes Dev, 1999. 13(8): p. 1025-36). Studies have shown the presence of three functional OSE2 response elements on the human NELL1 gene, confirming that NELL1 is a Cbfa1 regulated gene (see FIG. 11).

NELL1 was first noted to associate with bone formation when adenoviral NELL1 overexpression in vitro significantly increased differentiation and mineralization selectively in osteoblastic cells, but not in non-osteoblastic cells such as NIH3T3 fibroblasts (Zhang, X., et al., J Clin Invest, 2002. 110(6): p. 861-70) and when NELL1 overexpression in vivo significantly increased premature bone formation and bony calvarial overgrowth across cranial sutures of transgenic animals. As stated in the previous paragraph, NELL1 expression is downstream of and directly regulated by Cbfa1/Runx2, a critical mediator of osteoblast formation and function, indicating that NELL1 can act more specifically or preferentially on further differentiated osteogenic lineage cells (i.e., committed osteoblasts).

NELL1 is highly conserved across species. Rat and human NELL1 share a 93% predicted amino acid homology (Ting, K., et al., J Bone Miner Res, 1999. 14:80-89). NELL1 contains several highly conserved motifs including a secretory signal peptide, an $NH_2$-terminal TSP-1-like module, five chordin-like CR domains and six EGF-like domains (FIG. 1) (Kuroda, S., et al., Biochem Biophys Res Commun, 1999. 265(1): p. 79-86). Rat NELL1 is secreted into media as 400-kDa proteins that convert to 130-kDa proteins after prolonged denaturation (Id.). The 130-kDa monomers are assumed to associate into homotrimers via either the coiled-coil region or CR domains (Voorberg, J., et al., Journal of Cell Biology, 1991. 113(1): p. 195-205). Studies suggest that NELL1 may critically mediate some of the downstream effects of Cbfa1 such as continuing osteoblast differentiation and function (Ting, K., et al., J Bone Miner Res, 1999. 14:80-89) and function downstream of Cbfa1 (Zhang, X., et al., J Clin Invest, 2002. 110(6): p. 861-70; Otto, F., et al., Cell, 1997. 89(5): p. 765-71).

In vivo, endogenous NELL1 expression has been identified to correspond temporally and spatially with advancing osteogenic fronts of fusing sutures. Transgenic NELL1 overexpression mice also demonstrated pathological bony calvarial overgrowth across cranial sutures (Zhang, X., et al., J Clin Invest, 2002. 110(6): p. 861-70).

NELL1 as a downstream mediator of Cbfa1 in osteoblast differentiation and function is further established by functional compensation of some aspects of Cbfa1 deficiency by NELL1. In one study, $F_2$ progeny from intercrossed NELL1 overexpression mice ($NELL1^{overexp}$)) and $Cbfa1^{+/-}$ mice were examined. Minimal rescue of the osteoblastic phenotype was observed in $NELL1^{overexp}$+$Cbfa1^{-/-}$ mice, which presumably lack committed osteoblasts. In addition, $NELL1^{overexp}$ $Cbfa1^{-/-}$ mice demonstrated increased chondrocyte hypertrophy (see FIG. 7A) indicating that NELL1 is also important processes related to endochondral ossification. Nine of the eleven NELL1$^{overexp}$ Cbfa1$^{+/-}$ mice, which should contain committed, but imperfectly functioning osteoblasts, showed definitive rescue from the usual CCD-like phenotype (Otto, F., et al., Cell, 1997. 89(5): p. 765-71). Alizarin red and Alcian blue staining along with micro-CT analyses confirmed that fontanelle size and suture width were considerably smaller along with less hypoplastic clavicles in the NELL1$^{overexp}$ Cbfa1$^{+/-}$ mice compared to the non-rescued Cbfa1$^{+/-}$ mice (FIG. 2).

The studies have shown, among others, that: 1) Cbfa1 upregulates NELL1 expression; 2) NELL1 overexpression selectively increases osteoblastic-type differentiation (i.e., increased ALP activity, OP and OC expression) in susceptible cell types; 3) NELL1 overexpression acts on further differentiated osteogenic lineage cells (i.e., committed osteoblasts); and 4) NELL1 overexpression increases bony overgrowth across cranial sutures; 5) NELL1 overexpression can functionally compensate for some aspects of Cbfa1 deficiency; and 6) NELL1 overexpression selectively increases processes associated with endochondral bone formation (e.g., chondrocyte hypertrophy).

Figure 3A:
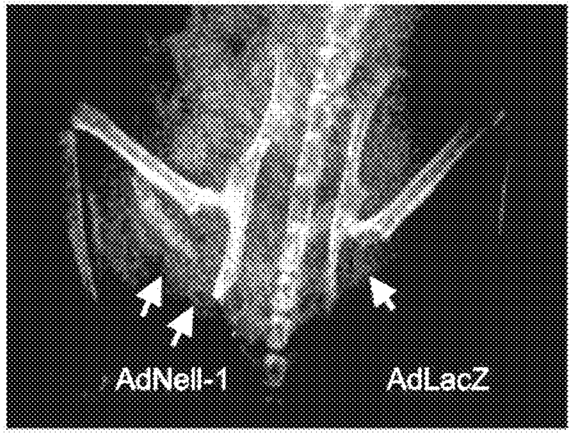
FIGS. 3A-C show that Nell-1 can differentiate bone marrow stem cells (BMSCs) into an osteoblastic phenotype.
Figure 3B:
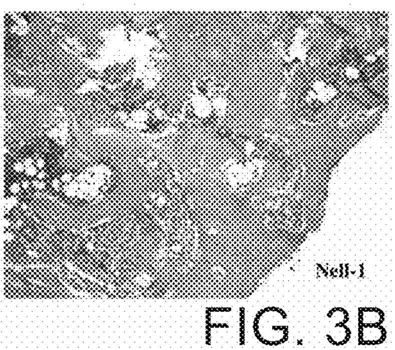
Figure 3C:
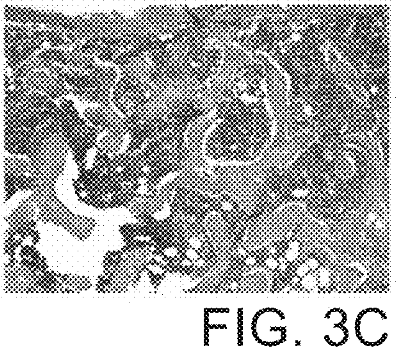

NELL peptides are also effective for non-craniofacial bone generation. For example, the in vitro effects of transduced AdNELL1 on bone marrow stromal cells (BMSC) isolated from long bones and the in vivo effects of AdNELL1 injection into nude mice were investigated. This study demonstrated that AdNELL1 transduced BMSC showed significantly increased mineralized bone nodule formation above Adβ-Galactosidase (Adβ-Gal) controls (FIG. 3), while AdNELL1 injection resulted in ectopic calcified nodule formation in muscle, showing that NELL1 can enhance non-craniofacial osteoblast differentiation and bone formation.

Figure 8A:
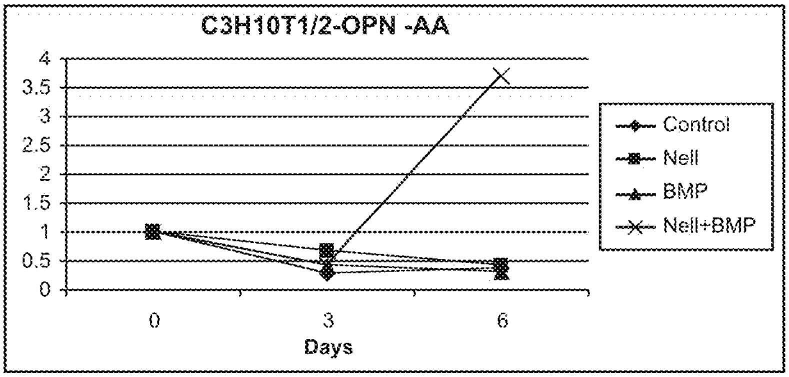
FIG. 8 shows synergistic effect of NELL1 with BMP2 in vitro (A) and in vivo (B, C). These data demonstrate that NELL1 and BMPs are synergistic in inducing osteoblastic differentiation marker expression and in inducing bone formation. (A) Real time PCR showing that Nell-1 and BMP2 synergistically induced osteopontin, an osteoblast differentiation marker. Nell-1 and BMP2 also synergistically induced osteocalcin, another osteoblast differentiation specific marker. (B) Arrows indicates Nell-1 and BMP2 cotransduction induced much more bone than either one of them individually. "L" indicates left; "R" indicates right. (C) Excised femur specimen from BMP2+Nell-1 treated (L) and BMP2 treated (R) animals showing significantly increased bone formation in the BMP2+Nell-1 treated animals.
Figure 8B:
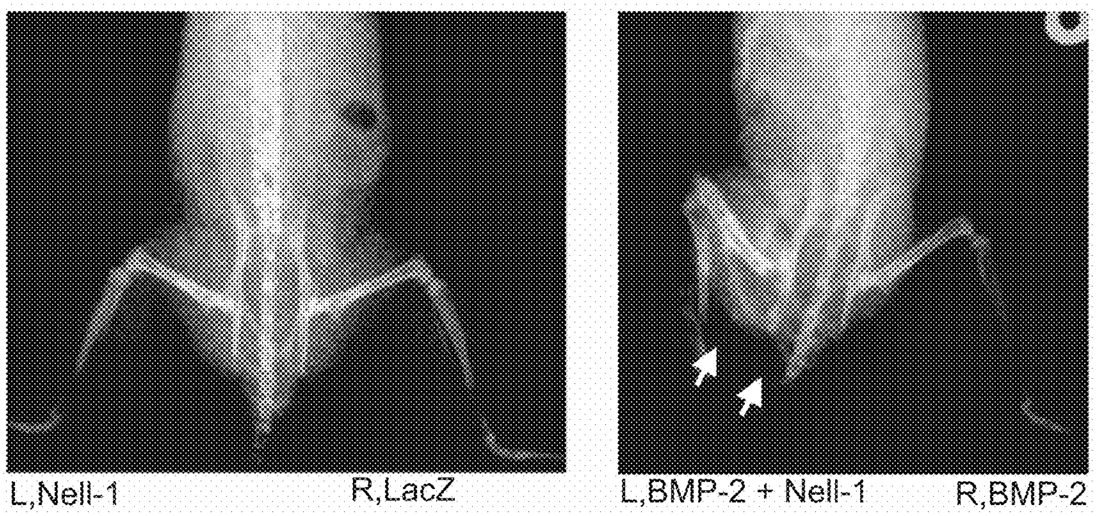
Figure 8C:
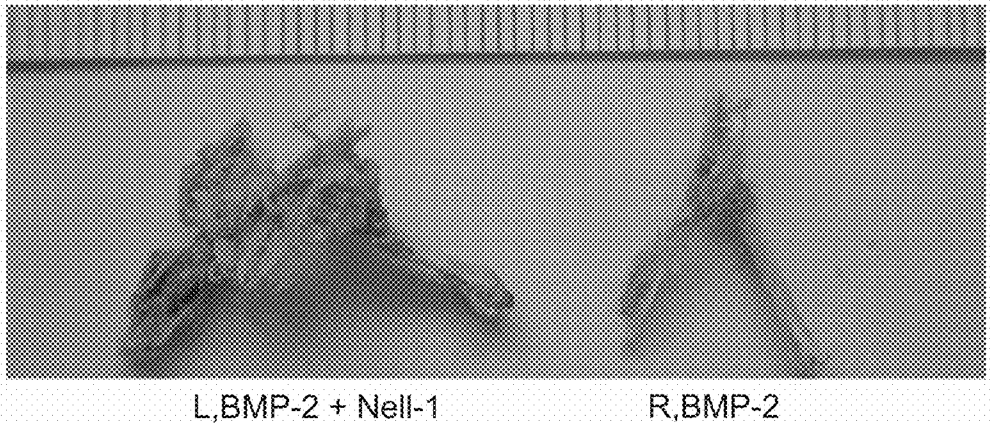

Furthermore, NELL peptides can also up-regulate osteoblast differentiation markers and work synergistically with a BMP protein, a TGFβ protein, FGF, IGF (insulin like growth factors), VEGF, or a combination thereof to increase expression of bone differentiation markers in vitro (e.g., ALP, OC) and bone formation in vivo (see FIG. 8). For example, NELL2 and BMP2 can be synergistic in inducing osteoblast differentiation. Examples as shown in FIG. 8 demonstrate that NELL peptides, such as NELL2 and NELL1, can modulate osteoblast differentiation to promote bone formation.

Accordingly, in some embodiments, the present invention provides a method for identifying a molecule that induces expression of a NELL peptide. The method includes: (1) contacting a NELL1 promoter gene with a test compound, (2) detecting the level of expression of the NELL1 promoter gene, (3) comparing the level of expression of the NELL1 promoter gene to the level of expression of the NELL1 promoter gene without the test compound, and (4) designating the test compound as a modulator of the expression of the NELL peptide if the level of expression of the NELL1 promoter gene with the test compound is different from the level of expression of the NELL1 promoter gene without the test compound. In some embodiments, the method step further comprises: (5) designating the modulator as an inhibitor of the expression of the NELL peptide if the level of expression of the NELL1 promoter gene with the test compound is lower than the level of expression of the NELL1 promoter gene without the test compound, or (6) designating the modulator as an enhancer of the expression of the NELL peptide if the level of expression of the NELL1 promoter gene with the test compound is higher than the level of expression of the NELL1 promoter gene without the test compound. A modulator identified according to the method can be used to modulate the expression of a NELL peptide in a mammal.

Systems Expressing NELL Peptides

A NELL1 peptide is a protein which can be expressed by the NELL1 gene or cDNA or RNA or any fragments thereof. Such NELL1 gene, cDNA, RNA or fragments thereof includes SEQ ID NO: 1-11, which encode human NELL1 peptide or a fragment thereof, SEQ ID NO: 17-71, which encode mouse NELL1 peptide or a fragment thereof, and SEQ ID NO: 75 and 76, which encode rat NELL1 peptide or a fragment thereof. The NELL1 peptide can include a NELL1 peptide fragment that retains the ability to induce osteogenic cell differentiation, osteoblast differentiation bone formation, or cartilage regeneration.

A NELL2 peptide is a protein which can be expressed by the NELL2 gene, cDNA or RNA or any fragments thereof. Such NELL2 gene, cDNA or RNA or any fragments thereof includes SEQ ID NO: 12-16, which encode human NELL2 peptide or a fragment thereof, SEQ ID NO: 72-74, which encode mouse NELL2 peptide or a fragment thereof, and SEQ ID NO: 77-81, which encode rat NELL2 peptide or a fragment thereof. The NELL2 peptide can include NELL2 peptide fragments that retain similar activity to the NELL2 peptide described herein.

The NELL1 or NELL2 peptide can be expressed in a nucleic acid construct that includes any of the above described NELL1 or NELL2 genes. In one embodiment, the invention includes a method of expressing a functional NELL peptide, such as NELL1 or NELL2 peptide, using an insect cell line. In one embodiment, the insect cell can be a high five cell, Sf9 and other Sf cells.

In one embodiment, the method can include providing a nucleic acid sequence encoding a NELL1 or NELL2 peptide described herein. The nucleic acid sequence can also include sequences such as those with substantial sequence similarity, such as sequences having at least about 75% sequence similarity with any portion of the sequences listed above.

In some embodiments, the nucleic acid can include an expression vector for expressing the nucleic acid sequence encoding a NELL peptide, such as NELL1 or NELL2 peptide. For example, the expression vector can be pIZT/V5-His (Invitrogen), and selective markers can also include blastcidin and neomycin.

In some embodiments, the nucleic acid sequence can also include additional nucleic acids which encode reporter products to monitor levels of gene expression, or encode peptide tags which can be visualized using known methods in the art to monitor levels of peptide expression. Additional sequences can be selected so as to not interfere with the expression of the nucleic acid, or the functionality of the expressed peptide product.

The nucleic acid construct can include a nucleic acid sequence encoding a signal peptide. Such a signal peptide can be any NELL signal peptide. Some examples of such signal peptide human, rat, mouse or dog NELL signal peptides. Some other examples of NELL signal peptides include, but are not limited, human NELL2 signal peptide SEQ ID NO: 89, which is encoded by nucleic acid SEQ ID NO: 88, rat NELL2 signal peptide SEQ ID NO: 91, which is encoded by nucleic acid SEQ ID NO: 90, mouse NELL2 signal peptide SEQ ID NO: 93, which is encoded by nucleic acid SEQ ID NO: 92, and dog NELL2 signal peptide SEQ ID NO: 95, which is encoded by nucleic acid SEQ ID NO:

94. The nucleic acid can include an expression vector for expressing the nucleic acid sequence encoding a NELL peptide. Further, the nucleic acid sequence can include additional nucleic acids which encode reporter products to monitor levels of gene expression, or encode peptide tags which can be visualized using known methods in the art to monitor levels of peptide expression.

Nucleic acid constructs can comprise expression and cloning vectors should containing a selection gene, also termed a selectable marker, such as a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g., ampicillin, neomycin, methotrexate or tetracycline, (b) complement auxotrophic deficiencies.

Nucleic acid constructs can also include a promoter which is recognized by the host organism and is operably linked to the NELL encoding nucleic acid. Promoters are untranslated sequences located upstream from the start codon of a structural gene (generally within about 100 to 1000 bp) that control the transcription and translation of nucleic acid under their control, including inducible and constitutive promoters. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. Some examples of NELL1 promoter nucleic acid sequence include, but are not limited to, SEQ ID NO: 82, 84, and 86, which encode a human NELL1 promoter, a mouse NELL1 promoter, and a rat NELL1 promoter, respectively. Some examples of NELL2 promoter nucleic acid sequence include, but are not limited to, SEQ ID NO: 83, 85, and 87, which encode a human NELL2 promoter, a mouse NELL2 promoter, and a rat NELL2 promoter, respectively.

A nucleic acid can be operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation.

In one embodiment, the invention can include a nucleic acid construct for expressing a NELL peptide, such as NELL1 and/or NELL2 peptide in a mammalian cell such as a Chinese hamster ovary cell (CHO cell). The nucleic acid sequence can be a cDNA, genomic DNA, or RNA, encoding at least a functional portion of a NELL peptide. For example, the nucleic acid sequence can include a NELL1 or NELL2 gene described above. In some embodiments, the nucleic acid sequence can also include sequences such as those with substantial sequence similarity, such as sequences having at least about 75% sequence similarity with any portion of the sequences listed above.

In some embodiments, for production of NELL1 and/or NELL2 peptides in mammalian cells (e.g., CHO cells), the expressing system for NELL1 and/or NELL2 can include the nucleic acid or cDNA that expresses the endogenous signal peptide. In some embodiments, the expressing system for NELL1 and/or NELL2 peptides can include the nucleic acid or cDNA that expresses NELL2 signal peptide. The incorporation of the NELL2 signal nucleic acid or cDNA into the system expressing NELL1 peptide allows the production of the NELL1 peptide more efficiently.

In one embodiment, the invention can include cells that express functional NELL peptides. In one embodiment, the cell can be an insect cell. In one embodiment, the insect cell can be a high five cell.

In one embodiment, the cell can be transfected with a nucleic acid construct encoding a NELL peptide. For example, the cell line can be transfected transiently or stably with the nucleic acid construct encoding a NELL peptide. In one embodiment, NELL expressing nucleic acids (e.g., cDNA(s) can be cloned into gene expression vector or viral particles that are competent to transfect cells (such as insect cells or Chinese hamster ovary cells (CHO cells)). In some embodiments, the construct can include a vector such as pTB701 using a signal peptide, which can be any of Pre-protrypsin, human tPA, immunoglobulin light chain of Ig, and Fc fragment, interleukin. The pTB701 vector was reported in Kuroda et al., Biochemical & Biophysical Research Communications, 265:79-86 (1999).

The nucleic acid sequence can also include a nucleic acid sequence encoding a NELL peptide, such as NELL1 or NELL2 peptide, in frame with a nucleic acid sequence encoding an insect secretory signal peptide.

In one embodiment, the invention can include cells that express functional NELL peptides, and can secrete functional proteins.

In one embodiment, the invention can include a polypeptide (amino acid sequence) comprising a NELL peptide, such as NELL1 or NELL2 peptide, and can include secretory signal peptide.

In some embodiments, gene sequences expressing NELL peptide or proteins can include any gene sequences that express the whole NELL molecule or a fragment thereof. Such gene sequences can optionally include noncoding sequences. Generally, genome sequences can be roughly classified as: (1) genome sequences that code for functional proteins (this can include different mRNA splice variants), (2) noncoding, non-transcribed genome sequences that may modulate expression of functional proteins (promoter regions, other non-transcribed DNA regions, etc), and (3) noncoding, transcribed genome sequences that may modulate expression of functional proteins (e.g., tRNA and rRNA, but also introns, 5' and 3'-UTR, transposables elements, intergenic regions and interestingly thousands of different small stable RNA with or without antisense capabilities.

Each DNA molecule contains many genes—the basic physical and functional units of heredity. A gene is a specific sequence of nucleotide bases, whose sequences carry the information required for constructing proteins, which provide the structural components of cells and tissues as well as enzymes for essential biochemical reactions. The human genome is estimated to comprise more than 30,000 genes.

Human genes vary widely in length, often extending over thousands of bases, but only about 10% of the genome is known to include the protein-coding sequences (exons) of genes. Interspersed within many genes are intron sequences, which have no coding function. The balance of the genome is thought to consist of other noncoding regions (such as control sequences and intergenic regions), whose functions are obscure. All living organisms are composed largely of proteins; humans can synthesize at least 100,000 different kinds. Proteins are large, complex molecules made up of long chains of subunits called amino acids. Twenty different kinds of amino acids are usually found in proteins. Within the gene, each specific sequence of three DNA bases (codons) directs the cells protein-synthesizing machinery to add specific amino acids. For example, the base sequence ATG codes for the amino acid methionine. Since 3 bases code for 1 amino acid, the protein coded by an average-sized gene (3000 bp) will contain 1000 amino acids. The genetic code is thus a series of codons that specify which amino acids are required to make up specific proteins.

The protein-coding instructions from the genes are transmitted indirectly through messenger ribonucleic acid (mRNA), a transient intermediary molecule similar to a single strand of DNA. For the information within a gene to be expressed, a complementary RNA strand is produced (a process called transcription) from the DNA template in the nucleus. This mRNA is moved from the nucleus to the cellular cytoplasm, where it serves as the template for protein synthesis. The cells protein-synthesizing machinery then translates the codons into a string of amino acids that will constitute the protein molecule for which it codes. In the laboratory, the mRNA molecule can be isolated and used as a template to synthesize a complementary DNA (cDNA) strand, which can then be used to locate the corresponding genes on a chromosome map.

In some embodiments, the composition described herein includes can be stabilized by binding with other chemicals or by incorporating in nanocage or biomaterial until successful delivery. There are more noncoding regions than coding regions in humans. The noncoding part of genomes plays an important regulatory role. At least half of the human genome is transcribed. Around 95% of this transcriptional output is non coding RNA (ncRNA) encompassing not only tRNA and rRNA, but also introns, 5' and 3'-UTR, transposables elements, intergenic regions and interestingly thousands of different small stable RNA. The nanocage or biomaterial can be a carrier or scaffold described below.

A number of these transcribed regions are evolutionarily conserved between human and rodents (up to 95% conservation between man and mouse), suggesting preserved functions. An essential characteristic of a wide fraction of these noncoding RNA is their antisense capabilities: they can target another RNA through more or less extended base pairing complementarities. This has been demonstrated for snoRNA and miRNA. NcRNA are fulfilling some unexpected functions. They play an important role in regulating cellular processes including development, heterochromatin formation, transcription, alternative splicing and editing, chemical modification of nucleic acids and genomic stability in eukaryotes. While most ncRNA with precisely described functions are ubiquitous, most newly identified ncRNA have been found to be developmentally regulated, i.e., expressed in a gender-, tissue- or cell-specific manner. Among the antisense ncRNA, a large family is rapidly emerging: the micro-RNA (miRNA). They are highly conserved among higher organisms, are involved in temporal cell lineage decision and tissue-specific gene regulation and regulate various developmental and physiological processes. Their common mode of action is to target mRNA for destruction or inhibition of translation.

Inhibitors of NELL Peptide

In one aspect of the present invention, the pharmaceutical composition disclosed herein can include an agent that inhibits the activity of a NELL peptide for treating, preventing or ameliorating a bone condition associated with premature or excessive bone generation. The agent can be, but not limited to, a NELL1 inhibitor or NELL2 inhibitor or a combination thereof. The term "inhibitor of NELL peptides" has been previously described in the Summary section.

Any assay methods of screening for an inhibitor of a bioactive compound such as a protein can be used to screen for inhibitors of NELL peptides. Some assay methods are described in PCT/2003/029281 (WO 2004/024893).

Representative NELL1 or NELL2 inhibitors include any agents that can specifically inhibit NELL1 or NELL2 at the transcriptional stage (e.g., Cbfa1 specific siRNA, antibodies, since NELL1 or NELL2 contains Cbfa1 binding sites in the promoter) and/or translational stage (e.g., NELL-1 specific siRNA, NELL2 specific siRNA, or receptors binding NELL1 or NELL2 such as NELL-1 or NELL2 specific antibodies).

Enhancers of NELL Peptides

In another embodiment, it is provided a pharmaceutical composition that includes one or more enhancers of NELL peptides.

Modulators of Receptors of NELL Peptides

In a further aspect of the present invention, the pharmaceutical composition provided herein can include a modulator of a receptor of NELL peptide. NELL1 and NELL2 proteins are secretory molecules which bind to membrane bound receptors (Kuroda, S., et al., Biochem Biophys Res Commun, 265(1): p. 79-86) (1999).

Modulators of the receptors of NELL peptides can be identified by any established method for screening for modulators of a receptor. In one embodiment, the modulators of the receptors of NELL peptides can be screened for by competitive binding. For example, one method of screening for such modulators can include the following steps: (1) contacting a receptor molecule of a NELL peptide with a test compound, (2) contacting the NELL peptide with the receptor molecule and the test compound, (3) detecting the extent of binding of the NELL peptide to the receptor molecule with the test compound, (4) comparing the extent of binding of the NELL peptide to the receptor molecule with the test compound with the extent of binding of a control wherein the control is obtained by detecting the extent of binding of the NELL peptide to the receptor molecule without the test compound, and (5) designating the test compound as a modulator of the receptor of the NELL peptide if the extent of binding of the NELL peptide to the receptor molecule with the test compound is different from the extent of binding of the control. The modulators can be designated as an antagonist or an agonist of the receptor. If the extent of binding of the NELL peptide to the receptor molecule with the test compound is lower than the extent of binding of the control, the modulator is an antagonist of the receptor of the NELL peptide. If the extent of binding of the NELL peptide to the receptor molecule with the test compound is higher than the extent of binding of the control, the modulator is designated as an agonist of the receptor of the NELL peptide.

In some embodiments, the NELL modulators described herein can include molecules that stabilize or degrade NELL and/or NELL receptors, as well as molecules that are involved in the stabilization and phosphorylation of the NELL-receptor complex after initial receptor ligation. In some embodiments, the modulators described herein can include agonists and antagonists of the aforementioned agonists and antagonists. For example, a composition including inhibitors of NELL-antagonists can increase bone metabolism. In all cases, please expand the clinical applications to include those discussed in previous paragraph.

Modulators of a receptor of a NELL peptide can be screened for by manual testing or by an automated system such as a system based on combinatorial chemistry. One example of the screening system based on combinatorial chemistry is described in PCT/2003/029281 (WO 2004/024893).

Cartilage Regeneration

Articular cartilage is comprised of mostly water (60-80 wt %) and the remaining ECM comprises mostly type II collagen (50-90% dry mass) and proteoglycans (5-10%). Other collagens and minor ECM molecules have been identified in small quantities. It is organization of the ECM into distinct zones, and the interaction between water and the ECM in the various zones that provide the toughness that is required for the absorption and transmission of biomechanical forces across joints, and simultaneously the frictionless articulating surfaces that are needed for joint motion. Stresses as high as 4 and 20 MPa have been reported in human hip joints during routine walking and jumping, respectively! As amazing as the articular cartilage is, it exhibits unfortunately minimal capacity for repair. Over 20 million Americans suffer from osteoarthritis and degenerative joint diseases with an associated annual healthcare burden of over $60 billion. A wide array of scaffolds, cytokines, and growth factors have been investigated for cartilage tissue engineering (see, e.g., Frenkel, S. R., et al., Ann. Biomed. Eng. 32:26-34 (2004); Tuli, R., et al., Arthritis Res. Ther. 5:235-238 (2003); and Ashammakhi, N. and Reis, R L. Topics in Tissue Engineering, Vol. 2, 2005). The role of static vs. dynamic compression, shear stress, hydrostatic pressure, fluid flow, electrical streaming potentials, bioreactors, and complex loading on chondrocyte biological response and tissue remodeling have been investigated extensively and the mechanotransduction pathways reviewed Ashammakhi, N. and Reis, R L. Topics in Tissue Engineering, Vol. 2, 2005) (see FIGS. 7A-D).

Accordingly, in a further aspect of the present invention, the pharmaceutical composition provided herein includes at least a NELL peptide or an agonist of the receptor of NELL peptides in an amount effective for inducing chondroblast and chondrocyte to form cartilage. NELL proteins, peptides, DNA, RNA, and NELL agonists, and antagonist inhibitors can be used alone or in conjunction with scaffolds with and without cells, with or without mechanical stimulation, in the presence or absence of additional growth factors. For example, in one embodiment, the pharmaceutical composition can be effective in regenerate cartilage in intervertebral disc, articular cartilage repair and regeneration. In another embodiment, the pharmaceutical composition can be effective in forming cartilage via ex vivo gene therapy and protein application to cells with or without scaffold in tissue engineering.

Depending on the delivery method and the local environment, a composition including a NELL peptide (e.g., a NELL1 peptide) can be used to induce an osteogenic cell, as such as a chondrocyte or chondroblast, to differentiate and form cartilage only. For example, in an articular cartilage defect, the composition described herein can induce an osteogenic cell such as chondrocyte/blast to form cartilage only. The composition can be applied to the defected cartilage area as a scaffold/carrier. In some embodiments, the composition can optionally include cells (stem cells, chondroblast etc). In some embodiments, the composition can be applied as gene therapy.

In some yet embodiments, the composition can be used in cartilage tissue engineering. For example, when chondroblasts are cultured on an "oscillating", intermittent stress tension environment, NELL1 peptide can include the chondroblast cells to differentiate and form cartilage. In these embodiments, the duration of application of the oscillating stress also plays an important role. For example, if the oscillating force is applied continuously, the composition having a NELL1 peptide can induce endochondral bone formation. Therefore, in the application of the oscillating stress shall be intermittently such that the differentiation of an osteogenic cell (e.g., chondrocyte/blast) can stop at the cartilage stage and thus prevent the cell from differentiating into endochondral bone formation.

Therefore, in some embodiments, the composition described herein can be used to regenerate/repair cartilage, e.g., for disc repair in articular cartilage and intervertebral disc.

Other exemplary cartilage conditions that can be treated, prevented, or ameliorated by a pharmaceutical composition disclosed herein include, but are not limited to, chondrocalcinosis, osteoarthritis, and/or other diseases characterized by pathological cartilage degeneration.

Other Agents

In some embodiments, the pharmaceutical composition described herein may include a NELL peptide and other agents effective for promoting bone generation. Such other agents include, e.g., a bone morphogenetic protein (BMP) such as BMP-1, BMP-2, BMP-3, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, BMP-19, BMP-20, BMP-21, FGF (fibroblast growth factors, e.g., FGF1 FGF2, FGF4, FGF7, FGF10, FGF19, FGF21, FGF23), TGF-β(transforming growth factor-β, e.g., TGF-β1), IGF (insulin-like growth factor, e.g., IGF-I), VEGF (vascular endothelial growth factor), PDGF (platelet-derived growth factor), PTH (parathyroid hormone)/PTHrp (PTH-regulated protein), oxysterols, lipophilic statins, growth/differentiation factor 5 (GDF5); and LIM mineralization proteins (LMPs) of which at least three splice variants exist. Some studies concerning these factors and mechanisms through which they act are described in Nakashima, K. and B. de Crombrugghe, Trends Genet, 2003. 19(8): p. 458-66; Tou, L., N. Quibria, and J. M. Alexander, Mol Cell Endocrinol, 2003. 205(1-2): p. 121-9; Pei, Y., et al., Acta Pharmacol Sin, 2003. 24(10): p. 975-84; Lee, M. H., et al., J Cell Biochem, 1999. 73(1): p. 114-25; Franceschi, R. T. and G. Xiao, J Cell Biochem, 2003. 88(3): p. 446-54; Kim, H. J., et al., J Biol Chem, 2003. 278(1): p. 319-26; Zelzer, E., et al., Mech Dev, 2001. 106(1-2): p. 97-106; Himeno, M., et al., J Bone Miner Res, 2002. 17(7): p. 1297-305; Kha, H. T. et al. J Bone Miner Res 19, 830-40, 2004; Izumo, N. et al. Methods Find Exp Clin Pharmacol 23, 389-94, 2001; Hatakeyama, Y. et al. J Cell Biochem 91, 1204-17, 2004; Pola, E. et al. Gene Ther 11, 683-93, 2004). One study reported that activating mutations in FGF receptor1 (FGFR1) dramatically increased Cbfa1 expression, osteoblast proliferation and differentiation, and bony calvarial overgrowth across cranial sutures in mice (Zhou, Y. X., et al., Hum Mol Genet, 2000. 9(13): p. 2001-8).

In one embodiment, the pharmaceutical composition contains a NELL1 peptide and a BMP peptide. As an example, a human osteosarcoma cell line, Saos-2 (McQuillan, D. J., et al., Bone, 1995. 16(4): p. 415-26; Fedde, K. N., Bone Miner, 1992. 17(2): p. 145-51), is cultured with recombinant NELL1 and BMP2 proteins at 100 ng/ml and 200 ng/ml, respectively. The test results demonstrated up to 5-fold increase in ALP activity in combined NELL1/BMP2 cultures relative to BMP2 cultures, showing that NELL1 can enhance the responsiveness of osteoblast-like cell populations to BMPs.

In some embodiments, the composition described herein can optionally include a LIM protein.

In some embodiments, the composition described herein can specifically exclude one or more the above described agents.

Dosages

Dosages of NELL peptides and other agents can be determined according to methods known in the art based on type of agent, the disease, and other factors such as age and gender.

In one embodiment, the dosage of NELL peptide for bone formation generally ranges from 0.001 pg/mm$^2$ to 1 pg/mm$^2$, or more preferably from 0.001 ng/mm$^2$ to 1 ng/mm$^2$, or more preferably from 0.001 μg/mm$^2$ to 1 μg/mm$^2$, or more preferably from 0.001 mg/mm$^2$ to 1 mg/mm$^2$, or more preferably from 0.001 g/mm$^2$ to 1 g/mm$^2$, with or without a particular carrier or scaffold. In another embodiment, the dosage of NELL peptide for bone formation generally ranges from 0.001 pg/ml to 1 pg/ml, or more preferably from 0.001 ng/ml to 1 ng/ml, or more preferably from 0.001 μg/ml to 1 μg/ml, or more preferably from 0.001 mg/ml to 1 mg/ml, or more preferably from 0.001 g/ml to 100 g/ml, with or without a particular carrier or scaffold. In yet another embodiment, the dosage of NELL peptide for bone formation generally ranges from 0.001 pg/kg to 1 pg/kg, or more preferably from 0.001 ng/kg to 1 ng/kg, or more preferably from 0.001 μg/kg to 1 μg/kg, or more preferably from 0.001 mg/kg to 1 mg/kg, or more preferably from 0.001 gm/kg to 1 gm/kg, more preferably from 0.001 kg/kg to 1 kg/kg with or without a particular carrier or scaffold. Furthermore, it is understood that all dosages may be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth.

However, because NELL peptides may have effects on in vitro osteoblast apoptosis (Zhang, X., et al., J Bone Miner Res, 2003. 18(12): p. 2126-34), NELL dosages (e.g., NELL1 dosages) that are significantly above an optimal range may not increase bone formation. Accordingly, even more preferable dosages of NELL peptide shall not be significantly above the optimal dosage range. The even more preferable optimal dosage ranges of NELL peptides may vary according to factors such as the type, the age, the location, and the gender of a mammalian subject; the carrier or scaffold material employed; and the purity and potency of different NELL peptides. In one embodiment, the even more preferable optimal dosage ranges of NELL peptides includes but are not limited to 1 ng/mm$^2$ to 100 ng/mm$^2$, or even more preferably from 100 ng/mm$^2$ to 1000 ng/mm$^2$, or even more preferably from 1 μg/mm$^2$ to 100 μg/mm$^2$, or even more preferably from 100 μg/mm$^2$ to 1000 μg/mm$^2$. In another embodiment, the even more preferable optimal dosage ranges of NELL peptides includes but are not limited to 1 ng/ml to 100 ng/ml, or even more preferably from 100 ng/ml to 1000 ng/ml, or even more preferably from 1 μg/ml to 100 μg/ml, or even more preferably from 100 μg/ml to 1000 μg/ml. In yet another embodiment, even more preferable optimal dosage ranges of NELL peptide for bone formation generally ranges from 1 μg/kg to 100 μg/kg, or even more preferably from 100 μg/kg to 1000 μg/kg, or even more preferably from 1 mg/kg to 100 mg/kg with or without a particular carrier or scaffold. Furthermore, it is understood that all dosages may be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth. As used herein, the term "significantly above the optimal range" means, e.g., about 1% to about 50%, about 5% to about 50%, about 10% to about 50%, about 20% to about 50%, about 30% to about 50%, or about 40% to 50% over the optimal range.

The dosage for inhibitors of NELL peptides varies according to the type of the inhibitor, the bone or cartilage condition to be treated, prevented, or ameliorated, and the age, the location, and the gender of the mammalian subject receiving the pharmaceutical composition containing the inhibitor. Generally, the dosage for inhibitors of NELL peptides ranges from but at not limited to: 0.001 pg/mm$^2$ to 1 pg/mm$^2$, or more preferably from 0.001 ng/mm$^2$ to 1 ng/mm$^2$, or more preferably from 0.001 μg/mm$^2$ to 1 μg/mm$^2$, or more preferably from 0.001 mg/mm$^2$ to 1 mg/mm$^2$, or more preferably from 0.001 g/mm$^2$ to 1 g/mm$^2$, with or without a particular carrier or scaffold. In another embodiment, the dosage for inhibitors of NELL peptides generally ranges from 0.001 pg/ml to 1 pg/ml, or more preferably from 0.001 ng/ml to 1 ng/ml, or more preferably from 0.001 μg/ml to 1 μg/ml, or more preferably from 0.001 mg/ml to 1 mg/ml, or more preferably from 0.001 g/ml to 100 g/ml, with or without a particular carrier or scaffold. In yet another embodiment, the dosage for inhibitors of NELL peptides generally ranges from 0.001 pg/kg to 1 pg/kg, or more preferably from 0.001 ng/kg to 1 ng/kg, or more preferably from 0.001 μg/kg to 1 μg/kg, or more preferably from 0.001 mg/kg to 1 mg/kg, or more preferably from 0.001 gm/kg to 1 gm/kg, more preferably from 0.001 kg/kg to 1 kg/kg with or without a particular carrier or scaffold. Furthermore, it is understood that all dosages may be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth.

The dosage for modulators of receptors of NELL peptides varies according to the type of the inhibitor, the type of receptor, the bone or cartilage condition to be treated, prevented, or ameliorated, and the age, the location, and the gender of the mammalian subject receiving the pharmaceutical composition containing the modulators of receptors of NELL peptides. Generally, the dosage for modulators of receptors of NELL peptides ranges from but at not limited to: 0.001 pg/mm$^2$ to 1 pg/mm$^2$, or more preferably from 0.001 ng/mm$^2$ to 1 ng/mm$^2$, or more preferably from 0.001 μg/mm$^2$ to 1 μg/mm$^2$, or more preferably from 0.001 mg/mm$^2$ to 1 mg/mm$^2$, or more preferably from 0.001 g/mm$^2$ to 1 g/mm$^2$, with or without a particular carrier or scaffold. In another embodiment, the dosage for modulators of receptors of NELL peptides generally ranges from 0.001 pg/ml to 1 pg/ml, or more preferably from 0.001 ng/ml to 1 ng/ml, or more preferably from 0.001 μg/ml to 1 μg/ml, or more preferably from 0.001 mg/ml to 1 mg/ml, or more preferably from 0.001 g/ml to 100 g/ml, with or without a particular carrier or scaffold. In yet another embodiment, the dosage for modulators of receptors of NELL peptides generally ranges from 0.001 pg/kg to 1 pg/kg, or more preferably from 0.001 ng/kg to 1 ng/kg, or more preferably from 0.001 μg/kg to 1 μg/kg, or more preferably from 0.001 mg/kg to 1 mg/kg, or more preferably from 0.001 gm/kg to 1 gm/kg, more preferably from 0.001 kg/kg to 1 kg/kg with or without a particular carrier or scaffold. Furthermore, it is understood that all dosages may be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth.

Formulation Carriers

The pharmaceutical composition described herein may be administered to a subject in need of treatment by a variety of routes of administration, including orally and parenterally, (e.g., intravenously, subcutaneously or intramedullary), intranasally, as a suppository or using a "flash" formulation, i.e., allowing the medication to dissolve in the mouth without the need to use water, topically, intradermally, subcutaneously and/or administration via mucosal routes in liquid or solid form. The pharmaceutical composition can be formulated into a variety of dosage forms, e.g., extract, pills, tablets, microparticles, capsules, oral liquid.

There may also be included as part of the pharmaceutical composition pharmaceutically compatible binding agents, and/or adjuvant materials. The active materials can also be mixed with other active materials including antibiotics, antifungals, other virucidals and immunostimulants which do not impair the desired action and/or supplement the desired action.

In one embodiment, the mode of administration of the pharmaceutical composition described herein is oral. Oral compositions generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. Some variation in dosage will necessarily occur, however, depending on the condition of the subject being treated. These preparations should produce a serum concentration of active ingredient of from about 0.01 nM to 1,000,000 nM, e.g., from about 0.2 to 40 μM. A preferred concentration range is from 0.2 to 20 μM and most preferably about 1 to 10 μM. However, the concentration of active ingredient in the drug composition itself depends on bioavailability of the drug and other factors known to those of skill in the art.

In another embodiment, the mode of administration of the pharmaceutical compositions described herein is topical or mucosal administration. A specifically preferred mode of mucosal administration is administration via female genital tract. Another preferred mode of mucosal administration is rectal administration.

Various polymeric and/or non-polymeric materials can be used as adjuvants for enhancing mucoadhesiveness of the pharmaceutical composition disclosed herein. The polymeric material suitable as adjuvants can be natural or synthetic polymers. Representative natural polymers include, for example, starch, chitosan, collagen, sugar, gelatin, pectin, alginate, karya gum, methylcellulose, carboxymethylcellulose, methylethylcellulose, and hydroxypropylcellulose. Representative synthetic polymers include, for example, poly(acrylic acid), tragacanth, poly(methyl vinylether-co-maleic anhydride), poly(ethylene oxide), carbopol, poly(vinyl pyrrolidine), poly(ethylene glycol), poly(vinyl alcohol), poly(hydroxyethylmethylacrylate), and polycarbophil. Other bioadhesive materials available in the art of drug formulation can also be used (see, for example, Bioadhesion—Possibilities and Future Trends, Gurny and Junginger, eds., 1990).

It is to be noted that dosage values also varies with the specific severity of the disease condition to be alleviated. It is to be further understood that for any particular subject, specific dosage regimens should be adjusted to the individual need and the professional judgment of the person administering or supervising the administration of the aforesaid compositions. It is to be further understood that the concentration ranges set forth herein are exemplary only and they do not limit the scope or practice of the invention. The active ingredient may be administered at once, or may be divided into a number of smaller doses to be administered at varying intervals of time.

The formulation may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. Materials used in preparing these various compositions should be pharmaceutically pure and non-toxic in the amounts used.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methylparabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

The pharmaceutical compositions of the present invention are prepared as formulations with pharmaceutically acceptable carriers. Preferred are those carriers that will protect the active compound against rapid elimination from the body, such as a controlled release formulation, including implants and microencapsulated delivery systems. Biodegradable, biocompatable polymers can be used, such as polyanhydrides, polyglycolic acid, collagen, and polylactic acid. Methods for preparation of such formulations can be readily performed by one skilled in the art.

Liposomal suspensions (including liposomes targeted to infected cells with monoclonal antibodies to viral antigens) are also preferred as pharmaceutically acceptable carriers. Methods for encapsulation or incorporation of compounds into liposomes are described by Cozzani, I.; Jori, G.; Bertoloni, G.; Milanesi, C.; Sicuro, T. Chem. Biol. Interact. 53, 131-143 (1985) and by Jori, G.; Tomio, L.; Reddi, E.; Rossi, E. Br. J. Cancer 48, 307-309 (1983). These may also be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Other methods for encapsulating compounds within liposomes and targeting areas of the body are described by Sicuro, T.; Scarcelli, V.; Vigna, M. F.; Cozzani, I. Med. Biol. Environ. 15(1), 67-70 (1987) and Jori, G.; Reddi, E.; Cozzani, I.; Tomio, L. Br. J. Cancer, 53(5), 615-21 (1986).

The pharmaceutical composition described herein may be administered in single (e.g., once daily) or multiple doses or via constant infusion. The compounds of this invention may also be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the compounds of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like according to a specific dosage form.

Thus, for example, for purposes of oral administration, tablets containing various excipients such as sodium citrate, calcium carbonate and/or calcium phosphate may be employed along with various disintegrants such as starch, alginic acid and/or certain complex silicates, together with binding agents such as polyvinylpyrrolidone, sucrose, gelatin and/or acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the active pharmaceutical agent therein may be combined with various sweetening or flavoring agents, coloring matter or dyes and, if desired, emulsifying or suspending agents, together with diluents such as water, ethanol, propylene glycol, glycerin and/or combinations thereof.

For parenteral administration, solutions of the compounds of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

For intranasal administration or administration by inhalation, the compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of a compound of this invention. Capsules and cartridges (made, for example, from gelatin) for use in an inhaler or insufflator may be formulated containing a powder mix of a compound or compounds of the invention and a suitable powder base such as lactose or starch.

The pharmaceutical composition provided herein can also be used with another pharmaceutically active agent effective for a disease such as neurodisorders, cardiovascular disorders, tumors, AIDS, depression, and/or type-1 and type-2 diabetes. Such additional agents can be, for example, antiviral agent, antibiotics, anti-depression agent, anti-cancer agents, immunosuppressant, anti-fungal, and a combination thereof.

The pharmaceutical composition described herein can be formulated alone or together with the other agent in a single dosage form or in a separate dosage form. Methods of preparing various pharmaceutical formulations with a certain amount of active ingredient are known, or will be apparent in light of this disclosure, to those skilled in this art. For examples of methods of preparing pharmaceutical formulations, see Remington's Pharmaceutical Sciences, Mack Publishing Company, Easton, Pa., 19th Edition (1995).

Scaffolds

In one embodiment, the invention may include a method of incorporating a NELL peptide in carriers or substrates, and the resulting substrates.

In one embodiment, a composition for inducing bone formation may include an effective amount of a first agent to induce bone formation selected from the group including but not limited to a NELL peptide, e.g., NELL1 peptide, a NELL2 peptide, an agent that alters expression of NELL1 peptide, an agent that alters the activity of a NELL1 peptide, an agent that alters expression of NELL2 peptide, an agent that alters the activity of a NELL2 peptide; and optionally a carrier.

The composition may include a second agent including, but not limited to TGF-beta, BMP2, BMP4, BMP7, bFGF, FGF, IGF (insulin like growth factors), VEGF, collagen, bone, bone matrix, tendon matrix or ligament matrix, osteogenic and/or osteoblastic cells.

In one embodiment, the carrier may be biodegradable, such as degradable by enzymatic or hydrolytic mechanisms. Examples of carriers include, but are not limited to synthetic absorbable polymers such as such as but not limited to poly(α-hydroxy acids) such as poly(L-lactide) (PLLA), poly (D, L-lactide) (PDLLA), polyglycolide (PGA), poly(lactide-co-glycolide (PLGA), poly(-caprolactone), poly(trimethylene carbonate), poly(p-dioxanone), poly(-caprolactone-co-glycolide), poly(glycolide-co-trimethylene carbonate) poly (D, L-lactide-co-trimethylene carbonate), polyarylates, polyhydroxybutyrate (PHB), polyanhydrides, poly (anhydride-co-imide), propylene-co-fumarates, polylactones, polyesters, polycarbonates, polyanionic polymers, polyanhydrides, polyester-amides, poly(amino-acids), homopolypeptides, poly(phosphazenes), poly(glaxanone), polysaccharides, and poly(orthoesters), polyglactin, polyglactic acid, polyaldonic acid, polyacrylic acids, polyalkanoates; copolymers and admixtures thereof, and any derivatives and modifications. See for example, U.S. Pat. No. 4,563,489, and PCT Int. Appl. #WO/03024316, herein incorporated by reference. Other examples of carriers include cellulosic polymers such as, but not limited to alkylcellulose, hydroxyalkylcellulose, methylcellulose, ethylcellulose, hydroxyethylcellulose, hydroxypropylcellulose, hydroxypropyl-methylcellulose, carboxymethylcellulose, and their cationic salts. Other examples of carriers include synthetic and natural bioceramics such as, but not limited to calcium carbonates, calcium phosphates, apatites, bioactive glass materials, and coral-derived apatites. See for example U.S. Patent Application 2002187104; PCT Int. Appl. WO/9731661; and PCT Int. Appl. WO/0071083, herein incorporated by reference.

In one embodiment, the carrier may further be coated by compositions, including bioglass and or apatites derived from sol-gel techniques, or from immersion techniques such as, but not limited to simulated body fluids with calcium and phosphate concentrations ranging from about 1.5 to 7-fold the natural serum concentration and adjusted by various means to solutions with pH range of about 2.8-7.8 at temperature from about 15-65 degrees C. See, for example, U.S. Pat. Nos. 6,426,114 and 6,013,591; and PCT Int. Appl. WO/9117965 herein incorporated by reference.

Other examples of carriers include collagen (e.g. Collastat, Helistat collagen sponges), hyaluronan, fibrin, chitosan, alginate, and gelatin, or a mixture thereof. See for example, PCT Int. Appls. WO/9505846; WO/02085422, the teachings of which are incorporated herein by reference.

In one embodiment, the carrier may include heparin-binding agents; including but not limited to heparin-like polymers e.g. dextran sulfate, chondroitin sulfate, heparin sulfate, fucan, alginate, or their derivatives; and peptide fragments with amino acid modifications to increase heparin affinity. See for example, Journal of Biological Chemistry (2003), 278(44), p. 43229-43235, the teachings of which are incorporated herein by reference.

In one embodiment, the substrate may be in the form of a liquid, solid or gel.

In one embodiment, the substrate may include a carrier that is in the form of a flowable gel. The gel may be selected so as to be injectable, such as via a syringe at the site where bone formation is desired. The gel may be a chemical gel which may be a chemical gel formed by primary bonds, and controlled by pH, ionic groups, and/or solvent concentration. The gel may also be a physical gel which may be formed by secondary bonds and controlled by temperature and viscosity. Examples of gels include, but are not limited to, pluronics, gelatin, hyaluronan, collagen, polylactide-polyethylene glycol solutions and conjugates, chitosan, chitosan & b-glycerophosphate (BST-gel), alginates, agarose, hydroxypropyl cellulose, methyl cellulose, polyethylene oxide, polylactides/glycolides in N-methyl-2-pyrrolidone. See for example, Anatomical Record (2001), 263(4), 342-349, the teachings of which are incorporated herein by reference.

In one embodiment, the carrier may be photopolymerizable, such as by electromagnetic radiation with wavelength of at least about 250 nm. Example of photopolymerizable polymers include polyethylene (PEG) acrylate derivatives, PEG methacrylate derivatives, propylene fumarate-co-ethylene glycol, polyvinyl alcohol derivatives, PEG-co-poly(-hydroxy acid) diacrylate macromers, and modified polysaccharides such as hyaluronic acid derivatives and dextran methacrylate. See for example, U.S. Pat. No. 5,410,016, herein incorporated by reference.

In one embodiment, the substrate may include a carrier that is temperature sensitive. Examples include carriers made from N-isopropylacrylamide (NiPAM), or modified NiPAM with lowered lower critical solution temperature (LCST) and enhanced peptide (e.g. NELL1) binding by incorporation of ethyl methacrylate and N-acryloxysuccinimide; or alkyl methacrylates such as butylmethacrylate, hexylmethacrylate and dodecylmethacrylate (PCT Int. Appl. WO/2001070288; U.S. Pat. No. 5,124,151, the teachings of which are incorporated herein by reference).

In one embodiment, where the carrier may have a surface that is decorated and/or immobilized with cell adhesion molecules, adhesion peptides, and adhesion peptide analogs which may promote cell-matrix attachment via receptor mediated mechanisms, and/or molecular moieties which may promote adhesion via non-receptor mediated mechanisms binding such as, but not limited to polycationic polyamino-acid-peptides (e.g. poly-lysine), polyanionic polyamino-acid-peptides, Mefp-class adhesive molecules and other DOPA-rich peptides (e.g. poly-lysine-DOPA), polysaccharides, and proteoglycans. See for example, PCT Int. Appl. WO/2004005421; WO/2003008376; WO/9734016, the teachings of which are incorporated herein by reference.

In one embodiment, the carrier may include comprised of sequestering agents such as, but not limited to, collagen, gelatin, hyaluronic acid, alginate, poly(ethylene glycol), alkylcellulose (including hydroxyalkylcellulose), including methylcellulose, ethylcellulose, hydroxyethylcellulose, hydroxypropylcellulose, hydroxypropyl-methylcellulose, and carboxymethylcellulose, blood, fibrin, polyoxyethylene oxide, calcium sulfate hemihydrate, apatites, carboxyvinyl polymer, and poly(vinyl alcohol). See for example, U.S. Pat. No. 6,620,406, herein incorporated by reference.

In one embodiment, the carrier may include surfactants to promote NELL1 or NELL2 stability and/or distribution within the carrier materials such as, but not limited to polyoxyester (e.g. polysorbate 80, polysorbate 20 or Pluronic F-68).

In one embodiment, the carrier may include buffering agents such as, but not limited to glycine, glutamic acid hydrochloride, sodium chloride, guanidine, heparin, glutamic acid hydrochloride, acetic acid, succinic acid, polysorbate, dextran sulfate, sucrose, and amino acids. See for example, U.S. Pat. No. 5,385,887, herein incorporated by reference. In one embodiment, the carrier may include a combination of materials such as those listed above.

By way of example, the carrier may be a PLGA/collagen carrier membrane. The membrane may be soaked in a solution of an agent including for example, NELL1 peptide, NELL2 peptide, or a mixture thereof.

In one embodiment, an implant for use in the human body may include a substrate that includes one or more agents described above, including for example NELL1 peptide, NELL2 peptide, or a mixture thereof in an amount sufficient to induce bone formation proximate to the implant.

In one embodiment, an implant for use in the human body may include a substrate having a surface that includes an agent such as NELL1 peptide, NELL2 peptide, or a mixture thereof in an amount sufficient to induce bone formation proximate to the implant.

In one embodiment, an implant for use in the human body may include a substrate having a surface including osteogenic cells, and for example NELL1 or NELL2 in an amount sufficient to induce bone formation. In one embodiment, the implant may be seeded with cells, including but not limited to autologous cells, osteogenic or osteoblastic cells, cells expressing a NELL peptide such as NELL1 peptide, NELL2 peptide, or a mixture thereof or another osteogenic molecule.

An implant may include a substrate formed into the shape of a mesh, pin, screw, plate, or prosthetic joint. By way of example, a substrate may be in a form of a dental or orthopedic implant and may include agent such as for example NELL1 peptide, NELL2 peptide, or a mixture thereof may be used to enhance integration in bone in proximity to the implant. An implant may include a substrate that is resorbable, such as a substrate including collagen.

In one example, a composition according to this invention may be contained within a time release tablet.

An agent such as a NELL peptide, e.g., the NELL1 peptide, NELL2 peptide, or a mixture thereof peptide may be combined with an acceptable carrier to form a pharmacological composition. Acceptable carriers can contain a physiologically acceptable compound that acts, for example, to stabilize the composition or to increase or decrease the absorption of the agent. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the anti-mitotic agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of a carrier, including a physiologically acceptable compound depends, for example, on the route of administration.

The compositions can be administered in a variety of unit dosage forms depending upon the method of administration. For example, unit dosage forms suitable may include powder, tablets, pills, capsules.

The compositions of this invention may comprise a solution of an agent such as a NELL peptide such as the NELL1 peptide, NELL2 peptide, or a mixture thereof peptide dissolved in a pharmaceutically acceptable carrier, such as an aqueous carrier for water-soluble peptides. A variety of carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of an agent such as a NELL peptide, e.g., NELL1 peptide, NELL2 peptide, or a mixture thereof peptide in these formulations can vary widely, and will be selected primarily based on fluid volumes, viscosities, body weight and the like in accordance with the particular mode of administration selected and the patient's needs.

In some embodiments, the scaffold can include Other examples of carriers include synthetic and natural bioceramics such as, but not limited to calcium carbonates, calcium phosphates, apatites, bioactive glass materials, and coral-derived apatites. See for example U.S. Patent Application 2002187104; PCT Int. Appl. WO/9731661; and PCT Int. Appl. WO/0071083, the teachings of which are incorporated herein by reference. Additional examples of bioceramic carriers include autologous, allogeneic, and xenogenic bone grafts, which may be intact or de-proteinized or de-mineralized. Other examples of carriers include synthetic and natural bioceramics and polymers and composites thereof, that increase the osteopontin gene expression of osteoblasts or their progenitors by at least 1.5 fold when the local calcium and phosphate concentrations of the local microenvironment are between 0.01-10 mM (Calcium) and 0.01-3 mM (Phosphate), respectively; and synthetic and natural bioceramics and polymers and composites thereof, that increase the osteopontin gene expression of osteoblasts or their progenitors by at least 1.5 fold when the local phosphate and calcium concentrations of the local microenvironment are between 0.01-10 mM (Phosphate) and 0.01-3 mM (Calcium).

In one embodiment, the carrier may further be coated by compositions, including bioglass and or apatites derived from sol-gel techniques, or from immersion techniques such as, but not limited to simulated body fluids with calcium and phosphate concentrations ranging from about 0.1 to 10-fold the natural serum concentration and adjusted by various means to solutions with pH range of about 2.8-9.8 at temperature from about 15-65° C., depending on carrier material. See, for example, U.S. Pat. Nos. 6,426,114 and 6,013,591; and International Application WO/9117965 incorporated herein by reference. Other examples of coating materials include synthetic and natural bioceramics and polymers and composites thereof, that increase the osteopontin gene expression of osteoblasts or their progenitors by at least 1.5 fold when the local calcium and phosphate concentrations of the local microenvironment are between 0.01-10 mM (Calcium) and 0.01-3 mM (Phosphate), respectively; and synthetic and natural bioceramics and polymers and composites thereof, that increase the osteopontin gene expression of osteoblasts or their progenitors by at least 1.5 fold when the local phosphate and calcium concentrations of the local microenvironment are between 0.01-10 mM (Phosphate) and 0.01-3 mM (Calcium).

Use of the Pharmaceutical Composition

In accordance with embodiments of the invention, a pharmaceutical composition of the various described embodiments can be administered to a mammal for treating or preventing a bone condition or bone related conditions. As used herein, the term "mammal" encompasses all mammalian subjects including human beings and animals.

In one embodiment, the pharmaceutical composition can be administered to a mammal for treating, preventing, or ameliorating a bone condition where bone generation is desirable.

In another embodiment, the pharmaceutical composition provided herein can be administered to a mammal for treating, preventing or ameliorating a bone condition where bone generation is excessive or undesirable. In a further embodiment, the pharmaceutical composition provided herein can be administered to a mammal for treating, preventing or ameliorating a bone condition.

The various bone conditions that can be treated, prevented, and/or ameliorated by the pharmaceutical composition described herein are described above.

EXAMPLES

The embodiments of the present invention will be illustrated by the following set forth examples. All parameters and data are not to be construed to unduly limit the scope of the embodiments of the invention.

Example 1

Bone Formation Using a Calvarial Wound Model

General Procedures

In one embodiment, the critical size defect in a non-union model can be used to determine the proper concentration for NELL1 in calvarial repair. Calvarial defects have been used as models to test bone regeneration under a non-load bearing conditions (Hollinger, J.O. and J. C. Kleinschmidt, J Craniofac Surg, 1990. 1(1): p. 60-8). An exemplary procedure is described below.

Standardization. To standardize bone repair characteristics, skeletally mature 5 month old male Sprague-Dawley rats rather than growing (skeletally immature animals) animals will be used for the survival surgeries (Allen, M. R. and S. A. Bloomfield, J Appl Physiol, 2003. 94(2): p. 642-50). After induction of anesthesia, the scalp area of adult rats will be shaved, prepped 3× with alcohol and betadine, and then draped with sterile drapes. A full-thickness scalp incision will be made and the periosteum reflected to expose bilateral parietal bones. A trephine drill will be used under constant irrigation with sterile saline to prevent overheating the bone edges. A full-thickness craniotomy defect will be created in each parietal bone with care to avoid injury to the underlying dura [i.e., two parietal defects per rat; each defect diameter=5 mm (critical size)]. The estimated healing rate of bilateral, untreated 5 mm defects were provided in Table 2.

TABLE 2

| Intervention Groups 5 mm Diameter (Critical) = 19.6 $mm^2$ Total Area | | |
|---|---|---|
| Group I - Final Concentration = Total NELL1 (ng)/Total Area ($mm^2$) | Total NELL1 Applied (ng) | # Animals |
| ceramic/collagen carrier only (control) | — | 5 rats |
| ceramic/collagen + 5 ng/$mm^2$ NELL1 | 98 | 5 rats |
| ceramic/collagen + 15 ng/$mm^2$ NELL1 | 294 | 5 rats |
| ceramic/collagen + 30 ng/$mm^2$ NELL1 | 589 | 5 rats |
| ceramic/collagen + 60 ng/$mm^2$ NELL1 | 1178 | 5 rats |
| ceramic/collagen + 120 ng/$mm^2$ NELL1 | 2356 | 5 rats |
| ceramic/collagen + 240 ng/$mm^2$ NELL1 | 4712 | 5 rats |
| # Animals Used -Group I | | 35 rats |
| Group II - Final Concentration = Total BMP (ng)/Total Area ($mm^2$) | Total BMP Applied (ng) | # Animals |
| ceramic/collagen carrier only (control) | — | 5 rats |
| ceramic/collagen + 30 ng/$mm^2$ BMP2 | 589 | 5 rats |
| ceramic/collagen + 60 ng/$mm^2$ BMP2 | 1178 | 5 rats |
| ceramic/collagen + 120 ng/$mm^2$ BMP2 | 2356 | 5 rats |
| ceramic/collagen + 240 ng/$mm^2$ BMP2 | 4712 | 5 rats |
| ceramic/collagen + 30 ng/$mm^2$ BMP7 | 589 | 5 rats |
| ceramic/collagen + 60 ng/$mm^2$ BMP7 | 1178 | 5 rats |
| ceramic/collagen + 120 ng/$mm^2$ BMP7 | 2356 | 5 rats |
| ceramic/collagen + 240 ng/$mm^2$ BMP7 | 4712 | 5 rats |
| # Animals Used - Group II | | 45 rats |

Following creation, each defect will be flushed with saline to remove bone debris and then grafted with either control ceramic carrier mixed with sterile saline or with ceramic carrier mixed with differential NELL1 doses to determine the optimal NELL1 treatment concentration. NELL1 concentration will be standardized according to defect area (i.e., amount of NELL1 protein (ng) per $mm^2$) (Table 2, Group I). Five rats (N=10 defects) will be used for each intervention subgroup in Group I (N=35 rats total) (Table 2). In addition, different concentrations of BMP2 and BMP7 will be applied in an identical fashion to the 5 mm defect models (Table 2, Group II) (N=45 rats). The concentrations for NELL1 testing are based on preliminary studies. The concentrations for BMP testing are based on published studies for 8 mm diameter rat calvarial defects in which BMP concentrations (by area) ranged from ~20 ng/$mm^2$ to ~600 ng/$mm^2$ (Table 3).

TABLE 3

BMP2 Dosages in Published Rat Calvarial Critical-Sized Defect Models

| Final Concentration = Total BMP2 (ng)/ Total Area ($mm^2$) | Total BMP2 Applied (μg) | Defect Diameter | Defect Area ($mm^2$) | Strain | Age | Sex | Delivery System | Ref |
|---|---|---|---|---|---|---|---|---|
| 200 and 600* ng/$mm^2$ | 10 and 30* (rhBMP2) | 8 mm | 50 | Long Evans | 28-35 | M F | PLGA microparticles | a |
| 20, 100, and 400* ng/$mm^2$ | 1, 5, and 20* (nglBMP2) | 8 mm | 50 | Sprague Dawley | 84-92 | F | Fibrin matrix | b |
| 44 and 130* ng/$mm^2$ | 2.2 and 6.5* (rhBMP2) | 8 mm | 50 | Long Evans | 28-35 | M F | ICBM | c |
| 100 ng/$mm^2$ | 5 (rhBMP2) | 8 mm | 50 | NA | NA | NA | PEG-based hydrogel | d |

*Indicates application dosage with the most bone formation.

Abbreviations: F (female); ICBM (insoluble collagenous bone matrix); M (male); NA (not available); nglBMP2 (nonglycosylated BMP2); PEG (polyethylene glycol); PLGA (microparticles of poly (D,L-lactide-co-glycolide); rhBMP2 (recombinant BMP2)

a Kenley, R., et al., J Biomed Mater Res, 1994. 28(10): p. 1139-47;

b Schmoekel, H., et al., J Orthop Res, 2004. 22(2): p. 376-81;

c Marden, L. J., et al., J Biomed Mater Res, 1994. 28(10): p. 1127-38;

d Lutolf, M. P., et al., Nat Biotechnol, 2003. 21(5): p. 513-8

The five rats in each intervention subgroup from Groups I and II (Table 2) will undergo live serial weekly imaging with micro-CT for 8 consecutive weeks using established protocols (Cowan, C. M., et al., *Adipose-derived adult stromal cells heal critical-size mouse calvarial defects*. Nat Biotechnol, 2004. 22(5): p. 560-7). The live micro-CT will provide accurate real-time quantitative data on bone density and bone regeneration area and volume as well as some qualitative data on bone morphology in the different intervention subgroups. At eight weeks, the animals will be sacrificed for high resolution, cadaveric micro-CT analyses and histology. Calvarial sections will undergo hematoxylin and eosin (H&E) staining to histologically assess the quality of bone formation. If cartilage is observed, Alcian blue will be used to verify the finding. Optimal concentrations for NELL1, BMP2, and BMP7 will be defined as the concentration inducing the largest CT-derived area of histologically confirmed bone at 8 weeks. If a plateau in bone formation is observed beyond a certain concentration, the lowest concentration at which the plateau is reached will be termed "optimal."

Equipment. High resolution micro-CT will utilize the latest 9-20 μm resolution technology from μCT40 (Scanco, Pa.) as previously published (Zhang, X., et al., J Clin Invest, 2002. 110(6): p. 861-70). Micro-CT data can be collected at 50 kVp and 160 μA and reconstructed using the cone-beam algorithm supplied with the micro-CT scanner by Scanco. Both 2D and 3D data will be acquired and analyzed to ensure the optimal characterization of biologic behavior. Visualization and reconstruction of the data can be performed using the MetaMorph® Imaging System (for 2-D) (Universal Imaging Corporation, Downingtown, Pa.), Image Pro Plus version 5.0 (Media Cybernetics, Carlsbad, Calif.) (for 2D), and Amira™ (for 3-D) (Visual Concepts GmbH, Berlin, Germany).

CT-based morphometric analyses of a number of known bone-specific 3-D structural parameters including: 1) bone volume/tissue volume-number of bone voxels in the volume of interest (VOI) divided by the total number of tissue voxels in the VOI; 2) mineralization density-radiopacity of the bone mass divided by the volume of bone mass; and 3) trabecular thickness, trabecular number, and trabecular separation (derived from bone volumes and surface areas) can be performed (Borah, B. D., T. E. et al., JBMR, 2000. 15(9): p. 1786-1797).

Scaffold fabrication. The ceramic carrier supplied by MTF is marketed under the name Synthacer. Synthacer is available in block cylindrical forms (95% hydroxyapatite; 200-800 micron pore size, 65-80% porous), and in loose powder form. The experiments will utilize block Synthacer disks that are made to fit the corresponding defects; as supplied by MTF. Initial studies on apatite carriers demonstrated faster osteoinductive response times in collagen/growth factor-coated apatites relative to collagen-free controls, and thus, all growth factors will be incorporated in a type I collagen solution. The solution can be prepared by adding growth factors at 0° C. to pH-adjusted collagen solution. Pre-determined amounts of collagen I/growth factor solution will then be applied onto each disk and the formulated scaffolds will be brought to 20° C. for gelation and then air dried to form a thin layer of collagen/growth factor. If necessary, other biomaterials (hyaluronan, fibrin, or alginate) may be employed to replace the collagen component.

Analyses of craniofacial bone formation using optimized NELL1, BMP2, and BMP7 concentrations. Animal surgery will be performed as described above for the critical defect (non-union) model. Optimized NELL1, BMP2, and BMP7 concentrations will be applied using the ceramic carrier (Table 4). Controls will consist of ceramic carrier and sterile saline. To temporally delineate the newly formed bone on histology, animals will undergo sequential in vivo fluorescent labeling with a single intraperitoneal injection of Calcein blue (30 mg/kg body weight) at day 0 (immediately after surgery), a single intraperitoneal injection of Xylenol orange (90 mg/kg body weight) at day 14, and a single intraperitoneal injection of Calcein (10 mg/kg body weight) at day 28. Calcein blue (emits blue), Xylenol orange (emits orange), and Calcein (emits green) are chelating fluorochromes with similar distribution patterns to radiolabelled calcium that deposit in sites of active bone or cartilage matrix mineralization (reviewed in Lee, T. C., et al., J Anat, 2003. 203(2): p. 161-72). Measurement of the distance between the different fluorochrome bands divided by the administration interval will allow for calculation of the mineral apposition rate (MAR) as described by Iwamoto et al. (Iwamoto, J., J. K. Yeh, and J. F. Aloia, J Bone Miner Res, 2000. 15(9): p. 1842-9).

In addition, each animal will undergo live serial weekly imaging with micro-CT and micro-PET using established protocols until sacrifice (Cowan, C. M., et al., Nat Biotechnol, 2004. 22(5): p. 560-7; Berger, F., et al., Eur J Nucl Med Mol Imaging, 2002. 29(9): p. 1225-36). Micro-PET will facilitate quantitative analysis of how NELL1, BMP2, or BMP7 addition may affect bone metabolic activities in a temporally and spatially distinct fashion. Subgroup animals will be sacrificed at 1, 2, 4, and 8 weeks. Identically treated, paired calvarial specimens from each animal will be differentially harvested and processed. One specimen will be harvested with a large rim of normal tissue and fixed in 4% paraformaldehyde for histology and subsequent Phase II cellular analyses. The other specimen will be harvested with a small rim (<2 mm) of normal tissue and immediately frozen in liquid nitrogen and stored at −70° C. in anticipation of more detailed Phase II molecular analyses.

TABLE 4

Optimized Intervention Groups
5 mm Diameter (Critical) = 19.6 mm Total Area

| Wound Harvest Time | 1 week | 2 weeks | 4 weeks | 8 weeks |
|---|---|---|---|---|
| ceramic/collagen carrier only (control) | 5 rats | 5 rats | 5 rats | 5 rats |
| ceramic/collagen + optimized NELL1 | 5 rats | 5 rats | 5 rats | 5 rats |
| ceramic/collagen + optimized BMP2 | 5 rats | 5 rats | 5 rats | 5 rats |
| ceramic/collagen + optimized BMP7 | 5 rats | 5 rats | 5 rats | 5 rats |
| Total Animals Used | 80 rats | | | |

The fixed specimens will first undergo morphologic analyses using high resolution micro-CT and imaging software as described above. Following this, the fixed specimen will be bisected. Half of the specimen will be demineralized, dehydrated, embedded in paraffin, sectioned (5 μm thickness), and H&E stained; the other half will be processed undecalcified and embedded in either methyl methacrylate. For visualization of in vivo labeling, four unstained, non-decalcified, non-consecutive sections (10 μm thickness) will be examined using fluorescence microscopy. Additional sections (4 μm thickness) will be stained with Masson- Goldner's trichrome for histomorphometic measurements such as trabecular bony volume and surface density as described by Hollinger et al (Hollinger, J. O., D. Buck, and J. P. Schmitz, Clin Plast Surg, 21(3): p. 463-75) (1994).

The micro-PET will provide detailed metabolic information on whether activity is most intense at the trephine rim or at the defect center and how optimized NELL1 or BMP addition will influence this activity. Both NELL1 and BMP will increase bone metabolic activity at the trephine rim and defect center. In addition, the use of different chelating fluorochromes will allow the correlation of the calculated MAR with the observed bone formation on micro-CT and metabolic activity on micro-PET as well as determine more exactly the temporal and spatial sequence of newly deposited bone (e.g., rate of central vs. rim bone deposition, dural vs. periosteal bone deposition).

Regeneration of Calvarial Bone by NELL1

Creation of calvarial defect. The critical size calvarial defect represents a non-osseous union model [which was defined as <10% healing on 3 dimensional (D) volume measurement by 3 months], while the subcritical size calvarial defect represents a delayed osseous union model (which can be defined as ≤15% healing on 3D volume measurement by 3 months). Estimated healing rate of bilateral, untreated critical size (5 mm diameter) and subcritical size (3 mm diameter) calvarial defects in the rat model are shown in Table 5. The less than 10% healing for the 5 mm defects concur with other reports in the literature (Bosch, C., et al., J Craniofac Surg, 1998. 9(4): p. 310-6). Although some rat critical size defect models involve a single 8 mm diameter defect centered over the sagittal suture (Kenley, R., et al., J Biomed Mater Res, 1994. 28(10): p. 1139-47; Schmoekel, H., et al., J Orthop Res, 2004. 22(2): p. 376-81), the bilateral model (which can accommodate dual defects up to 5 mm) was chosen for the following reasons: 1) to specifically avoid inclusion of the fibrous tissue within the sagittal suture; 2) to minimize injury to the midsagittal sinus; and 3) to allow for paired experimental design (Bosch, C., et al., J Craniofac Surg, 1998. 9(4): p. 310-6).

A delayed union model (i.e., 3 mm diameter subcritical size defect) skeletally immature animals (~3 months) were utilized. For the rat, skeletal maturity is reached at about 5 months (Allen, M. R. and S. A. Bloomfield, J Appl Physiol, 2003. 94(2): p. 642-50). Polylactide-co-glycolide (PLGA)/collagen carrier membrane was used to incorporate bioactive molecules because of PLGA's: 1) documented biocompatibility and use in existing FDA approved devices; 2) relative inertness (non-osteoinductive); 3) ease of manipulation and availability for control over bioactive molecule release kinetics (Dhiman, N., et al., Indian J Exp Biol, 2000. 38(8): p. 746-52; Panyam, J. and V. Labhasetwar, Adv Drug Deliv Rev, 2003. 55(3): p. 329-47); and 4) degradation profile (Bessho, K., et al., J Biomed Mater Res, 2002. 61: p. 61-65).

PLGA scaffolds were prepared as previously described (Cowan, C. M., et al., Nat Biotechnol, 2004. 22(5): p. 560-7). After scaffold fabrication, scaffolds were coated with type I collagen (Vitrogen®; Cohesion, Palo Alto, Calif.) in which were premixed with the appropriate amounts of either NELL1, BMP2, or sterile saline controls. The total dose of NELL1 and BMP2 for the pilot studies was 200 ng per each 3 mm diameter PLGA scaffolds to provide snug fit in the trephined defect. Controls consisted of PLGA membrane alone. Animals were sacrificed at 0, 1, 2, 3, and 4 weeks for micro-CT and histological analyses of the calvariae.

In these studies, the initial dose of 200 ng was derived empirically from in vitro NELL1 cell culture data and in vivo BMP2 critical size defect data (Table 3, supra). In vitro NELL1 concentrations in the range of 5 to 50 ng/ml concomitantly increased apoptosis and bone nodule formation, while concentrations above 100 ng/ml increased apoptosis but decreased bone nodule formation, and concentrations above 200 ng/ml were associated with increased apoptosis and minimal bone nodule formation (Zhang, X., et al., J Bone Miner Res, 2003. 18(12): p. 2126-34). Thus, this indicates that excessive NELL1 dosages will reduce bone formation. In the published BMP2 studies, a relatively low 1 μg total applied dose effectively closed 46% to 74% of an 8 mm diameter defect in 3 weeks (Schmoekel, H., et al., J Orthop Res, 2004. 22(2): p. 376-81). When normalized to total defect area, the 1 μg dose was equivalent to 20 $ng/mm^2$ (Standardization to defect area rather than volume was to facilitate comparison of the dosages in this example to published studies in which the calvarial thickness was not always available for volume calculations). The 200 ng total dose used herein, divided by total area for a 3 mm diameter defect (i.e., 7 $mm^2$=Total Area), corresponds to 28 $ng/mm^2$.

Figure 4:
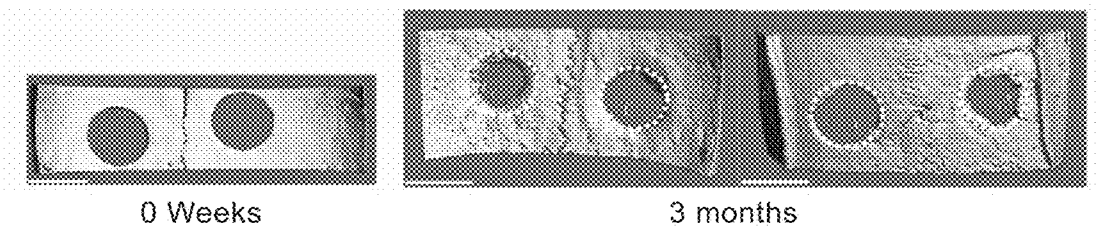
FIG. 4 is volume analyses of NELL1 or BMP2 treated calvarial defects, showing significantly increased bone formation above control (blue line) for NELL1 (green line) and BMP2 (red line). This demonstrates that NELL1 can regenerate/repair bone.

Induction of Calvarial Bone Regeneration by NELL1. Studies utilizing 200 ng total dose (28 $ng/mm^2$) NELL1 and BMP2 loaded onto PLGA membranes demonstrated significant bone formation for both NELL1 and BMP2 treated specimens over non-loaded PLGA controls (N=4 to 6 defects per treatment subgroup, per time point). Volume analysis demonstrated significantly increased bone formation for both NELL1 and BMP-2 relative to control over the 4 week study period (FIG. 4). As shown in FIG. 4, NELL1 induced significantly more bone than BMP2 at week 1.

Figures 5A, 5B, 5C:
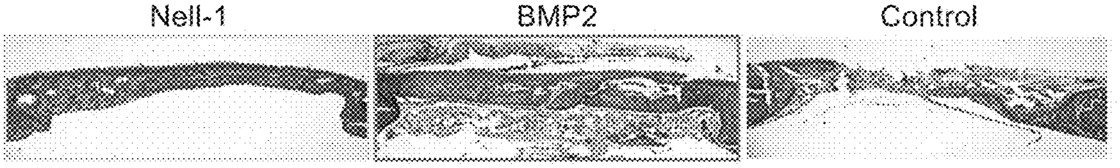
FIGS. 5A-C are micro-CT images of treated calvaria at 4 weeks.

Overall, not more than 15% bone volume regeneration is estimated at 3 months (Table 5). At 2 weeks, NELL1 and BMP2 demonstrated approximately 70-80% defect closure by surface analysis and 35-45% volume regeneration by volume analysis (FIG. 4). Histological sections confirmed the presence of bone. Osteoid deposition and trabecular branching patterns were not markedly different between NELL1 and BMP2. FIG. 5 demonstrated near 90-100% defect closure by surface analysis in the NELL1 and BMP2 treated specimens at 4 weeks which corresponded to 45-50% volume regeneration by 3D volume analysis. Histological sections confirmed the presence of bone (FIGS. 6A-6C). Again, there were no marked histological differences between NELL1 and BMP2 induced bone (FIGS. 6A-6C).

Of note, the standard deviation on surface analyses was significantly higher than that for volume analyses. This serves to highlight that 2D-based linear measurements may not necessarily reflect all tissue events in 3D organisms. Indeed, it can be seen from the histological specimens (FIGS. 6A-6C) that although 2D-based "defect closure" has

TABLE 5

Estimated Healing Rate = Volume of New Bone ($mm^3$)/Defect Volume ($mm^3$)

| Defect Diameter | Area ($\pi r^2$) | Volume* | 2 weeks | 1 month | 2 months | 3 months |
|---|---|---|---|---|---|---|
| 3 mm (Subcritical) | 7 $mm^2$ | 4.2 $mm^3$ | ~10% | 10-15% | ~15% | ~15% |
| 5 mm (Critical) | 19.6 $mm^2$ | 11.8 $mm^3$ | <10% | <10% | <10% | <10% |

*Volume was calculated by Area × Calvarial Thickness. Mean calvarial thickness measured from histology sections was 0.6 mm occurred for the NELL1 and BMP2 treated calvariae, the cross-sectional thickness of regenerated bone in the defect is not as thick as non-wounded bone. Thus, 2D-based defect "closure" does not necessarily correspond to 3D-based defect "reconstitution." Gosain et al. have also noted the importance of cross-sectional or more "3D" based data acquisition and analysis parameters in the evaluation of critical, and especially subcritical size defects (Gosain, A. K., et al., Plast Reconstr Surg, 2000. 106(2): p. 360-71; discussion 372).

These studies demonstrate that recombinant NELL1 is osteoinductive in vivo and that NELL1 induced bone is indistinguishable from BMP2 induced bone at 4 weeks.

Example 2

Mammalian System for Expression of Recombinant Human NELL (rhNell1)

In order to study the function of NELL1 and NELL2 protein/peptides, attempts were successfully made to produce and purify the peptide. The mammalian expression system used for production of rhNell1 by non-viral DNA delivery in this invention can include, but not limit to these commonly used stable expression systems listed in Table 6. The detailed protocols including vector design, host cell line culture, transfection and selection of stable cell line as well as purification of rhNell1 in HEK 293 and CHO system are described below for reference.

TABLE 6

Mammalian Expression System for production of rhNell1

| System | Parental vector | Leader sequence | Gene amplification |
|---|---|---|---|
| CHO | p3Xflag-CMV | preprotrypsin | No/optinal |
| DXB11 | mp19-Lp | human tPA | DHFR/MTX |
| HEK293 | pSecTag | immunoglobulin | No/optinal |
| NS/0 or Sp2/0 | pdCs-Fc-X | light chain of Ig and Fc fragment | DHFR/MTX |
| | pEE12 | N/A | GS/MSX |

DHFR: diydrofolate reductase; MTX: methotrexate; GS: glutamine synthetase MSX: methionine sulphoximine.

A. CHO System

Vector design: A cDNA fragment was ligated into the expression vector p3XFlag-CMV (Sigma). The resulting expression construct, pCMV-rhNell-3Xflag, includes a preprotrypsin leading sequence, cDNA fragment of the mature human NELL1 coding region and a 3Xflag sequences at c-terminal.

Host Cell line: The CHO-K1 was an adherent cell line and can be adapted to suspension culture in serum-free medium. The construct of pCMV-rhNELL1-3Xflag was transfected by either lipofectamine (Invitrogen) or calcium phosphates treatment. The stable cell lines were selected by adding G418 (400-600 ug/ml) into the cell culture medium for about two weeks. The stable transformants were further screened for single clones with high productivity of rhNELL1 by limiting dilution. The selected stable cell lines can be used in laboratory or industrial scale bioreactors for rhNell1 production.

Purification procedure: rhNELL1 peptide containing media or cell lysate was purified through anti-flag antibody M2 (Sigma) affinity column at its native condition and eluted with 3Xflag peptide.

B. HEK293 System

Vector design: A cDNA fragment was ligated into the expression vector pSecTagA (Invitrogen). The resulting expression construct, pSec-hNELL1-Tag, includes a murine immunoglobulin κ-chain leader sequence, cDNA fragment of the mature human NELL1 coding region and dual tag of Myc and His sequences at c-terminal.

Host Cell line: The human embryo kidney cell line, HEK-293 which was adapted to serum-free medium and grown in suspension format, was transfected with the NELL1 peptide expression vector, pSec-hNELL1-Tag. Cells were either cultured for a couple of days as transient transfection before collecting conditioned medium for purification of rhNELL1 or treated with Zeocin (250 ug/ml) for selection of stable expression cell line. The stable transformants were further screened for single clones with high productivity of rhNELL1 by limiting dilution. The selected stable cell lines can be used in laboratory or industrial scale bioreactors for rhNELL1 production.

Purification procedure: rhNell1 peptide containing media were purified through $Ni^{2+}$ affinity column at its native condition and eluted with 1M imidazole. The rhNELL1 was tested for its integrity, purity and bioactivity after extensively dialysis against at least 1000 volumes of PBS (pH 7.4) at 4° C. for 20 hrs.

In addition, the modifications of parental vectors for replacing existing leader sequence with a new one such as rat serum albumin, CD33, tPA and human interlukin-2 leader sequence or adding gene amplification target such as DHFR or GS into the backbone sequence will result in new expression vectors and systems. In this invention, the native signal peptide of human NELL1 is not effective enough to guide the protein secretion and sometimes even the external leading sequence didn't work well, either. Thus, the construction of expression vector with in frame fusion of a small natural secretory protein such as human granulocyte-macrophage colony stimulating factor (GM-CSF) by a spacer containing intraprotein His tag and proteolytic cleavage site as "MPHHHHHHGGGDDDDKDPM" can be needed. The epitope tags used for purification of Nell1 can be one of the following: 6× Histidines, 3XFlag, Myc, GST (glutathione S-transferase), EGFP or CTHS (C-terminal half of SUMO which stands for small ubiquitin modifying protein) etc, but also can be dual of His plus Myc as listed plasmid pSecTag in Table 6.

Furthermore, the dicistronic or multicistronic vectors using IRES can be constructed for regulatory or inducible expression of rhNELL1 under certain circumstances. The genetic modifications of host cell lines for gaining longer lasting proliferation and delayed apoptosis or compatible with special requests such as Tetracycline inducible system and Flp-In specific site integration system can be considered for improvement of rhNELL1 production.

Besides the stable expression of system for production of rhNELL1 mentioned above, a large-scale transient transfection (LST) approach using multi-milligram purified plasmid vector (pREP4) can be used to transfect HEK 293 or BHK suspension cells with cationic polymer PEI as backup alternative or complimentary to stable system.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A pharmaceutical composition for treating, preventing, or ameliorating a bone related condition in a mammal, comprising an effective amount of a NELL peptide and a carrier or scaffold that includes BMP2 and hyaluronan, wherein the effective amount is effective for a bone related condition selected from the group consisting of osteoporosis, bone loss due to microgravity, disuse atrophy, prolonged bed-rest, and a disease that involves multiple symptoms where bone metabolism is a secondary effect or is selected from the group consisting of atopic soft tissue calcification, gall stone, kidney stones, pineal gland calcification, cataracts, salivary stones, cardiac valves, and prostate stones.

2. The pharmaceutical composition of claim 1, wherein the NELL peptide is in a dosage not substantially exceeding an optimal dosage range of the NELL peptide.

3. The pharmaceutical composition of claim 1, wherein the NELL peptide is selected from the group consisting of NELL-1, NELL-2, a fragment of NELL-1 peptide, a fragment of NELL-2 peptide, and combinations thereof.

4. The pharmaceutical composition of claim 1, wherein the disease that involves multiple symptoms results in pathological calcification.

5. The pharmaceutical composition of claim 4, wherein the disease that involves multiple symptoms is a chronic kidney disease which causes renal osteodystrophy and/or vascular calcification.

6. The pharmaceutical composition of claim 1, wherein the bone related condition is selected from the group consisting of atopic soft tissue calcification, gall stone, kidney stones, pineal gland calcification, cataracts, salivary stones, cardiac valves, and prostate stones.

7. The pharmaceutical composition of claim 1, further comprising a pharmaceutically acceptable carrier.

8. The pharmaceutical composition of claim 1, further comprising a second agent, wherein the composition is effective for bone generation or treating, preventing, or ameliorating a bone related condition.

9. The pharmaceutical composition of claim 8, wherein the second agent is selected from the group consisting of a BMP protein, a TGFβ protein, FGF, IGF (insulin like growth factors), VEGF, and a combination thereof.

10. The pharmaceutical composition of claim 9, wherein the bone condition is selected from the group consisting of bone fracture, spinal fusion, long bone fracture, craniofacial bone healing or formation, dental or orthopedic implant integration, dental implant integration, or combinations thereof.

11. The pharmaceutical composition of claim 8, further comprising a pharmaceutically acceptable carrier.

12. The pharmaceutical composition of claim 1 in a formulation suitable for a mode of delivery selected from the group consisting of oral delivery, parenteral delivery, pulmonary delivery, and implantation.

13. A scaffold for treating, preventing, or ameliorating a bone related condition in a mammal, comprising an effective amount of a NELL peptide and a carrier that includes BMP2 and hyaluronan, wherein the effective amount is effective for a bone related condition selected from the group consisting of osteoporosis, bone loss due to microgravity, disuse atrophy, prolonged bed-rest, and a disease that involves multiple symptoms where bone metabolism is a secondary effect or is selected from the group consisting of atopic soft tissue calcification, gall stone, kidney stones, pineal gland calcification, cataracts, salivary stones, cardiac valves, and prostate stones.

14. The scaffold of claim 13, wherein the NELL peptide is in a dosage not substantially exceeding an optimal dosage range of the NELL peptide.

15. The scaffold of claim 13, wherein the NELL peptide is selected from the group consisting of NELL-1, NELL-2, a fragment of NELL-1 peptide, a fragment of NELL-2 peptide, and combinations thereof.

16. The scaffold of claim 13, wherein the disease that involves multiple symptoms results in pathological calcification.

17. The scaffold of claim 16, wherein the disease that involves multiple symptoms is a chronic kidney disease which causes renal osteodystrophy and/or vascular calcification.

18. The scaffold of claim 13, wherein the bone related condition is selected from the group consisting of atopic soft tissue calcification, gall stone, kidney stones, pineal gland calcification, cataracts, salivary stones, cardiac valves, and prostate stones.

19. A pharmaceutical composition for treating, preventing, or ameliorating a bone related condition in a mammal, comprising an effective amount of a NELL RNA and a carrier or scaffold that includes BMP2 and hyaluronan, wherein the effective amount is effective for a bone related condition selected from the group consisting of osteoporosis, bone loss due to microgravity, disuse atrophy, prolonged bed-rest, atopic soft tissue calcification, gall stone, kidney stones, pineal gland calcification, cataracts, salivary stones, cardiac valves, prostate stones, and a disease that involves multiple symptoms where bone metabolism is a secondary effect.

20. The pharmaceutical composition of claim 19, wherein the NELL RNA is mRNA, noncoding RNA, microRNA, dsRNA, or combinations thereof.

21. The pharmaceutical composition of claim 19, wherein the NELL RNA is stabilized by a chemical or by incorporating in NELL RNA in a nanocage or biomaterial.

22. A scaffold for treating, preventing, or ameliorating a bone related condition in a mammal, comprising an effective amount of a NELL RNA and a carrier that includes BMP2 and hyaluronan, wherein the effective amount is effective for a bone related condition selected from the group consisting of osteoporosis, bone loss due to microgravity, disuse atrophy, prolonged bed-rest, atopic soft tissue calcification, gall stone, kidney stones, pineal gland calcification, cataracts, salivary stones, cardiac valves, prostate stones, and a disease that involves multiple symptoms where bone metabolism is a secondary effect.

23. The scaffold of claim 22, wherein the NELL RNA is mRNA, noncoding RNA, microRNA, dsRNA, or combinations thereof.

24. The scaffold of claim 22, wherein the NELL RNA is stabilized by a chemical or by incorporating in NELL RNA in a nanocage or biomaterial.

* * * * *